United States Patent
Miyazaki

(10) Patent No.: US 10,349,640 B2
(45) Date of Patent: Jul. 16, 2019

(54) PREVENTIVE OR THERAPEUTIC AGENT FOR KIDNEY DISEASE

(71) Applicant: Toru Miyazaki, Tokyo (JP)

(72) Inventor: Toru Miyazaki, Tokyo (JP)

( * ) Notice: Subject to any disclaimer, the term of this patent is extended or adjusted under 35 U.S.C. 154(b) by 0 days.

(21) Appl. No.: 15/116,907

(22) PCT Filed: Feb. 6, 2015

(86) PCT No.: PCT/JP2015/053415
§ 371 (c)(1),
(2) Date: Aug. 5, 2016

(87) PCT Pub. No.: WO2015/119253
PCT Pub. Date: Aug. 13, 2015

(65) Prior Publication Data
US 2017/0172120 A1    Jun. 22, 2017

(30) Foreign Application Priority Data
Feb. 7, 2014 (JP) ................. 2014-022041

(51) Int. Cl.
| A61K 38/00 | (2006.01) |
| A61K 38/17 | (2006.01) |
| A61K 45/06 | (2006.01) |
| G01N 33/68 | (2006.01) |
| A01K 67/027 | (2006.01) |
| C07K 14/435 | (2006.01) |
| A61K 31/7088 | (2006.01) |

(52) U.S. Cl.
CPC ...... A01K 67/0276 (2013.01); A61K 31/7088 (2013.01); A61K 38/00 (2013.01); A61K 38/1761 (2013.01); A61K 45/06 (2013.01); C07K 14/435 (2013.01); G01N 33/6893 (2013.01); *A01K 2217/075* (2013.01); *A01K 2227/105* (2013.01); *A01K 2267/03* (2013.01); *A01K 2267/035* (2013.01); *G01N 2333/775* (2013.01); *G01N 2800/347* (2013.01); *G01N 2800/52* (2013.01)

(58) Field of Classification Search
None
See application file for complete search history.

(56) References Cited

U.S. PATENT DOCUMENTS 8,591,913 B2 * 11/2013 Miyazaki ................. A23L 2/66
424/185.1
2010/0105621 A1    4/2010 Cohen et al.
2010/0331244 A1 * 12/2010 Miyazaki ................. A23L 2/66
514/4.8
2013/0115220 A1    5/2013 Miyazaki
2015/0094268 A1    4/2015 Miyazaki

FOREIGN PATENT DOCUMENTS

| EP | 2572730 A1 * | 3/2013 | ......... A61K 31/7088 |
| EP | 2573192 A1 | 3/2013 | |
| JP | 2001-523264 A | 11/2001 | |
| WO | WO 2011/145723 A1 | 11/2011 | |
| WO | WO 2011/145725 A1 | 11/2011 | |
| WO | WO 2013/162021 A1 | 10/2013 | |

OTHER PUBLICATIONS

Burgess et al. (J. Cell Biol. 111:2129-2138, 1990) (Year: 1990).*
Lazar et al. (Mol. Cell. Biol., 8:1247-1252, 1988) (Year: 1988).*
Bork (Genome Research, 2000,10:398-400) (Year: 2000).*
Bowie et al. (Science, 1990, 247:1306-1310) (Year: 1990).*
Vajdos et al. (J Mol Biol. Jul. 5, 2002;320(2):415-28 (Year: 2002).*
Brown et al. (J Immunol. May 1996;156(9):3285-91 (Year: 1996).*
Guido et al (Curr Med Chem. 2008;15(1):37-46) (Year: 2008).*
Clark et al (J. Med. Chem., 2014, 57 (12), pp. 5023-5038) (Year: 2014).*
Aagaard et al (Advanced Drug Delivery Reviews 59 (2007) 75-86) (Year: 2007).*
Warzocha et al (Leukemia and Lymphoma (1997) vol. 24. pp. 267-281) (Year: 1997).*
McKeague et al (J Nucleic Acids. 2012:748913. Epub Oct. 24, 2012) (Year: 2012).*
Formentini et al (Nephrol Dial Transplant (2012) 27 (Supple 3): iii81-iii88) (Year: 2012).*
Devuyst et al (Lancet. May 24, 2014; 383(9931): 1844-1859) (Year: 2014).*
Breyer et al (Nat Rev Drug Discov. Aug. 2016; 15(8): 568-588) (Year: 2016).*
Ludwig et al (Haematologica 2007; 92:1411-1414) (Year: 2007).*
Ma (Modern Drug Discovery 2004, 7(6)) (Year: 2004).*

(Continued)

*Primary Examiner* — Brian Gangle
*Assistant Examiner* — Andrea K McCollum
(74) *Attorney, Agent, or Firm* — Leydig, Voit & Mayer, Ltd.

(57) ABSTRACT

The present invention provides a prophylactic or therapeutic agent for a kidney disease, comprising Apoptosis Inhibitor of Macrophage (AIM) or a partial peptide thereof, or a nucleic acid comprising a base sequence encoding the same, or a screening method for a prophylactic or therapeutic agent for a kidney disease, comprising using an animal obtained by subjecting a non-human mammal deficient in AIM expression to unilateral ureteral obstruction or transient kidney ischemia/reperfusion and the like.

8 Claims, 24 Drawing Sheets

Specification includes a Sequence Listing.

(56) References Cited

OTHER PUBLICATIONS

Langston et al (published on dvm360.com on Jun. 11, 2011) (Year: 2011).*

Arai et al., "Obesity-Associated Autoantibody Production Requires AIM to Retain the Immunoglobulin M Immune Complex on Follicular Dendritic Cells," *Cell Reports*, 3(4): 1187-1198 (Apr. 25, 2013).

Kitada et al., "Apoptosis inhibitor of macrophage (AIM) promotes phagocytosis of renal tubular necrosis and induces repair and regeneration of renal disorder," *The Japanese Journal of Nephrology*, 56(3): 321, abstract O-288 (2014).

Kurokawa et al., "Macrophage-Derived AIM Is Endocytosed into Adipocytes and Decreases Lipid Droplets via Inhibition of Fatty Acid Synthase Activity," *Cell Metabolism*, 11(6): 479-492 (Jun. 9, 2010).

Kurokawa et al., "Apoptosis inhibitor of macrophage (AIM) is required for obesity-associated recruitment of inflammatory macrophages into adipose tissue," *PNAS*, 108(29), 12072-12077 (2011).

Miyazaki et al., "Increased Susceptibility of Thymocytes to Apoptosis in Mice Lacking AIM, a Novel Murine Macrophage-derived Soluble Factor Belonging to the Scavenger Receptor Cysteine-rich Domain Superfamily," *The Journal of Experimental Medicine*, 189(2): 413-422 (Jan. 18, 1999).

Japanese Patent Office, International Search Report in International Patent Application No. PCT/JP2015/053415 (dated Mar. 24, 2015).

Arellano et al., "Clinical uses of GM-CSF, a critical appraisal and update," *Biologics.*, 2(1): 13-27 (2008).

Itoh et al., "Preventive Effect of Lactacystin, a Selective Proteasome Inhibitor, on Ischemic Acute Renal Failure in Rats," *J. Pharmacol. Exp. Ther*. 298(2): 501-507 (2001).

Arai et al., "Apoptosis inhibitor of macrophage protein enhances intraluminal debris clearance and ameliorates acute kidney injury in mice," *Nat. Med.*, 22(2): 183-193 and supplemental "Online Methods" (2016).

Merck Research Laboratories, *The Merck Manual of Diagnosis and Therapy*, 18$^{th}$ edition, entry for "Renal Failure," pp. 1980-1989 (2006).

Oshima et al., "Association of apoptosis inhibitor of macrophage (AIM) expression with urinary protein and kidney dysfunction," *Clin. Exp. Nephrol.*, 21(1): 35-42 (2017).

Selewski et al., "Acute Kidney Injury," *Pediatr. Rev.*, 35(1): 30-41 (2014).

Yamazaki et al., "A proteolytic modification of AIM promotes its renal excretion," *Sci. Rep.*, 6: 38762 [doi: 10.1038/srep38762] (2016).

European Patent Office, Extended European Search Report in European Patent Application No. 15746352.2 (dated Oct. 20, 2017).

Alikhan et al., "Colony-Stimulating Factor-1 Promotes Kidney Growth and Repair via Alteration of Macrophage Responses," *Am. J. Pathol.*, 179(3): 1243-1256 (2011).

Hayata et al., "Effect of a serine protease inhibitor on the progression of chronic renal failure," *Am. J. Physiol. Renal Physiol.*, 303(8): F1126-F1135 (2012).

Menke et al., "CSF-1 signals directly to renal tubular epithelial cells to mediate repair in mice," *J. Clin. Invest.*, 119(8): 2330-2342 (2009).

Morinaga et al., "The antifibrotic effect of a serine protease inhibitor in the kidney," *Am. J. Physiol. Renal Physiol.*, 305(2): F173-F181 (2013).

Sridharan et al., "Therapeutic nucleic acids: current clinical status," *Br. J. Clin. Pharmacol.*, 82(3): 659-672 (2016).

Venkatachalam et al., "Failed Tubule Recovery, AKI-CKD Transition, and Kidney Disease Progression," *J. Am. Soc. Nephrol.*, 26(8): 1765-1776 (2015).

* cited by examiner

Fig. 1
A
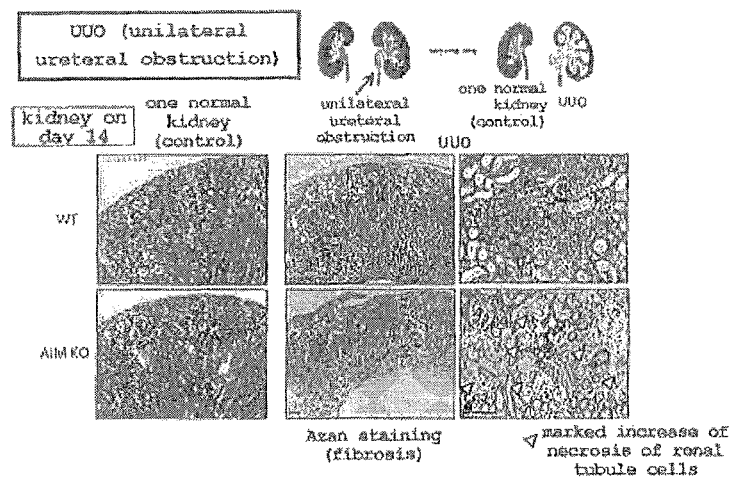
B
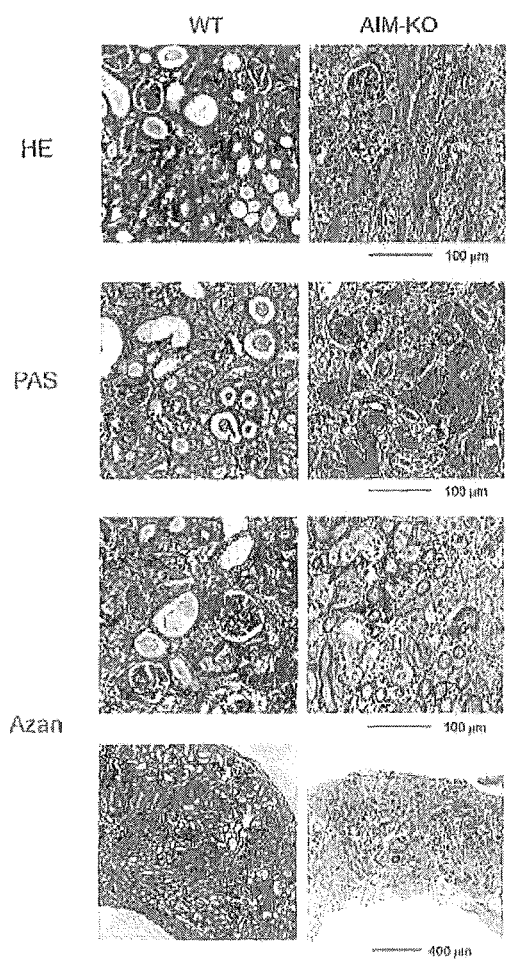

Fig. 2
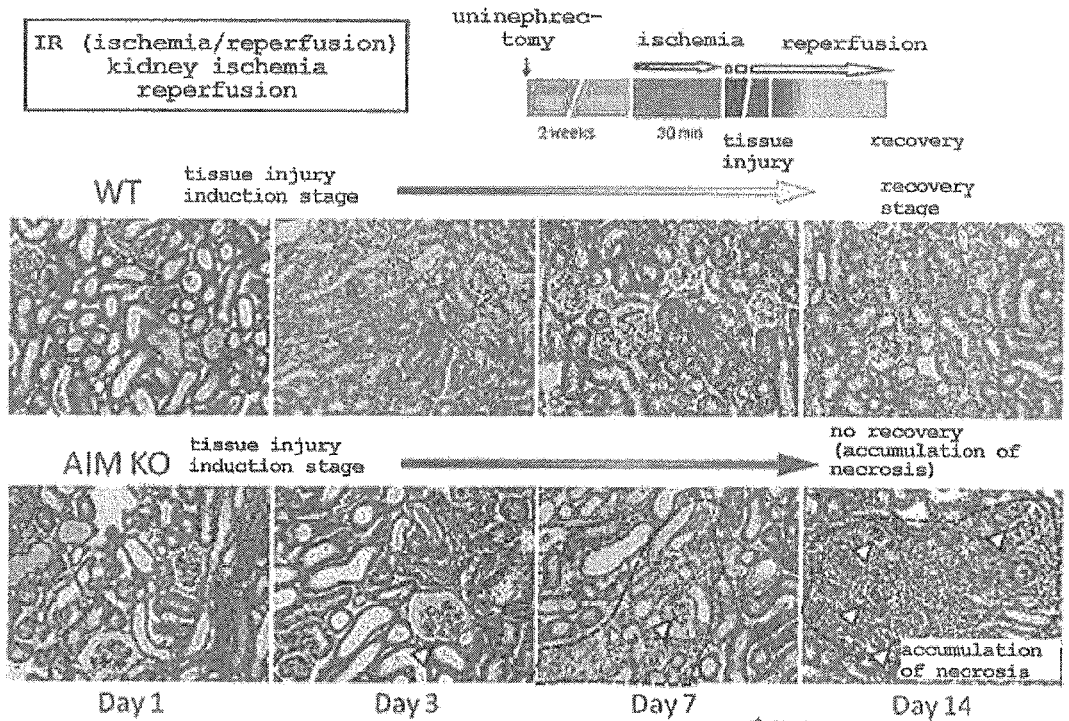
Fig. 3
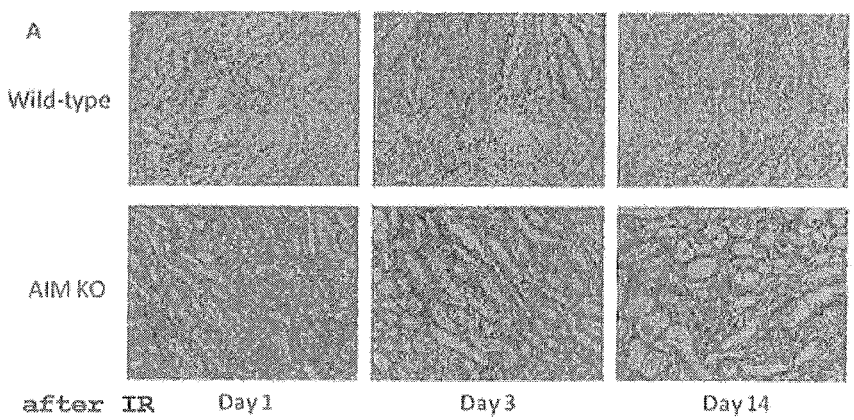
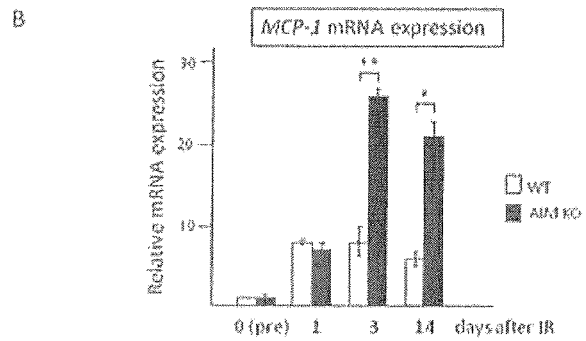

◀ dead cell mass clogged in proximal renal tubule (intraluminal debris)

◀ dead cell mass clogged in proximal renal tubule (intraluminal debris)

─── 50 μm

Fig. 32
A
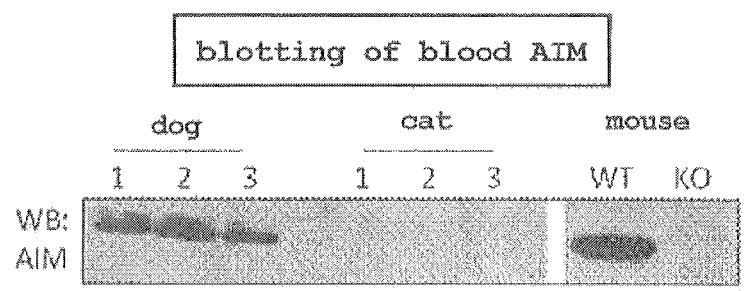
B
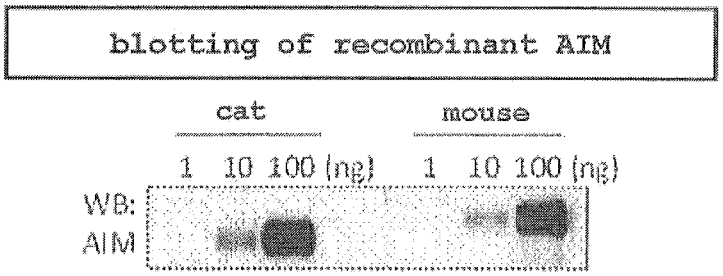

Fig. 33
A
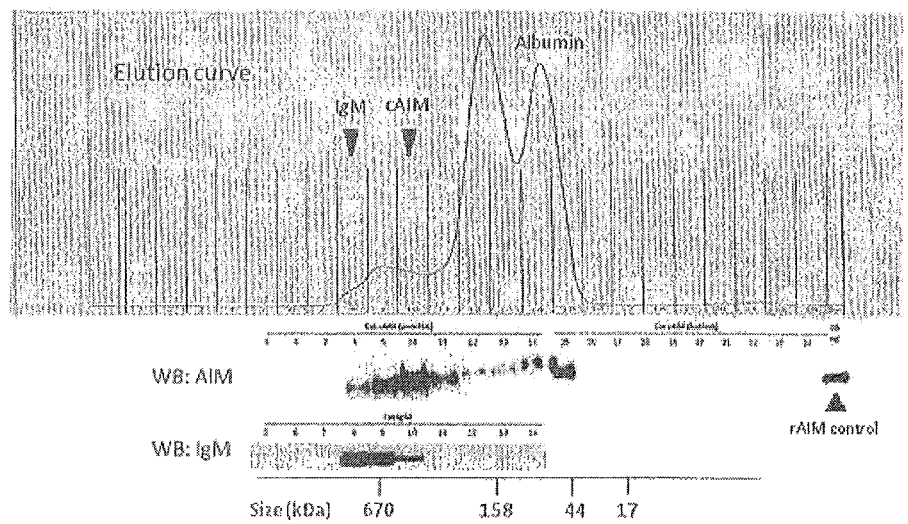
B
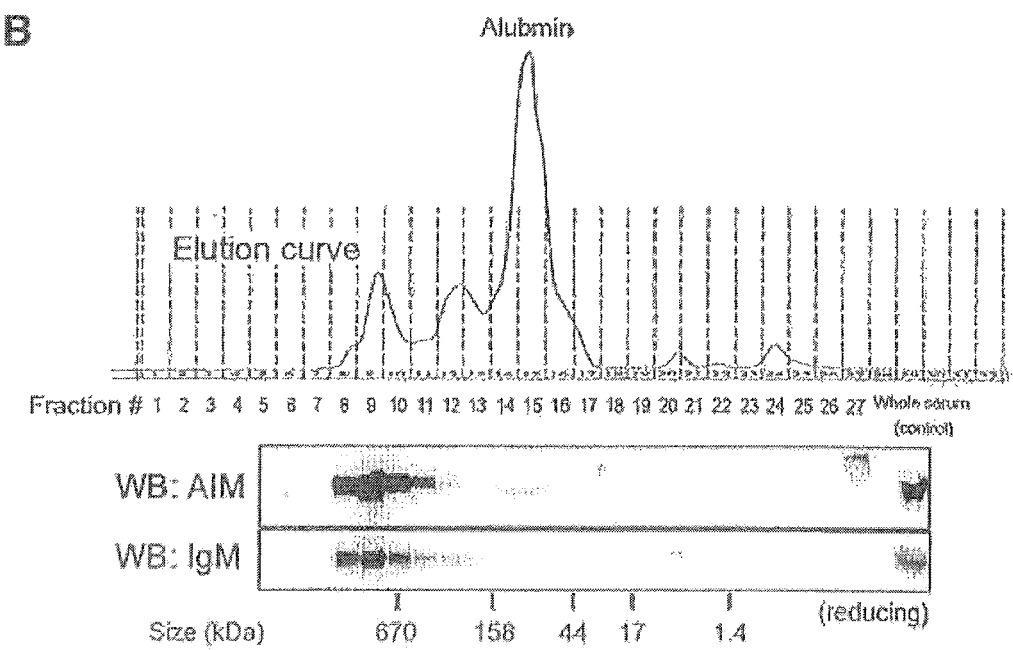

Fig. 34

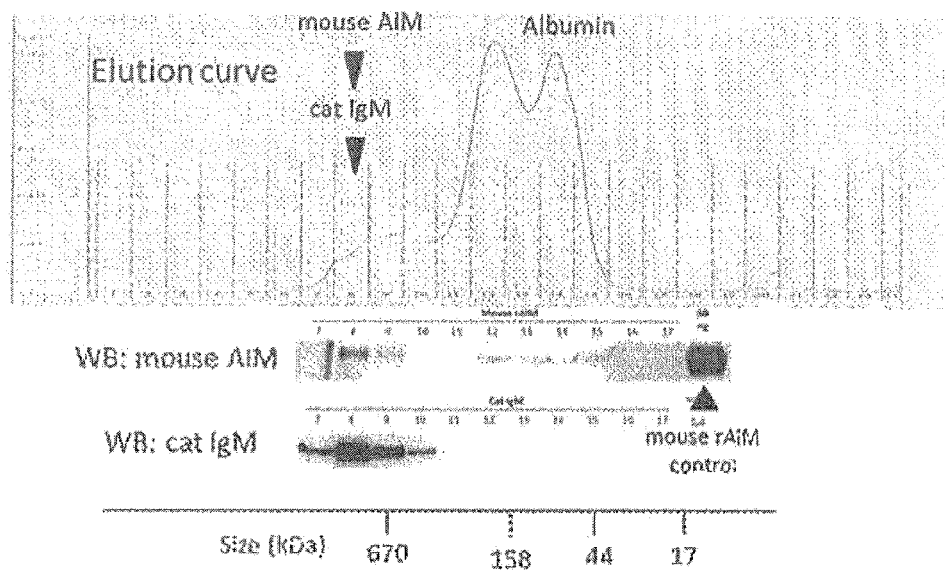

Fig. 35 cat AIM cDNA sequence

```
agaactctcc gttgctgccc tgggcctcc tcgcggcctc ggattccagc
tcagcctctc ccgtcgcctg gctcatggcg ctactcttct ccctaatcct
cgccatttac actggacctg gcattttagg gtcttttcc agagtgcggc
tagtgggagg cgaccaccgc tgtgaaggtc gtgtggagtt gcagcaggat
gacgagtggg tcaccgtgtg tgatgactac tggaacatgg actctgtggc
cgtgctgtgc cgggagctgg gctgtggggc ggccaggaag accatgagtg
gcaccgtgta tggaccagtg acaccaaagg accaaaaagt cttcatccac
ctgttcagat gcaatgggat cgaagaaagc ctgtctcagt gcgagaggga
agatgcaatc ggatgctccc atgttgagga tgcgggagcc gtgtgcgagc
ccatttacac tggactggc attttagggc cggagagtgt gaggctggcc
gatggccccg ggcgctgcca gggccgagtg gaggtgaagt tccgagggga
gtggagctct gtgtgccaag caggctggag ctttgcagcc gccaaggtgg
tgtgccggca gctgggggtgt ggacgggcca ccctgacccg gagaggctgc
aacaaagcga cccagggcca agggccatc tggcagagaa aggcgtcatg
ctcaggacaa gaagtgagcc ttcaagattg cctttctgaa gtttgggaac
acaactgtac ccacaatgag gacgtgtggg tcgaatgtga agatcccttt
gccttgaagc tggtaggagg acgcagccac tgtgagggga ggctggaggt
gctgcacaag ggcgagtggg gctctgtctg cgacgacggc tggggacaag
acgcagaccg ggtggtgtgc aggcagctgg gctgcggca gccctgtct
ccgcctgtca aagtccggag aaggttcggc cccggggtcg gccgcatctg
gctggacgac gtcaagtgct cgggaaggga gccgtccctg gagcagtgcc
tgcacaggtc ctgggctac cacaactgta accacagaga ggatgtgget
gtggtctgtg aagaacagca gtctggccta actgatgctt gacccacgg
cccaagcgc tcttacttct cctgggccct gatcggcccg gcctga
``` cat human mouse dog

Fig. 40

```
       H  MALLFSLILAI-CTRPGFLA--SPSG              * H=C=M
(LTS)  C  MALLFSLILAI-YTGPGILG--SFSK              . H=C
       M  MAPLFNLMLAILSIFVGSCFSESPTK              : H=M
          **,**,*,***  . .* . *;.

H  VRLVGGLHRCEGRVEVEQKGQWGTVCDDGWDIKDVAVLCRELGCGAASGTPSGILYEE
       C  VRLVGGDHRCEGRVELQQDDEWVTVCDDYWMMDSVAVLCRELGCGAARKTMSGTVYGP
       M  VQLVGGAIRCEGRVEVEHNGQWGTVCDDGWDRRDVAVVCRELNCGAVIQTPRGASYQF
(SRCR1)   *,****,*********;;. ;;*;*****;*;. ;***,****,***. *;,* * *

H  PAEKEQKVLIQSVSCTGTEDTLAQCEQEEVYD-CSHDEDAGASCE  NPESSFCPV-PEG
       C  YTPKDQKVFIHLFRCNGIEESLSQCEREDAIG-CSHVEDAGAVCE  PIYTGPGILGPES
       M  PAS-EQRVLIQGVLCNGTEDTLAQCELNYYVEDCSHEEDAGACCE  NFDSDLLFI-PED
          ;;. ;;*,* *;  ; * *;*;;*;*** .    *** ***** ** ;; ;    *+

H  VRLADGPGHCKGRVEVKHQNQWYTVCQTGWSLRAAKVVCRQLGCGRAVLTQKRCNKTA
       C  VRLADGPGRCQGRVEVKFRGEWSSVCQAGWSFAAAKVVCRQLGCGRATLTRRGCNKAT
(SRCR2) M  VRLVDGPGHCQGRVEVLHQSQWSTVCKAGWNLQVSKVVCRQLGCGRALLTYGSCNKNT
          ***,*****;* *****,;;. ;* ;**. **.; ..*********** ** ***

H  YGRKPIWLSQMSCSGREATLQDCPSGFWGKNTCNHDEDTWVECE  DPFD
       C  QGQGAIWQRKASCSGQEVSLQDCLSEVWEHN-CTHNEDVVVECE  DPFA
       M  QGKGPIWMGKMSCSGQEANLRSCLLSRLENN-CTHGEDTWNECE  DPFE
          * ;**   ;****. *; *..* . . * * **,*,*** ***

H  LRLVGGDNLCSGRLEVLHKGVWGSVCDDNWGEKEDQVVCKQLGCGKSLSPSFRDKCY
       C  LKLVGGRSHCEGRLEVLHKGEWGSVCDDGWGQDADRVVCRQLGCGQFLSPPVKVRRRF
       M  LKLVGGDTPCSGRLEVLHKGSWGSVCDDNWGEKEDQVVCKQLGCGKSLHPSPKTRKI
(SRCR3)   * ****. ;*,******* ******;;. ;*;***;*****;* *. .*; *; ;

H  GPGVGRIWLDNVRCSGEEQSLEQCQHRFWGFHDCTHQEDVAVICS.G
       C  GFGVGRIWLDDVKCSGKEPSLEQCLHRSWGYHNCNHREDVAVVCE  EQQSGLPDA
       M  GPGAGRIWLDDVNCSGKEQSLEFCRHRLWGYHDCTHKEDVEVICT  DFDV
          ***,****** * *** *;*,**,* .** ** *;*;* ***,*;*
```

Fig. 41

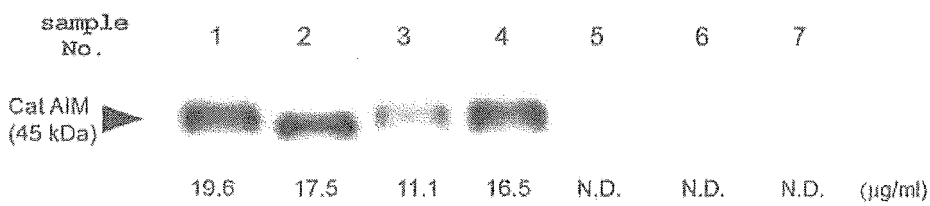

```
sample
No.       1     2     3     4     5     6     7

Cat AIM ▶  ▬▬   ▬▬   ▬    ▬▬
(45 kDa)

19.6  17.5  11.1  16.5  N.D.  N.D.  N.D.  (μg/ml)
``` mean serum AIM concentration in AIM+(total 48 samples): 16.8 μg/m
(mean of mouse・human AIM: 5 μg/m)

arrowhead: dead cell mass in proximal renal tubule (intraluminal debris)

PREVENTIVE OR THERAPEUTIC AGENT FOR KIDNEY DISEASE

CROSS-REFERENCE TO RELATED APPLICATIONS

This patent application is the U.S. national phase of International Patent Application No. PCT/JP2015/053415, filed on Feb. 6, 2015, which claims the benefit of Japanese Patent Application No. 2014-022041, filed Feb. 7, 2014, the disclosures of which are incorporated herein by reference in their entireties for all purposes.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 13,984 bytes ASCII (Text) file named "726214SequenceListing.txt," created Aug. 4, 2016.

TECHNICAL FIELD

The present invention relates to a prophylactic or therapeutic agent for kidney diseases and the like.

BACKGROUND ART

The number of patients with kidney disease is increasing along with increasing lifestyle-related diseases such as hypertension, diabetes, lipid abnormality and the like and metabolic syndrome due to changes in the life environment in recent years, and one out of about eight adults in Japan is considered to be a patient with chronic kidney disease. As a result of the progression of kidney disease, when the function of the kidney decreases to develop renal failure, kidney dialysis and kidney transplantation become necessary, which forms serious problems for the QOL of patients and medical economy. Moreover, acute renal failure (or acute renopathy) is a disease caused by various etiologies such as kidney ischemia, nephrotoxic toxin, sepsis and the like, with a high rate of long-term hospitalization and high mortality, and the incidence thereof is rather increasing in recent years. It is known that, in quite a few cases, acute renal failure does not cure sufficiently, becomes chronic, and turns into chronic renal failure.

As a treatment method of chronic kidney disease, drug therapy, diet therapy and rest treatment are performed. For example, drug therapy is performed using depressor, diuretic, active vitamin D formulation, oral carbonaceous adsorbent preparation, potassium adsorbent, phosphorus adsorbent and the like, aiming at delaying the progression of the disease, and improvement of symptoms associated with reduced kidney function. However, progression of the disease cannot be sufficiently stopped by any treatment method, and a new treatment method has been desired. In addition, a reliable treatment method of acute renal failure does not exist, and rapid development of the treatment method is demanded.

Also, kidney disease poses a serious problem in cats. Chronic renal failure is most frequently developed in aged cats, and renal failure is said to be the leading cause of death of aged cats. Almost all cats develop urinary tract calculus or urinary tract infection at the age of 6-7, which triggers degradation of kidney function, suffer from acute renal failure (or acute renopathy), and many of them develop chronic renal failure and die by the age of around 15. A satisfactory treatment method of kidney diseases in cats also does not exist, and a new treatment method has been requested.

AIM (apoptosis inhibitor of macrophage) is a factor specifically produced by a macrophage identified by the present inventor (non-patent document 1), which has been suggested to be related to some diseases. For example, due to obesity, the blood concentration of AIM increases, AIM is incorporated into adipocyte by endocytosis via CD36, and induces degradation of accumulated neutral fats (lipolysis), and therefore, the relationship with antiobesity has been suggested (non-patent document 2). AIM releases free fatty acid from the adipocyte by decomposition of neutral fats, and the released fatty acid induces and maintains chronic inflammation in adipose tissues via stimulation of a toll-like receptor. While metabolic syndrome is based on the acquisition of insulin resistance in obesity, since chronic inflammation in adipose tissue is important, AIM is considered to be related to metabolic syndrome (non-patent document 3). Furthermore, the present inventor clarified that an obese AIM KO mouse loaded with a high-calorie diet shows pathology similar to human NASH pathologies of obesity, fatty liver, liver parenchymal fibrosis and cancerogenesis, and reported the possibility of application of AIM to liver diseases (patent document 1). However, the relationship between AIM and kidney diseases has not been known to date.

DOCUMENT LIST

Patent Document patent document 1: WO 2013/162021

Non-Patent Documents non-patent document 1: Miyazaki, J Exp Med 189:413-422, 1999 non-patent document 2: Kurokawa, Cell Metab 11:479-492, 2010 non-patent document 3: Kurokawa, PNAS 108:12072-12077, 2011

SUMMARY OF THE INVENTION

Problems to be Solved by the Invention

The present invention aims to provide a prophylactic or therapeutic drug for kidney diseases. In addition, the present invention aims to provide a new method for the evaluation of or screening for a prophylactic or therapeutic drug for kidney diseases, and the like, which uses a model mouse of kidney diseases. Furthermore, another object of the present invention is to provide a prediction method of the prognosis of kidney diseases.

Means of Solving the Problems

The present inventor monitored progression of the kidney of AIM knockout mouse that underwent unilateral ureteral obstruction (UUO), or transient kidney ischemia/reperfusion (IR; ischemia/reperfusion) after uninephrectomy, and obtained very interesting findings that acute renal failure first occurs and, with the lapse of days, symptoms observed in chronic kidney diseases such as accumulation of necrotic renal tubule cells and renal parenchymal fibrosis, and disintegration and fibrosis of glomerular structure follow. Also, in AIM knockout mouse that underwent bilateral transient kidney ischemia/reperfusion (IR; ischemia/reperfusion), acute renal failure occurred, and accumulation of necrotic renal tubule cells and rapid progression of renopathy associated therewith, and exacerbation of general conditions and high incidence of death were confirmed. In addition, when AIM was administered to the AIM knockout mouse, BUN value was improved, the kidney function was rapidly improved and, along therewith, systemic symptoms associated therewith and mortality were improved. Therefrom it is considered that supplementation of AIM provides treatment of acute renal failure and prophylaxis or treatment of chronic kidney diseases.

The present inventors have conducted further investigations based on these findings, and completed the present invention.

Therefore, the present invention provides

[1] a prophylactic or therapeutic agent for a kidney disease, comprising AIM or a partial peptide thereof, or a nucleic acid comprising a base sequence encoding the same;

[2] a prophylactic or therapeutic agent for a kidney disease, comprising a drug that induces expression of AIM or a drug that stabilizes AIM;

[3] the agent of the aforementioned [1] or [2], wherein the kidney diseases is acute renal failure, chronic nephritis, chronic renal failure, nephrotic syndrome, diabetic nephropathy, nephrosclerosis, IgA nephropathy, hypertensive nephropathy, nephropathy associated with a collagen disease or IgM nephropathy;

[4] the agent of any one of the aforementioned [1]-[3], wherein the kidney disease is acute renal failure or chronic renal failure;

[5] the agent of any one of the aforementioned [1]-[4], wherein the subject of prophylaxis or treatment is a human;

[6] the agent of any one of the aforementioned [1]-[4], wherein the subject of prophylaxis or treatment is a cat;

[7] the agent of the aforementioned [6], wherein the AIM or a partial peptide thereof binds to cat IgM;

[8] the agent of the aforementioned [7], wherein the AIM that binds to cat IgM or a partial peptide thereof contains an SRCR3 domain of mouse-derived AIM;

[9] a screening method for a prophylactic or therapeutic agent for a kidney disease, comprising using an animal obtained by subjecting a non-human mammal deficient in AIM expression to unilateral ureteral obstruction, transient kidney ischemia/reperfusion after uninephrectomy or bilateral transient kidney ischemia/reperfusion;

[10] the method of the aforementioned [9], comprising the following steps:
(1) a step of administering, under conditions performing unilateral ureteral obstruction, transient kidney ischemia/reperfusion after uninephrectomy or bilateral transient kidney ischemia/reperfusion, a test substance to a non-human mammal deficient in AIM expression,
(2) a step of observing any one or more items of the following properties of the non-human mammal deficient in AIM expression, which is administered with the test substance:
(i) accumulation of necrotic renal tubule cells and renal parenchymal fibrosis,
(ii) disintegration and fibrosis of glomerular structure,
(iii) expression level of inflammatory cytokine in the kidney,
(iv) ratio of macrophage in the kidney,
(v) BUN value,
(vi) survival rate,
(3) a step of selecting a test substance that improves any one or more items of the aforementioned properties by comparison with those in the case of non-administration of the test substance;

[11] the screening method of the aforementioned [9] or [10], wherein the kidney disease is acute renal failure, chronic nephritis, chronic renal failure, nephrotic syndrome, diabetic nephropathy, nephrosclerosis, IgA nephropathy, hypertensive nephropathy, nephropathy associated with a collagen disease or IgM nephropathy;

[12] an evaluation method of a prophylactic or therapeutic effect of a prophylactic or therapeutic agent for kidney diseases, comprising using an animal obtained by subjecting a non-human mammal deficient in AIM expression to unilateral ureteral obstruction, transient kidney ischemia/reperfusion after uninephrectomy or bilateral transient kidney ischemia/reperfusion;

[13] the evaluation method of the aforementioned [12], comprising the following steps:
(1) a step of administering, under conditions performing unilateral ureteral obstruction, transient kidney ischemia/reperfusion after uninephrectomy or bilateral transient kidney ischemia/reperfusion, a prophylactic or therapeutic agent for kidney diseases to a non-human mammal deficient in AIM expression,
(2) a step of observing any one or more items of the following properties of the non-human mammal deficient in AIM expression, which is administered with the prophylactic or therapeutic agent for a kidney disease:
(i) accumulation of necrotic renal tubule cells and renal parenchymal fibrosis,
(ii) disintegration and fibrosis of glomerular structure,
(iii) expression level of inflammatory cytokine in the kidney,
(iv) ratio of macrophage in the kidney,
(v) BUN value,
(vi) survival rate,
(3) a step of evaluating an effect of a prophylactic or therapeutic agent for kidney diseases by comparison of any one or more items of the aforementioned properties with those in the case of non-administration of the prophylactic or therapeutic agent for kidney diseases;

[14] the evaluation method of the aforementioned [12] or [13], wherein the kidney disease is acute renal failure, chronic nephritis, chronic renal failure, nephrotic syndrome, diabetic nephropathy, nephrosclerosis, IgA nephropathy, hypertensive nephropathy, nephropathy associated with a collagen disease or IgM nephropathy;

[15] a method of predicting prognosis of a patient with a kidney disease, comprising measuring a concentration of AIM in a sample of a subject;

[16] the method of the aforementioned [15], wherein the sample is blood or serum;

[17] the method of the aforementioned [15] or [16], wherein a measurement method of the AIM concentration is an immunological method using an anti-AIM antibody;

[18] the method of any one of the aforementioned [15]-[17], wherein the kidney disease is acute renal failure, chronic nephritis, chronic renal failure, nephrotic syndrome, diabetic nephropathy, nephrosclerosis, IgA nephropathy, hypertensive nephropathy, nephropathy associated with a collagen disease or IgM nephropathy;

[19] a test method of acute renal failure, comprising measuring a concentration of AIM in a sample of a subject;

[20] the test method of [19], wherein the sample is urine;

[21] the test method of [19] or [20], wherein the measurement method of the AIM concentration is an immunological method using an anti-AIM antibody;

[22] A kit for the diagnosis of or prognosis prediction of a kidney disease, comprising the following (a) or (b):
(a) a nucleic acid probe or nucleic acid primer hybridizable with a transcription product of AIM gene, and/or
(b) antibody to AIM;
[23] the kit of [22], wherein the kidney disease is acute renal failure, chronic nephritis, chronic renal failure, nephrotic syndrome, diabetic nephropathy, nephrosclerosis, IgA nephropathy, hypertensive nephropathy, nephropathy associated with a collagen disease or IgM nephropathy;
[24] a method for the prophylaxis or treatment of a kidney disease, comprising administering an effective amount of AIM or a partial peptide thereof, or a nucleic acid comprising a base sequence encoding the same to a subject;
[25] a method for the prophylaxis or treatment of a kidney disease, comprising administering an effective amount of a drug that induces AIM expression or a drug that stabilizes AIM to a subject;
[26] the method of the aforementioned [24] or [25], wherein the kidney disease is acute renal failure, chronic nephritis, chronic renal failure, nephrotic syndrome, diabetic nephropathy, nephrosclerosis, IgA nephropathy, hypertensive nephropathy, nephropathy associated with a collagen disease or IgM nephropathy;
[27] the method of any one of the aforementioned [24]-[26], wherein the kidney disease is acute renal failure or chronic renal failure;
[28] the method of any one of the aforementioned [24]-[27], wherein the subject of prophylaxis or treatment is a human;
[29] the method of any one of the aforementioned [24]-[27], wherein the subject of prophylaxis or treatment is a cat;
[30] the method of the aforementioned [29] wherein the AIM or a partial peptide thereof binds to cat IgM;
[31] AIM or a partial peptide thereof, or a nucleic acid comprising a base sequence encoding the same, for use in the prophylaxis or treatment of a kidney disease;
[32] the AIM or a partial peptide thereof or a nucleic acid comprising a base sequence encoding the same of the aforementioned [31], wherein the kidney disease is acute renal failure, chronic nephritis, chronic renal failure, nephrotic syndrome, diabetic nephropathy, nephrosclerosis, IgA nephropathy, hypertensive nephropathy, nephropathy associated with a collagen disease or IgM nephropathy;
[33] the AIM or a partial peptide thereof or a nucleic acid comprising a base sequence encoding the same of the aforementioned [31] or [32], wherein the kidney disease is acute renal failure or chronic renal failure;
[34] the AIM or a partial peptide thereof or a nucleic acid comprising a base sequence encoding the same of any one of the aforementioned [31]-[33], wherein the subject of prophylaxis or treatment is a human;
[35] the AIM or a partial peptide thereof or a nucleic acid comprising a base sequence encoding the same of any one of the aforementioned [31]-[33], wherein the subject of prophylaxis or treatment is a cat;
[36] the AIM or a partial peptide thereof or a nucleic acid comprising a base sequence encoding the same of the aforementioned [35], wherein the AIM or a partial peptide thereof binds to cat IgM;
[37] a drug that induces AIM expression or a drug that stabilizes AIM, for use in the prophylaxis or treatment of a kidney disease;
[38] the drug that induces AIM expression or the drug that stabilizes AIM of the aforementioned [37], wherein the kidney disease is acute renal failure, chronic nephritis, chronic renal failure, nephrotic syndrome, diabetic nephropathy, nephrosclerosis, IgA nephropathy, hypertensive nephropathy, nephropathy associated with a collagen disease or IgM nephropathy;
[39] the drug that induces expression of AIM or the drug that stabilizes AIM of the aforementioned [37] or [38], wherein the kidney disease is acute renal failure or chronic renal failure;
[40] the drug that induces expression of AIM or the drug that stabilizes AIM of any one of the aforementioned [37]-[39], wherein the subject of prophylaxis or treatment is a human;
[41] the drug that induces expression of AIM or the drug that stabilizes AIM of any one of the aforementioned [37]-[39], wherein the subject of prophylaxis or treatment is a cat;
[42] the drug that induces expression of AIM or the drug that stabilizes AIM of the aforementioned [41], wherein the AIM or a partial peptide thereof binds to cat IgM;
[43] use of AIM or a partial peptide thereof or a nucleic acid comprising a base sequence encoding the same or a drug that induces expression of AIM or a drug that stabilizes AIM, which is for the production of a prophylactic or therapeutic agent for a kidney disease;
[44] the use of the aforementioned [43], wherein the kidney disease is acute renal failure, chronic nephritis, chronic renal failure, nephrotic syndrome, diabetic nephropathy, nephrosclerosis, IgA nephropathy, hypertensive nephropathy, nephropathy associated with a collagen disease or IgM nephropathy;
[45] the use of the aforementioned [43] or [44], wherein the kidney disease is acute renal failure or chronic renal failure;
[46] the use of any one of the aforementioned [43]-[45], wherein the subject of prophylaxis or treatment is a human;
[47] the use of any one of the aforementioned [43]-[45], wherein the subject of prophylaxis or treatment is a cat;
[48] the use of the aforementioned [47], wherein the AIM or a partial peptide thereof binds to cat IgM.

Effect of the Invention

The present invention can provide a prophylactic or therapeutic agent for a kidney disease, comprising AIM and the like as an active ingredient. In addition, according to the screening method using a kidney disease model mouse of the present invention, a substance effective to the prophylaxis or treatment for kidney diseases can be explored. In addition, using the kidney disease model mouse of the present invention, effects of a known prophylactic or therapeutic agent for a kidney disease can be evaluated. Furthermore, the present invention can provide a prediction method of prognosis and a test method of a kidney disease, which include measuring AIM concentration in a sample of a test subject.

BRIEF DESCRIPTION OF THE DRAWINGS

FIG. 1 shows A: Azan and hematoxylin simultaneous staining images of normal kidney tissue sections and kidney tissue sections after UUO of AIM KO mouse and WT mouse that underwent unilateral ureteral obstruction, B: Simultaneous Azan, PAS and hematoxylin staining images of normal kidney tissue sections and kidney tissue sections after UUO of AIM KO mouse and WT mouse that underwent unilateral ureteral obstruction.
FIG. 2 shows hematoxylin-eosin staining images of kidney tissue sections of AIM KO mouse and WT mouse that underwent transient kidney ischemia/reperfusion after uninephrectomy.

FIG. 3 shows A: F4/80 immunostaining images of kidney tissue sections of AIM KO mouse and WT mouse that underwent transient kidney ischemia/reperfusion after uninephrectomy, B: a graph showing the MCP-1 expression level of kidney tissue sections of AIM KO mouse and WT mouse that underwent transient kidney ischemia/reperfusion after uninephrectomy. *: P<0.05, **: P<0.01

FIG. 32 shows A: Western blot images of AIM present in the sera of dog (n=3), cat (n=3) and mouse, B: Western blot images of rAIM in the cat and mouse.

FIG. 33 shows A: Western blot images for AIM and IgM on each size fraction of serum derived from cat intravenously injected with recombinant cat AIM (1 mg), B: Western blot images for AIM and IgM on each size fraction of serum derived from mouse.

FIG. 34 shows Western blot images for AIM and IgM on each size fraction of serum derived from cat intravenously injected with recombinant mouse AIM (1 mg).

FIG. 35 shows cat AIM cDNA sequence (SEQ ID NO: 5) wherein translational initiation site (atg) and translational termination site (tga) in bold, non-coding sequence is shown in an oblique font, a base sequence encoding leader peptide is shown with a solid line, and further, base sequence encoding hinge region between SRCR1 and SRCR2, hinge region between SRCR2 and SRCR3, and peptide sequence between SRCR3 and translational termination site is underlined with a broken line.

FIG. 40 shows comparison of leader peptides (LSs) and the amino acid sequences of each SRCR and hinge region of human (SEQ ID NO: 2), cat (SEQ ID NO: 4) and mouse (SEQ ID NO: 6).

FIG. 41 shows reduced Western blotting images of AIM in the serum of cat by using an anti-cat AIM monoclonal antibody wherein individuals 1-4 are individuals detected with AIM and AIM value was calculated by comparison to the intensity of the signal of rcAIM of control, and individuals 5-7 were individuals not detected with AIM signal (N.D.: not detectable).

DESCRIPTION OF EMBODIMENTS

Figure 4:
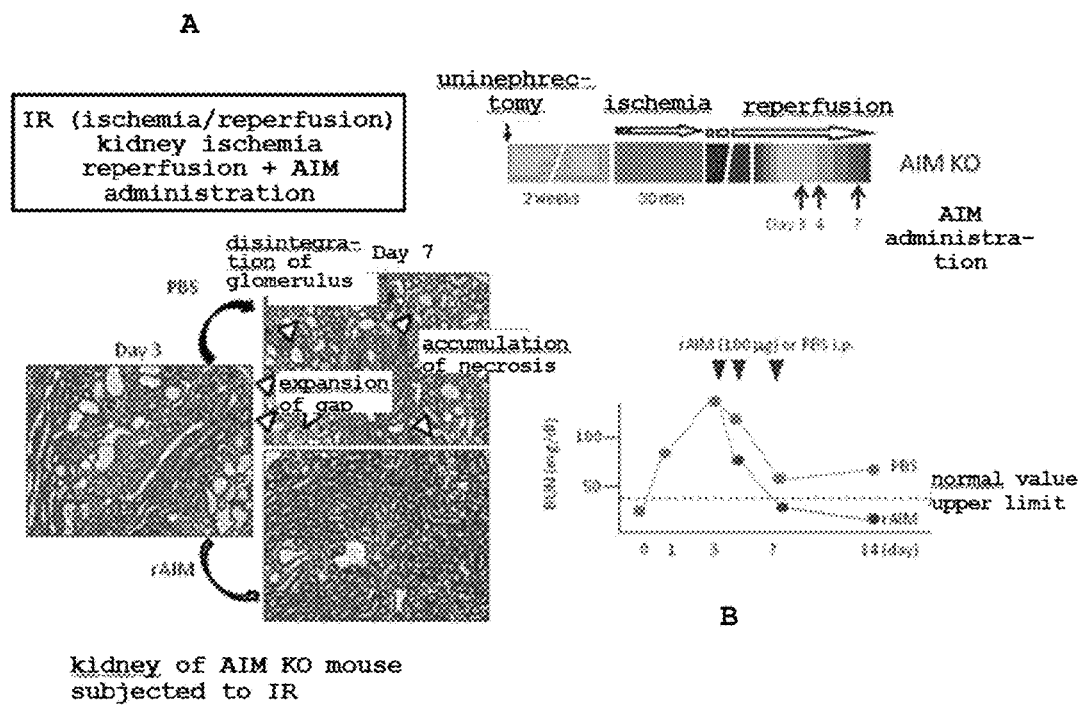
FIG. 4 shows A: hematoxylin-eosin staining images of kidney tissue sections of AIM KO mouse that underwent transient kidney ischemia/reperfusion after uninephrectomy and administration of rAIM or PBS, B: BUN value of AIM KO mouse and WT mouse that underwent transient kidney ischemia/reperfusion after uninephrectomy and administration of rAIM or PBS.

The present invention provides a prophylactic or therapeutic agent for a kidney disease comprising AIM or a partial peptide thereof, or a nucleic acid comprising a base sequence encoding the same.

AIM in the present invention is a protein containing an amino acid sequence that is the same or substantially the same as the amino acid sequence shown in SEQ ID NO: 2 (amino acid sequence of human-derived AIM protein) or SEQ ID NO: 4 (amino acid sequence of cat-derived AIM protein).

AIM may be, for example, a protein isolated and purified from macrophage, which is immunocyte of warm-blooded animals (e.g., human, mouse, rat, rabbit, sheep, swine, bovine, horse, cat, dog, monkey, chimpanzee, chicken and the like). It may also be a protein chemically synthesized or biochemically synthesized in a cell-free translation system. Alternatively, the protein may be a recombinant protein produced from a transformant incorporating a nucleic acid comprising a base sequence that encodes the above-described amino acid sequence.

Substantially the same amino acid sequence as the amino acid sequence shown in SEQ ID NO:2 or SEQ ID NO:4 refers to an amino acid sequence having a homology of about 60% or more, preferably about 70% or more, further preferably about 80% or more, particularly preferably about 90% or more, most preferably about 95% or more, to the amino acid sequence shown in SEQ ID NO:2 or SEQ ID NO:4, and the like. Here, "a homology" means a ratio (%) of identical amino acid residues and similar amino acid residues to all overlapping amino acid residues in the optimal alignment (preferably, the algorithm considers introduction of gaps on one or both sides of the sequence for the best alignment) where two amino acid sequences are aligned using a mathematical algorithm known in the technical field. "Similar amino acid" means an amino acid having similar physiochemical properties; examples thereof include amino acids classified under the same group, such as aromatic amino acids (Phe, Trp, Tyr), aliphatic amino acids (Ala, Leu, Ile, Val), polar amino acids (Gln, Asn), basic amino acids (Lys, Arg, His), acidic amino acids (Glu, Asp), amino acids having a hydroxyl group (Ser, Thr) and amino acids having a small side-chain (Gly, Ala, Ser, Thr, Met). Substitution by such similar amino acids is expected not to change the phenotype of proteins (i.e., conservative amino acid substitution). Specific examples of the conservative amino acid substitution are known in the technical field and are described in various documents (see, for example, Bowie et al., Science, 247:1306-1310 (1990)).

Amino acid sequence homology in the present description can be calculated using the homology calculation algorithm NCBI BLAST (National Center for Biotechnology Information Basic Local Alignment Search Tool) under the following conditions (expectancy=10; gaps allowed; matrix=BLOSUM62; filtering=OFF). As examples of other algorithms for determination of amino acid sequence homology, the algorithm described in Karlin et al., Proc. Natl. Acad. Sci. USA, 90:5873-5877 (1993) [the algorithm is incorporated in the NBLAST and XBLAST programs (version 2.0) (Altschul et al., Nucleic Acids Res., 25:3389-3402 (1997))], the algorithm described in Needleman et al., J. Mol. Biol., 48:444-453 (1970) [the algorithm is incorporated in the GAP program in the GCG software package], the algorithm described in Myers and Miller, CABIOS, 4:11-17 (1988) [the algorithm is incorporated in the ALIGN program (version 2.0), which is part of the CGC sequence alignment software package], the algorithm described in Pearson et al., Proc. Natl. Acad. Sci. USA, 85:2444-2448 (1988) [the algorithm is incorporated in the FASTA program in the GCG software package] and the like can be mentioned, which can likewise be used preferably.

More preferably, substantially the same amino acid sequence as the amino acid sequence shown in SEQ ID NO:2 or SEQ ID NO:4 is an amino acid sequence having an identity of about 60% or more, preferably about 70% or more, further preferably about 80% or more, particularly preferably about 90% or more, and most preferably about 95% or more, to the amino acid sequence shown in SEQ ID NO:2 or SEQ ID NO:4.

As a protein comprising substantially the same amino acid sequence as the amino acid sequence shown in SEQ ID NO:2 or SEQ ID NO:4, for example, a protein comprising substantially the same amino acid sequence as the aforementioned amino acid sequence shown in SEQ ID NO:2 or SEQ ID NO:4, and having an activity of substantially the same quality as that of a protein comprising the amino acid sequence shown in SEQ ID NO:2 or SEQ ID NO:4 and the like are preferable. Here, the "activity" refers to, for example, an activity to suppress apoptosis of macrophage in atherosclerotic plaque, an activity to maintain or promote arteriosclerosis, an adipocyte differentiation suppressive activity, activity to melt lipid droplet of adipocyte, adipocyte reducing activity, CD36 binding activity, endocytosis activity to adipocyte, FAS binding activity, FAS function suppressive activity, antiobesity activity or the like. "Substantially the same quality" means that the activity thereof is qualitatively (e.g., physiologically or pharmacologically) the same. Therefore, it is preferable that the aforementioned activities be equivalent to each other, but the quantitative factors of these activities, such as the extent of activity (e.g., about 0.1 to about 10 times, preferably about 0.5 to about 2 times) and the molecular weight of the protein, may be different.

The aforementioned activities can be measured by a method known per se.

Examples of the AIM in the present invention also include proteins comprising (1) an amino acid sequence having 1 or 2 or more (preferably about 1 to 100, preferably about 1 to 50, further preferably about 1 to 10, particularly preferably 1 to several (2, 3, 4 or 5)) amino acids deleted from the amino acid sequence shown in SEQ ID NO:2 or SEQ ID NO:4, (2) an amino acid sequence having 1 or 2 or more (preferably about 1 to 100, preferably about 1 to 50, further preferably about 1 to 10, particularly preferably 1 to several (2, 3, 4 or 5)) amino acids added to the amino acid sequence shown in SEQ ID NO:2 or SEQ ID NO:4, (3) an amino acid sequence having 1 or 2 or more (preferably about 1 to 50, preferably about 1 to 10, further preferably 1 to several (2, 3, 4 or 5)) amino acids inserted in the amino acid sequence shown in SEQ ID NO:2 or SEQ ID NO:4, (4) an amino acid sequence having 1 or 2 or more (preferably about 1 to 50, preferably about 1 to 10, further preferably 1 to several (2, 3, 4 or 5)) amino acids substituted by other amino acids in the amino acid sequence shown in SEQ ID NO:2 or SEQ ID NO:4, or (5) an amino acid sequence comprising a combination thereof.

When an amino acid sequence has been inserted, deleted or substituted as described above, the position of the insertion, deletion or substitution is not particularly limited, as far as the activity of the protein is maintained.

AIM in the present invention is preferably a human AIM protein having the amino acid sequence shown in SEQ ID NO:2 (GenBank Accession No.: AAD01446), or a cat AIM protein having the amino acid sequence shown in SEQ ID NO: 4 or a homologue thereof in other mammals [for example, mouse homologue registered in the GenBank as Accession No.: AAD01445 and the like], more preferably, a human AIM protein consisting of the amino acid sequence shown in SEQ ID NO:2 or a cat AIM protein consisting of the amino acid sequence shown in SEQ ID NO: 4.

In the present specification, the protein and peptide are described according to the common practice of peptide designation, wherein the left end indicates the N-terminus (amino terminus) and the right end indicates the C-terminus (carboxyl terminus). In AIM of the present invention including a protein comprising the amino acid sequence shown in SEQ ID NO:2 or SEQ ID NO:4, the C-terminus may be any of a carboxyl group (—COOH), carboxylate (—COO⁻), amide (—CONH$_2$) and ester (—COOR).

Here, as R in the ester, a $C_{1-6}$ alkyl group, for example, methyl, ethyl, n-propyl, isopropyl and n-butyl, a $C_{3-8}$ cycloalkyl group, for example, cyclopentyl and cyclohexyl, a $C_{6-12}$ aryl group, for example, phenyl and α-naphthyl, a phenyl-$C_{1-2}$ alkyl group, for example, benzyl and phenethyl, a $C_{7-14}$ aralkyl group, for example, an α-naphthyl-$C_{1-2}$ alkyl group, for example, α-naphthylmethyl, a pivaloyloxymethyl group; and the like can be used.

When the AIM of the present invention has a carboxyl group (or carboxylate) at a position other than the C-terminus, a protein wherein the carboxyl group is amidated or esterified is also included in the protein of the present invention. In this case, as the ester, the above-described ester at the C terminus, and the like, for example, are used.

Furthermore, the AIM of in the present invention also includes a protein wherein the amino group of the N-terminus amino acid residue is protected by a protecting group (e.g., $C_{1-6}$ acyl groups such as $C_{1-6}$ alkanoyls such as formyl group and acetyl group, and the like); a protein wherein the glutamine residue that may be produced upon cleavage at the N terminus in vivo has been converted to pyroglutamic acid, a protein wherein a substituent (e.g., —OH, —SH, amino group, imidazole group, indol group, guanidino group and the like) on a side chain of an amino acid in the molecule is protected by an appropriate protecting group (e.g., $C_{1-6}$ acyl groups such as $C_{1-6}$ alkanoyl groups such as formyl group and acetyl group, and the like), a conjugated peptide such as what is called a glycopeptide having a sugar chain bound thereto, and the like.

The partial peptide of AIM (hereinafter sometimes to be abbreviated simply as "the partial peptide of the present invention") may be any as long as it is a peptide having the above-mentioned partial amino acid sequence of AIM, and having an activity of substantially the same quality as AIM. Here, the "activity of substantially the same quality" is as defined above. In addition, the "activity of substantially the same quality" can be measured in the same manner as in the case of AIM.

Since AIM comprises 3 SRCR (Scavenger-Receptor Cysteine-Rich) domains comprising a large amount of cysteine, the respective SRCR domains can be used as the partial peptide of the present invention. To be specific, for example, of the amino acid sequence shown in SEQ ID NO:2, partial amino acid sequences respectively comprising SRCR1 domain (amino acid Nos. 24-125 of the amino acid sequence shown in SEQ ID NO:2), SRCR2 domain (amino acid Nos. 138-239 of the amino acid sequence shown in SEQ ID NO:2), and SRCR3 domain (amino acid Nos. 244-346 of the amino acid sequence shown in SEQ ID NO:2), partial amino acid sequence comprising any combination of SRCR domains and the like can be used. In addition, of the amino acid sequence shown in SEQ ID NO:4, partial amino acid sequences respectively comprising SRCR1 domain (amino acid Nos. 24-125 of the amino acid sequence shown in SEQ ID NO:4), SRCR2 domain (amino acid Nos. 139-239 of the amino acid sequence shown in SEQ ID NO:4), and SRCR3 domain (amino acid Nos. 244-346 of the amino acid sequence shown in SEQ ID NO:4), partial amino acid sequence comprising any combination of SRCR domains and the like can also be used. The size of the partial peptide of the present invention is not particularly limited as long as it comprises the above-mentioned functional domain. The partial peptide preferably comprises not less than 50 partial amino acid sequences, more preferably not less than 100 partial amino acid sequences, further preferably not less than 200 partial amino acid sequences. The partial amino acid sequences may be a single consecutive partial amino acid sequence, or discontinuous plural partial amino acid sequences linked to each other.

In addition, the C-terminus of the partial peptide of the present invention may be any of a carboxyl group (—COOH), carboxylate (—COO⁻), amide (—CONH$_2$) and ester (—COOR). Here, examples of the R in ester include, those similar to the examples recited above for AIM. When the partial peptide of the present invention has a carboxyl group (or carboxylate) at a position other than the C-terminus, the carboxyl group may be amidated or esterified, which is also encompassed in the partial peptide of the present invention. As the ester in this case, for example, those similar to the ester at the C-terminus and the like are used.

Furthermore, the partial peptide of the present invention includes, in the same manner as in the above-mentioned AIM, the amino group of the N-terminus amino acid residue may be protected with a protecting group, the glutamine residue at the N-terminus may be converted to pyroglutamic acid, a substituent on the side chain of the amino acid in a molecule may be protected with a suitable protecting group, or the partial peptide may be a composite peptide wherein a sugar chain is bonded (so-called glycopeptide and the like), and the like.

AIM or a partial peptide thereof to be used in the present invention may be in the form of a salt. For example, salts with physiologically acceptable acid (e.g., inorganic acid, organic acid), base (e.g., alkali metal salt) and the like are used, and physiologically acceptable acid addition salts are preferable. Useful salts include, for example, salts with inorganic acids (e.g., hydrochloric acid, phosphoric acid, hydrobromic acid, sulfuric acid) or salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

AIM can be produced from a macrophage of the aforementioned mammals by a protein purification method known per se. To be specific, AIM or a salt thereof can be prepared by homogenizing mammalian macrophage, removing cell debris by low-speed centrifugation, centrifuging the supernatant at a high speed to precipitate a cellular membrane-comprising fraction, and subjecting the supernatant to chromatography such as reversed-phase chromatography, ion exchange chromatography, affinity chromatography and the like, and the like.

AIM or a partial peptide thereof can also be produced according to a publicly known method of peptide synthesis (hereinafter full-length AIM and a partial peptide thereof are comprehensively referred simply to as AIM in the explanation of the chemical synthesis thereof, unless otherwise specified).

The method of peptide synthesis may be any of, for example, a solid phase synthesis process and a liquid phase synthesis process. A desired protein can be produced by condensing a partial peptide or amino acid capable of constituting AIM with the remaining portion, and removing any protecting group the resultant product may have.

Here, the condensation and the protecting group removal are conducted in accordance with methods known per se, for example, the methods indicated in (1) and (2) below:
(1) M. Bodanszky and M. A. Ondetti: *Peptide Synthesis*, Interscience Publishers, New York (1966)
(2) Schroeder and Luebke: *The Peptide*, Academic Press, New York (1965).

AIM thus obtained can be purified or isolated by a known method of purification. Here, as examples of the method of purification, solvent extraction, distillation, column chromatography, liquid chromatography, recrystallization, combinations thereof and the like can be mentioned.

When thus obtained AIM is in a free form, the free form can be converted into a suitable salt form by a known method or an analogue thereto, and on the other hand, when the AIM is obtained in the form of a salt, it can be converted into the free form or in the form of a different salt by a known method or a method based thereon.

Furthermore, AIM can also be produced by culturing a transformant comprising a nucleic acid encoding the same, and separating and purifying AIM from the obtained culture. The nucleic acid encoding AIM or a partial peptide thereof may be DNA or RNA, or DNA/RNA chimera, preferably DNA. Additionally, the nucleic acid may be double-stranded or single-stranded. In the case of a double-stranded nucleic acid, it may be a double-stranded DNA, a double-stranded RNA, or a DNA:RNA hybrid. In the case of a single strand, it may be a sense strand (that is, coding strand), or an antisense strand (that is, non-coding strand).

Examples of the DNA encoding AIM or a partial peptide thereof include genomic DNA, cDNA derived from macrophage of warm-blooded animal (e.g., human, bovine, monkey, horse, swine, sheep, goat, dog, cat, guinea pig, rat, mouse, rabbit, hamster, chicken and the like), synthetic DNA and the like. Genomic DNA encoding AIM or a partial peptide thereof can be directly amplified by Polymerase Chain Reaction (hereinafter to be abbreviated as "PCR method") by using, as a template, a genomic DNA fraction prepared from any cell of the aforementioned animals [for example, hepatocyte, splenocyte, nerve cell, glial cell, pancreatic β cell, myelocyte, mesangial cell, Langerhans' cell, epidermal cell, epithelial cell, goblet cell, endothelial cell, smooth muscle cell, fibroblast, fibrocyte, myocyte, adipocyte, immunocyte (e.g., macrophage, T cell, B cell, natural killer cell, mast cell, neutrophil, basophil, eosinophil, monocyte), megakaryocyte, synovial cell, chondrocyte, bone cell, osteoblast, osteoclast, mammary gland cell, hepatocyte or interstitial cell, or corresponding progenitor cell, stem cell or cancer cell thereof, and the like], or any tissue where such cells are present [for example, brain or any portion of the brain (e.g., olfactory bulb, amygdaloid nucleus, basal ganglia, hippocampus, thalamus, hypothalamus, subthalamic nucleus, cerebral cortex, medulla oblongata, cerebellum), spinal cord, hypophysis, stomach, pancreas, kidney, liver, gonad, thyroid, gall-bladder, bone marrow, adrenal gland, skin, lung, gastrointestinal tract (e.g., large intestine, small intestine), blood vessel, heart, thymus, spleen, submandibular gland, peripheral blood, prostate, testicle, ovary, placenta, uterus, bone, joint, adipose tissue (e.g., brown adipose tissue, white adipose tissue), skeletal muscle and the like], and cDNA encoding AIM or a partial peptide thereof can also be directly amplified by PCR method and Reverse Transcriptase-PCR (hereinafter to be abbreviated as "RT-PCR method") by using, as a template, a total RNA or mRNA fraction prepared from macrophage, respectively. Alternatively, the genomic DNA and cDNA encoding AIM or a partial peptide thereof can also be cloned by colony or plaque hybridization method or PCR method and the like from a genomic DNA library and cDNA library prepared by inserting the above-mentioned genomic DNA and total RNA or a fragment of mRNA into a suitable vector. The vector used for the library may be any of a bacteriophage, a plasmid, a cosmid, a phagemid and the like.

Examples of the DNA encoding AIM include a DNA comprising the same or substantially the same base sequence as the base sequence shown in SEQ ID NO: 1 or SEQ ID NO: 3 and the like.

As the DNA comprising the same or substantially the same base sequence as the base sequence shown in SEQ ID NO: 1 or SEQ ID NO: 3, for example, a DNA comprising a base sequence having a homology of not less than about 60%, preferably not less than about 70%, more preferably not less than about 80%, particularly preferably not less than about 90%, with the base sequence shown in SEQ ID NO: 1, and encoding a protein having an activity of substantially the same quality as the aforementioned AIM and the like are used.

Base sequence homology in the present description can be calculated using the homology calculation algorithm NCBI BLAST (National Center for Biotechnology Information Basic Local Alignment Search Tool) under the following conditions (expectancy=10; gap allowed; filtering=ON; match score=1; mismatch score=−3). As preferable examples of other algorithms for determining base sequence homology, the above-described amino acid sequence homology calculation algorithm can also be mentioned.

The DNA encoding AIM is preferably a DNA comprising a base sequence encoding human AIM protein shown by the base sequence shown in SEQ ID NO: 1 (GenBank accession No: AF011429), or a DNA containing a base sequence encoding a cat AIM protein shown by the base sequence shown in SEQ ID NO: 3, or a homologue thereof in other mammal [for example, mouse homologue registered in GenBank as accession No: AF011428 and the like].

The DNA encoding the partial peptide of the present invention may be any as long as it comprises a base sequence encoding a peptide comprising the same or substantially the same amino acid sequence as a part of the amino acid sequence shown in SEQ ID NO:2 or SEQ ID NO:4. Specifically, as a DNA encoding the partial peptide of the present invention, (1) a DNA comprising a partial base sequence of the base sequence shown in SEQ ID NO: 1 or SEQ ID NO: 3, or (2) a DNA comprising a base sequence having a homology of not less than about 60%, preferably not less than about 70%, more preferably not less than about 80%, particularly preferably not less than about 90%, with a DNA comprising a partial base sequence of the base sequence shown in SEQ ID NO: 1 or SEQ ID NO: 3, and encoding a protein having an activity of substantially the same quality as the aforementioned AIM and the like are used.

A DNA encoding AIM or a partial peptide thereof can be cloned by amplifying same using a synthesized DNA primer having a part of a base sequence encoding the AIM or a partial peptide thereof by PCR method, or by conducting hybridization of a DNA incorporated into a suitable expression vector with a labeled DNA fragment or synthetic DNA encoding a part or whole region of AIM. Hybridization can be conducted according to a method known per se or a method based thereon, for example, a method described in Molecular Cloning, 2nd edition (J. Sambrook et al., Cold Spring Harbor Lab. Press, 1989) and the like. When a commercially available library is used, hybridization can be conducted according to the method described in the instruction manual attached thereto. Hybridization can preferably be conducted under highly stringent conditions.

As examples of the highly stringent conditions, conditions of a hybridization reaction in 6×SSC (sodium chloride/ sodium citrate) at 45° C. followed by washing in 0.2×SSC/ 0.1% SDS at 65° C. once or more and the like can be mentioned. Those skilled in the art are able to easily obtain desired stringency by changing the salt concentration of the hybridization solution, hybridization reaction temperature, probe concentration, probe length, the number of mismatches, hybridization reaction time, the salt concentration of the washing solution, washing temperature and the like as appropriate. When a commercially available library is used, hybridization can be conducted according to the method described in the instruction manual attached to the library.

An expression vector comprising DNA that encodes AIM or a partial peptide thereof can be produced by, for example, cutting out a desired DNA fragment from the DNA that encodes AIM, and joining the DNA fragment downstream of a promoter in an appropriate expression vector.

As the expression vector, plasmid derived from *Escherichia coli* (e.g., pBR322, pBR325, pUC12, pUC13); animal cell expression plasmid (e.g., pA1-11, pXT1, pRc/CMV, pRc/RSV, pcDNAI/Neo); animal virus vectors such as retrovirus, vaccinia virus, adenovirus and the like, and the like are used.

The promoter may be any promoter, as long as it is appropriate for the host used to express the gene.

For example, when the host is an animal cell, SRα promoter, SV40 promoter, LTR promoter, CMV (cytomegalovirus) promoter, RSV (Rous sarcoma virus) promoter, MoMuLV (Moloney murine leukemia virus) LTR, HSV-TK (simple herpes virus thymidine kinase) promoter and the like are used. Of these, CMV promoter, SRα promoter and the like are preferable.

When the host is a bacterium of the genus *Escherichia*, the trp promoter, the lac promoter, the recA promoter, the λP$_L$ promoter, the lpp promoter, the T7 promoter and the like are preferred.

Useful expression vectors include, in addition to the above, those optionally harboring an enhancer, a splicing signal, a polyA addition signal, a selection marker, an SV40 replication origin (hereinafter also abbreviated as SV40ori) and the like. As examples of the selection marker, the dihydrofolate reductase (hereinafter also abbreviated as dhfr) gene [methotrexate (MTX) resistance], the ampicillin resistance gene (hereinafter also abbreviated as Amp$^r$), the neomycin resistance gene (hereinafter also abbreviated as Neo$^r$, G418 resistance) and the like can be mentioned. In particular, when a Chinese hamster cell lacking the dhfr gene is used in combination with the dhfr gene as the selection marker, a target gene can also be selected using a thymidine-free medium.

Where necessary, a base sequence encoding a signal sequence suitable for a host (signal codon) may be added (or substituted with native signal codon) to the 5'-terminus side of a DNA encoding AIM or a partial peptide thereof. For example, when the host is the genus *Escherichia*, PhoA signal sequence, OmpA signal sequence and the like are used; when the host is an animal cell, insulin signal sequence, α-interferon signal sequence, antibody molecule signal sequence and the like are used.

AIM or a partial peptide thereof can be produced by transforming a host with an expression vector comprising the above-mentioned DNA encoding AIM or a partial peptide thereof, and cultivating the obtained transformant.

As the host, for example, the genus *Escherichia*, animal cell and the like are used.

As the genus *Escherichia*, for example, *Escherichia coli* K12.DH1 [Proc. Natl. Acad. Sci. USA), vol. 60, 160(1968)], *Escherichia coli* JM103 [Nucleic Acids Research, vol. 9, 309(1981)], *Escherichia coli* JA221 [Journal of Molecular Biology, vol. 120, 517(1978)], *Escherichia coli* HB101

[Journal of Molecular Biology, vol. 41, 459(1969)], *Escherichia coli* C600 [Genetics, vol. 39, 440(1954)] and the like are used.

As the animal cell, for example, monkey COS-7 cell, monkey Vero cell, Chinese hamster ovary cell (hereinafter to be abbreviated as CHO cell), dhfr gene-deficient CHO cell (hereinafter to be abbreviated as CHO(dhfr$^-$) cell), mouse L cell, mouse AtT-20 cell, mouse myeloma cell, ratGH3 cell, human FL cell and the like are used.

Transformation can be carried out according to the kind of host in accordance with a publicly known method.

The genus *Escherichia* can be transformed, for example, in accordance with the methods described in Proc. Natl. Acad. Sci. USA, vol. 69, 2110 (1972), Gene, vol. 17, 107 (1982) and the like.

An animal cell can be transformed, for example, in accordance with a method described in Saibo Kogaku (Cell Engineering), extra issue 8, Shin Saibo Kogaku Jikken Protocol (New Cell Engineering Experimental Protocol), 263-267 (1995), published by Shujunsha, or Virology, Vol. 52, 456 (1973).

Cultivation of a transformant can be carried out according to the kind of host in accordance with a publicly known method.

As an example of the medium used for culturing a transformant whose host is a bacterium of the genus *Escherichia*, an M9 medium supplemented with glucose and a casamino acid [Miller, Journal of Experiments in Molecular Genetics, 431-433, Cold Spring Harbor Laboratory, New York 1972] is preferable. As required, in order to increase promoter efficiency, a chemical agent such as 3β-indolylacrylic acid may be added to the medium.

Cultivation of a transformant whose host is a bacterium of the genus *Escherichia* is normally carried out at about 15° C. to about 43° C. for about 3 to about 24 hours. As necessary, the culture may be aerated or agitated.

Useful medium for cultivating a transformant whose host is an animal cell include, for example, minimum essential medium (MEM) comprising about 5-about 20% fetal bovine serum [Science, vol. 122, 501 (1952)], Dulbecco's modified Eagle medium (DMEM) [Virology, vol. 8, 396(1959)], RPMI1640 medium [The Journal of the American Medical Association, vol. 199, 519(1967)], 199 medium [Proceeding of the Society for the Biological Medicine, vol. 73, 1(1950)] and the like. The medium's pH is preferably about 6 to about 8. Cultivation is normally carried out at about 30° C. to about 40° C. for about 15 to about 60 hours. As necessary, the culture may be aerated or agitated.

As described above, AIM can be produced within or outside of a transformant cell.

AIM or a partial peptide thereof can be separated and purified from the culture obtained by cultivating the aforementioned transformant according to a method known per se.

For example, when AIM or a partial peptide thereof is extracted from a cultured bacterium or cytoplasm of cell, a method is used as appropriate wherein bacteria or cells are collected from a culture by a known means, suspended in an appropriate buffer solution, and disrupted by means of sonication, lysozyme and/or freeze-thawing and the like, after which a crude extract of soluble protein is obtained by centrifugation or filtration. The buffer solution may comprise a protein denaturant such as urea or guanidine hydrochloride and a surfactant such as Triton X-100™. In addition, when AIM or a partial peptide thereof is secreted outside the bacterium (cell), a method of separating a culture supernatant by centrifugation, filtration or the like from a culture, and the like are used.

Isolation and purification of AIM or a partial peptide thereof contained in the thus-obtained soluble fraction and culture supernatant can be conducted according to a method known per se. Useful methods include methods based on solubility, such as salting-out and solvent precipitation; methods based mainly on molecular weight differences, such as dialysis, ultrafiltration, gel filtration, and SDS-polyacrylamide gel electrophoresis; methods based on charge differences, such as ion exchange chromatography; methods based on specific affinity, such as affinity chromatography; methods based on hydrophobicity differences, such as reversed-phase high performance liquid chromatography; and methods based on isoelectric point differences, such as isoelectric focusing. These methods can be combined as appropriate.

The presence of the thus-obtained AIM or a partial peptide thereof can be confirmed by enzyme immunoassay, Western blotting and the like using an antibody against AIM.

AIM or a partial peptide thereof or a salt thereof or nucleic acid comprising a base sequence encoding AIM or a partial peptide thereof (sometimes to be indicated as AIMs here) obtained as mentioned above can be provided as an agent for the prophylaxis of the onset or the treatment of kidney diseases.

In the present invention, a drug that induces AIM expression and a drug that stabilizes AIM can also be used instead of the AIMs.

Examples of the drug that induces AIM expression include a compound having an AIM transcription activity and the like, and examples of the compound include a transcription factor capable of binding to promoter region of the AIM gene and the like. The present inventor has also found that AIM is expressed in macrophage. Therefore, as a drug that induces AIM expression, a macrophage differentiation-inducing factor can be mentioned. The macrophage differentiation-inducing factor is not particularly limited as long as it can induce differentiation of macrophage from progenitor cells such as granulocyte-macrophage colony forming cell (CFU-GM), macrophage colony forming cell (CFU-M) and the like, and, for example, granulocyte-macrophage colony stimulating factor (GM-CSF), macrophage colony stimulating factor (M-CSF) and the like can be used. The transcription factor, GM-CSF, M-CSF may be proteins isolated and purified from mammalian tissues and cells by the aforementioned known means, or may be proteins chemically synthesized or biochemically synthesized in a cell-free translation system. Alternatively, they may be recombinant proteins produced from transformants introduced with a nucleic acid comprising a base sequence encoding the above-mentioned proteins.

Examples of the drug that stabilizes AIM include a compound inhibiting degradation of AIM, a compound inhibiting excretion into urine and the like. Examples of the compound inhibiting degradation include protease inhibitor, proteasome inhibitor and the like. Examples of the protease inhibitor include serine protease inhibitor (4-(2-aminoethyl) benzenesulfonyl fluoride hydrochloride (AEBSGF), aprotinin, trypsin inhibitor and the like), cysteine protease inhibitor (E-64, leupeptin and the like) and the like. Examples of the proteasome inhibitor include lactacystin, MG-115, MG-132, proteasome inhibitor I and the like. Examples of the compound inhibiting excretion into urine include a compound that confers a molecular weight preventing passage through glomerular basement membrane on AIM. Since IgM binds to AIM (WO 2013/162021; Arai et al., Cell Reports 3: 1187-1198, 2013), IgM can be mentioned as a compound inhibiting excretion of AIM into urine. However, since administration of IgM per se is feared to cause side effects in the immune system, a fusion protein obtained by fusion of Fc fragment of IgM which is a binding site to AIM and a protein having a molecular weight of the level preventing filtration by renal tubule and excretion into urine is preferably used. While the protein to be fused is not limited, a protein with less fear of side effect is preferable and, for example, albumin can be used. The binding may be a direct one or via a hinge region. Examples of the hinge region include tandem FLAG tags. Such molecule can be produced as a single recombinant protein by linking genes encoding each by a conventional method. While AIM that binds to IgM may be derived from any warm-blooded animal, AIM derived from cat may be excluded.

In the below-mentioned Examples of the present invention, AIM knockout mouse showed the symptoms of kidney diseases under conditions performing unilateral ureteral obstruction, transient kidney ischemia/reperfusion after uni-nephrectomy or bilateral transient kidney ischemia/reperfusion. From the above, AIMs, a drug that induces the expression of AIM or a drug that stabilizes AIM, or a compound capable of substituting the function of AIM, which can be searched for by the below-mentioned screening method, is suggested to prevent the onset and progression of kidney diseases and treat kidney diseases.

The subject of the administration of a pharmaceutical composition containing AIMs, a drug that induces expression of AIM or a drug that stabilizes AIM of the present invention includes, for example, human and other warm-blooded animals (e.g., mouse, rat, rabbit, sheep, swine, bovine, cat, dog, monkey, birds, preferably cat and the like).

The kidney diseases to be the application target of the pharmaceutical composition of the present invention comprising AIMs, a drug that induces expression of AIM or a drug that stabilizes AIM are, for example, acute renal failure, chronic nephritis, chronic renal failure, nephrotic syndrome, diabetic nephropathy, nephrosclerosis, IgA nephropathy, hypertensive nephropathy, nephropathy associated with a collagen disease or IgM nephropathy, preferably acute renal failure or chronic renal failure can be mentioned. Representative nephropathy associated with collagen disease is, for example, lupus nephritis.

The pharmaceutical composition of the present invention comprising AIMs, a drug that induces expression of AIM or a drug that stabilizes AIM is of low toxicity, and can be administered as a liquid as it is, or as an appropriate dosage form of pharmaceutical composition, to humans or other warm-blooded mammals (e.g., mice, rats, rabbits, sheep, pigs, bovines, cats, dogs, monkeys, birds, preferably cat and the like) orally or parenterally (e.g., intravascular administration, subcutaneous administration and the like).

As examples of the composition for parenteral administration, injections, suppositories and the like are used; the injections may include dosage forms such as intravenous injections, subcutaneous injections, intracutaneous injections, intramuscular injections and drip infusion injections. Such an injection can be prepared according to a publicly known method. An injection can be prepared by, for example, dissolving, suspending or emulsifying the above-described AIMs, a drug that induces expression of AIM or a drug that stabilizes AIM of the present invention in a sterile aqueous or oily solution in common use for injections. As examples of aqueous solutions for injection, physiological saline, an isotonic solution comprising glucose or another auxiliary drug, and the like can be used, which may be used in combination with an appropriate solubilizer, for example, alcohol (e.g., ethanol), polyalcohol (e.g., propylene glycol, polyethylene glycol), non-ionic surfactant [e.g., polysorbate 80, HCO-50 (polyoxyethylene (50 mol) adduct of hydrogenated castor oil)] and the like. As examples of oily solutions, sesame oil, soybean oil and the like can be used, which may be used in combination with benzyl benzoate, benzyl alcohol and the like as solubilizers. The prepared injection solution is preferably filled in an appropriate ampoule. Suppositories used for rectal administration may be prepared by mixing the above-described AIMs, a drug that induces expression of AIM or a drug that stabilizes AIM of the present invention with an ordinary suppository base.

As the composition for oral administration, solid or liquid dosage forms, specifically tablets (including sugar-coated tables and film-coated tablets), pills, granules, powders, capsules (including soft capsules), syrups, emulsions, suspensions and the like can be mentioned. Such a composition is produced by a publicly known method, and may comprise a carrier, diluent or excipient in common use in the field of pharmaceutical making. As examples of the carrier or excipient for tablets, lactose, starch, sucrose, magnesium stearate and the like can be used.

The above-mentioned pharmaceutical composition for parenteral or oral administration is conveniently prepared in a medication unit dosage form suitable for the dosage of the active ingredient. As examples of such a medication unit dosage form, tablets, pills, capsules, injections (ampoules), and suppositories can be mentioned. It is preferable that the above-mentioned AIMs, a drug that induces expression of AIM or a drug that stabilizes AIM of the present invention be contained at, for example, normally 5 to 500 mg, particularly 5 to 100 mg for injections, or 10 to 250 mg for other dosage forms, per medication unit dosage form.

While the dose of the above-mentioned prophylactic or therapeutic agent of the present invention comprising AIMs, a drug that induces expression of AIM or a drug that stabilizes AIM varies depending on the subject of administration, target disease, symptoms, route of administration and the like; for example, when the agent is used for the treatment/prevention of kidney diseases in adult, it is convenient to administer the AIMs of the present invention usually at about 0.01 to 20 mg/kg body weight, preferably about 0.1 to 10 mg/kg body weight, and more preferably about 0.1 to 5 mg/kg body weight, based on a single dose, about 1 to 5 times a day, preferably about 1 to 3 times a day, for about 1-21 days, preferably about 1-14 days, by intravenous injection. In the case of other modes of parenteral administration and oral administration, similar doses may be administered. In case the symptom is particularly severe, the dose may be increased according to the symptom.

Each of the aforementioned compositions may comprise any other active ingredients that do not produce an unwanted interaction when formulated with the above-mentioned AIMs, a drug that induces expression of AIM or a drug that stabilizes AIM.

Furthermore, the AIMs, the drug that induces expression of AIM or the drug that stabilizes AIM of the present invention may be used in combination with other drugs useful for the treatment of kidney diseases, such as depressor (e.g., angiotensin-converting-enzyme inhibitor, angiotensin II receptor antagonist, calcium antagonist, rennin inhibitor, α blocker, β blocker etc.); diuretic (e.g., carbonic acid dehydrogenase inhibitor, loop diuretic, thiazide diuretic, antialdosterone drug, Potassium-sparing diuretic etc.); active vitamin D3 preparation (e.g., calcitriol, alfacalcildol, maxacalcitol, falecalcitriol etc.); oral carbonaceous adsorbent preparation (e.g., activated carbon etc.); potassium-correcting drug (e.g., sodium polystyrene sulfonate etc.); phosphorus adsorbent (e.g., calcium carbonate, calcium acetate, Sevelamer hydrochloride, lanthanum carbonate etc.), red blood cell hematopoiesis stimulation factor preparation (erythropoiesis stimulating agent; ESA) (e.g., erythropoietin preparation), amino acid infusion preparation and the like. The AIMs, the drug that induces expression of AIM or the drug that stabilizes AIM of the present invention and the above-described drugs may be administered to the patient at one time or different times.

As shown in the below-mentioned Examples, when AIM is not detected in the blood of a cat, it is suggested that cat AIM cannot bind to cat IgM in the blood and is easily excreted into the urine through the basal lamina of glomerulus. As a result, cat AIM cannot be stably present in the blood, and is considered to indirectly cause kidney diseases. Furthermore, it has been clarified that mouse AIM can bind to cat IgM in the blood of a cat, and particularly suggested that SRCR3 domain of mouse AIM is important for the binding with cat IgM. Therefore, the present invention also provides a prophylactic or therapeutic agent for a kidney disease for administration to a cat, which contains AIM or a partial peptide thereof that binds to cat IgM, or a nucleic acid comprising a base sequence encoding them.

AIM that binds to cat IgM in the present invention is a protein containing an amino acid sequence the same as or substantially the same as the amino acid sequence shown in SEQ ID NO: 4, which can bind to cat IgM.

Such protein may also be, for example, a protein chemically synthesized or biochemically synthesized in a cell-free translation system. Alternatively, the protein may be a recombinant protein produced from a transformant incorporating a nucleic acid comprising a base sequence that encodes the above-described amino acid sequence.

Substantially the same amino acid sequence as the amino acid sequence shown in SEQ ID NO:4 refers to an amino acid sequence having a homology of about 60% or more, preferably about 70% or more, further preferably about 80% or more, particularly preferably about 90% or more, most preferably about 95% or more, to the amino acid sequence shown in SEQ ID NO:4, and the like. The "homology" may be as mentioned above. More preferably, substantially the same amino acid sequence as the amino acid sequence shown in SEQ ID NO:4 is an amino acid sequence having an identity of about 60% or more, preferably about 70% or more, further preferably about 80% or more, particularly preferably about 90% or more, and most preferably about 95% or more, to the amino acid sequence shown in SEQ ID NO:4. As a protein comprising substantially the same amino acid sequence as the amino acid sequence shown in SEQ ID NO:4, for example, a protein comprising substantially the same amino acid sequence as the aforementioned amino acid sequence shown in SEQ ID NO:4, and having an activity of substantially the same quality as that of a protein comprising the amino acid sequence shown in SEQ ID NO:4 and the like are preferable. Here, the "activity of substantially the same quality" is as defined above.

While AIM protein that can bind to cat IgM may be any AIM protein as long as it binds to cat IgM in cat blood, for example, it is preferably a protein containing SRCR3 domain of mouse-derived AIM. Specifically, for example, an AIM protein containing amino acid Nos. 246-348 of the amino acid sequence shown in SEQ ID NO: 6 can be mentioned. A protein containing SRCR3 domain of mouse-derived AIM may be a protein wherein SRCR3 domain that AIM naturally has is substituted by SRCR3 domain of mouse-derived AIM.

The partial peptide of AIM that binds to cat IgM may be any as long as it is a peptide having the above-mentioned partial amino acid sequence of AIM that binds to cat IgM, and having an activity of substantially the same quality as AIM. Here, the "activity of substantially the same quality" is as defined above.

To be specific, for example, of the amino acid sequence shown in SEQ ID NO:4, partial amino acid sequences respectively comprising SRCR1 domain (amino acid Nos. 24-125 of the amino acid sequence shown in SEQ ID NO:4), SRCR2 domain (amino acid Nos. 139-239 of the amino acid sequence shown in SEQ ID NO:4), and SRCR3 domain (amino acid Nos. 244-346 of the amino acid sequence shown in SEQ ID NO:4), partial amino acid sequence comprising any combination of SRCR domains and the like can also be used. The size of the above-mentioned partial peptide is not particularly limited as long as it comprises the above-mentioned functional domain.

Examples of the DNA comprising a base sequence encoding AIM or a partial peptide thereof that binds to cat IgM include a DNA comprising the same or substantially the same base sequence as the base sequence shown in SEQ ID NO: 3 and the like.

As the DNA comprising the same or substantially the same base sequence as the base sequence shown in SEQ ID NO: 3, for example, a DNA comprising a base sequence having a homology of not less than about 60%, preferably not less than about 70%, more preferably not less than about 80%, particularly preferably not less than about 90%, with the base sequence shown in SEQ ID NO: 3, and encoding a protein having an activity of substantially the same quality as the aforementioned AIM and the like, is used. Here, the "homology" is as mentioned above. The DNA is similarly prepared as in the above-mentioned method.

As a subject of administration of a pharmaceutical composition containing AIM or a partial peptide thereof that binds to cat IgM, or a nucleic acid comprising a base sequence encoding them of the present invention, cat can be mentioned.

As a kidney disease to be the application target of a pharmaceutical composition containing AIM or a partial peptide thereof that binds to cat IgM, or a nucleic acid comprising a base sequence encoding them of the present invention, for example, acute renal failure, chronic nephritis, chronic renal failure, nephrotic syndrome, diabetic nephropathy, nephrosclerosis, IgA nephropathy, hypertensive nephropathy, nephropathy associated with a collagen disease, or IgM nephropathy, can be mentioned, and acute renal failure or chronic renal failure can be preferably mentioned. As representative nephropathy associated with a collagen disease, lupus nephritis can be mentioned.

A pharmaceutical composition containing AIM or a partial peptide thereof that binds to cat IgM, or a nucleic acid comprising a base sequence encoding them of the present invention is low toxic, and can be administered orally or parenterally to a target, similar to the above. The dosage form, dose and the like are as mentioned above.

As mentioned above, AIM knockout mouse showed symptoms of kidney diseases under conditions performing unilateral ureteral obstruction, transient kidney ischemia/reperfusion after uninephrectomy or bilateral transient kidney ischemia/reperfusion. This suggests that AIM knockout mouse under conditions performing unilateral ureteral obstruction, transient kidney ischemia/reperfusion after uninephrectomy or bilateral transient kidney ischemia/reperfusion can be provided as a new model mouse of kidney diseases. Therefore, the present invention provides a screening method for a prophylactic or therapeutic agent for kidney diseases, which uses an animal obtained by subjecting a non-human mammal deficient in AIM expression to unilateral ureteral obstruction, transient kidney ischemia/reperfusion after uninephrectomy or bilateral transient kidney ischemia/reperfusion.

A non-human mammal deficient in AIM expression means a non-human mammal having the expression of endogenous AIM inactivated therein, including AIM KO animals prepared from an ES cell having the AIM knocked out (KO) therein, as well as knockdown (KD) animals having the expression of the AIM inactivated by antisense or RNAi technology therein, and the like. Here, "knocked out (KO)" means that the production of complete mRNA is prevented by destroying or removing the endogenous gene, whereas "knocked down (KD)" means that translation from mRNA into protein is inhibited to inactivate the expression of the endogenous gene. Hereinafter, the AIM KO/KD animal of the present invention is sometimes simply referred to as "the KO/KD animal of the present invention". The AIM KO animal of the present invention is disclosed in Miyazaki T. et al. (J. Exp. Med., 189, 413-422, 1999 or WO 2013/162021).

"A non-human mammal" that can be a subject of the present invention is not particularly limited, as long as it is a non-human mammal for which a transgenic system has been established; examples include mice, rats, bovines, monkeys, pigs, sheep, goat, rabbits, dogs, cats, guinea pigs, hamsters, rats, mice and the like. Rabbits, dogs, cats, guinea pigs, hamsters and the like are preferable; in particular, from the viewpoint of the preparation of disease model animals, rodents, which have relatively short periods of ontogeny and life cycles, and which are easy to propagate, are more preferable; particularly, mice (e.g., C57BL/6 strain, BALE/c strain, DBA2 strain and the like as pure strains, B6C3F$_1$ strain, BDF$_1$ strain, B6D2F$_1$ strain, ICR strain and the like as hybrid strains) and rats (e.g., Wistar, SD and the like) are preferable.

In addition to mammals, birds such as chickens can be used for the same purpose as that of "non-human mammals" being subjects of the present invention.

A specific means for knocking out the AIM is disclosed in the aforementioned Miyazaki T. et al. (J. Exp. Med., 189, 413-422, 1999 or WO 2013/162021). As other known general methods, there can be preferably used a method comprising isolating the AIM (genomic DNA) derived from the subject non-human mammal by a conventional method, and integrating a DNA strand having a DNA sequence constructed to consequently inactivate the gene (hereinafter abbreviated as targeting vector), by, for example, (1) destroying the function of the exon or promoter by inserting another DNA fragment (e.g., drug resistance gene, reporter gene and the like) into the exon portion or promoter region, or (2) cutting out the entire or a portion of the AIM using the Cre-loxP system or Flp-frt system to delete the gene, or (3) inserting a stop codon into the protein coding region to prevent the translation into complete protein, or (4) inserting a DNA sequence that stops the transcription of the gene (e.g., polyA addition signal and the like) into the transcription region to prevent the synthesis of complete mRNA, at the AIM gene locus of the subject non-human mammal by homologous recombination, and the like.

The homologous recombinant can be acquired by, for example, introducing the above-described targeting vector into an embryonic stem cell (ES cell).

An ES cell refers to a cell derived from an inner cell mass (ICM) of a fertilized egg in the blastocyst stage, and can be cultivated and maintained while keeping the undifferentiated state in vitro. ICM cells are destined to form the embryo body, being stem cells on which all tissues, including germ cells, are based. The ES cell used may be of an established cell line, or of a cell line newly established in accordance with the method of Evans and Kaufman (Nature, vol. 292, p. 154, 1981). For example, in the case of mouse ES cells, ES cells derived from a 129 mouse strain are currently generally used, but the immunological background thereof is unclear; for the purposes of acquiring ES cells of a pure strain instead thereof with an immunologically clear genetic background and the like, an ES cell established from a C57BL/6 mouse or from a EDF$_1$ mouse (F$_1$ of C57BL/6 and DBA/2), wherein the small number of ova collectable from C57BL/6 has been improved by crossing with DBA/2, and the like can also be used suitably. In addition to being advantageous in that the number of ova collectable is high, and that the ova are robust, BDF$_1$ mice have the C57BL/6 mouse as the background thereof; therefore, ES cells derived therefrom can be used advantageously in that, when preparing a disease model mouse, the genetic background can be replaced with that of the C57BL/6 mouse by back-crossing with a C57BL/6 mouse. ES cells can be differentiated into a wide variety of types of cell, including parietal muscle, visceral muscles, and cardiac muscle, by monolayer culture until the reach of a high density, or suspension culture until the formation of cell aggregates, under appropriate conditions [M. J. Evans and M. H. Kaufman, Nature vol. 292, p. 154, 1981; G. R. Martin, Proceedings of the National Academy of Sciences, USA (Proc. Natl. Acad. Sci. U.S.A.), vol. 78, p. 7634, 1981; T. C. Doetschman et al., Journal of Embryology and Experimental Morphology, vol. 87, p. 27, 1985]; the cell of a non-human mammal deficient in AIM expression, which is obtained by differentiating an ES cell incorporating targeting vector of the present invention, is useful in cell biological investigations of AIM in vitro.

For example, if a targeting vector is designed to destroy the function of an exon or promoter by inserting another DNA fragment into the exon portion or promoter region of the AIM, the vector can assume, for example, the constitution shown below.

First, to ensure that another DNA fragment is inserted into the exon or promoter portion of the AIM by homologous recombination, the targeting vector need to comprise sequences homologous to the respective target sites (5' arm and 3' arm) upstream of the 5' and downstream of the 3' in the other DNA fragment.

Although the other DNA fragment inserted is not particularly limited, it is possible to select ES cells having a targeting vector integrated in a chromosome thereof with drug resistance or reporter activity as the index, by using a drug resistance gene or a reporter gene. Here, examples of the drug resistance gene and examples of the reporter gene include, but are not limited to, the neomycin phosphotransferase II (nptII) gene, the hygromycin phosphotransferase (hpt) gene and the like, and the β-galactosidase (lacZ) gene, the chloramphenicol acetyltransferase (cat) gene and the like, respectively.

The drug resistance or reporter gene is preferably under the control of an optionally chosen promoter capable of functioning in mammalian cells. For example, virus promoters such as the SV40 early promoter, cytomegalovirus (CMV) long terminus repeat (LTR), Rous sarcoma virus (RSV) LTR, mouse leukemia virus (MoMuLV) LTR, and adenovirus (AdV)-derived early promoter, and promoters for mammalian constitutive protein genes such as the β-actin gene promoter, PGK gene promoter, and transferrin gene promoter and the like can be mentioned. However, if the drug resistance or reporter gene is inserted into the AIM so that it is placed under the control of an endogenous promoter of the AIM, a promoter that controls the transcription of the gene need not be present in the targeting vector.

The targeting vector preferably has a sequence that terminates the transcription of mRNA from the gene (polyadenylation (polyA) signal, also called terminator) downstream of the drug resistance or reporter gene; for example, terminator sequences derived from virus genes, or from various mammal or bird genes, can be used. Preferably, an SV40 terminator and the like are used.

Usually, gene recombination in a mammal occurs mostly non-homologously; the introduced DNA is randomly inserted at an optionally chosen position on the chromosome. Therefore, it is not possible to efficiently select only those clones targeted to the endogenous AIM targeted by homologous recombination by selection based on the detection of the expression of a drug resistance or reporter gene and the like (positive selection); it is necessary to confirm the site of integration by Southern hybridization or PCR for all the clones selected. Hence, provided that, for example, the herpes simplex virus-derived thymidine kinase (HSV-tk) gene, which confers gancyclovir susceptibility, is joined outside the region homologous to the target sequence of the targeting vector, the cells having the vector inserted randomly thereinto cannot grow in a gancyclovir-comprising medium because they have the HSV-tk gene, whereas the cells targeted to the endogenous AIM locus by homologous recombination become resistant to gancyclovir and are selected because they do not have the HSV-tk gene (negative selection). Alternatively, provided that the diphtheria toxin gene, for example, is joined in place of the HSV-tk gene, the cells having the vector inserted randomly thereinto die due to the toxin produced by themselves, so that a homologous recombinant can also be selected in the absence of a drug.

Although any of the calcium phosphate co-precipitation method, electroporation method, lipofection method, retrovirus infection method, aggregation method, microinjection method, gene gun (particle gun) method, DEAE-dextran method and the like can be used for targeting vector introduction into ES cells, the electroporation method is generally chosen because of the ease of treatment of a large number of cells and the like, since gene recombination in a mammal occurs mostly non-homologously so that the frequency of obtainment of homologous recombinants is low, as described above. For the electroporation, ordinary conditions used for transfection into animal cells may be used as is; for example, the electroporation can be performed by trypsinizing ES cells in the logarithmic growth phase to disperse them as single cells, suspending the cells in a medium to obtain a density of $10^6$ to $10^8$ cells/ml, transferring the cells to a cuvette, adding 10 to 100 μg of a targeting vector, and applying an electric pulse of 200 to 600 V/cm.

ES cells having the targeting vector integrated therein can be determined by screening chromosomal DNA separated and extracted from a colony obtained by culturing the single cells on feeder cells, by Southern hybridization or PCR; if a drug resistance gene or a reporter gene is used as the other DNA fragment, it is possible to select a transformant at the cellular stage with the expression thereof as the index. For example, if a vector comprising the nptII gene as the marker gene for positive selection is used, ES cells after transfection treatment are cultured in a medium comprising a neomycin-type antibiotic such as G418, and the resulting resistant colony is selected as a candidate for a transformant. If a vector comprising the HSV-tk gene is used as the marker gene for negative selection, the ES cells are cultured in a medium comprising ganciclovir, and the resulting resistant colony is selected as a candidate for a homologous recombinant. The colonies obtained are transferred to respective culture plates, and trypsinization and medium exchanges are repeated, after which a portion is reserved for cultivation, and the remainder is subjected to PCR or Southern hybridization to confirm the presence of the introduced DNA.

When an ES cell confirmed to have the introduced DNA integrated therein is brought back to an embryo derived from a non-human mammal of the same species, the ES cell gets integrated into the ICM of the host embryo to form a chimeric embryo. This is transplanted into a recipient mother (embryo recipient female) and allowed to continue development, whereby a chimeric KO animal is obtained. If the ES cell contributes to the formation of a primordial germ cell that will differentiate into an egg or spermatozoon in the chimeric animal, a germline chimera will be obtained; by mating this, a KO animal having deficiency in the expression of the AIM maintained genetically therein can be prepared.

For preparing a chimeric embryo, there are a method wherein early embryos up to the morula stage are adhered and aggregated together (aggregation chimera method) and a method wherein a cell is micro-injected into a blastocoel cavity of a blastocyst (injection chimera method). Although the latter has traditionally been widely conducted in the preparation of a chimeric embryo using an ES cell, a method wherein an aggregation chimera is created by injecting an ES cell into the zona pellucida of an 8-cell stage embryo, and a method wherein an aggregation chimera is created by co-culturing and aggregating an ES cell mass and an 8-cell stage embryo deprived of the zona pellucida, as a method which does not require a micromanipulator and which can be easily operated, have recently been conducted.

In all cases, a host embryo can be collected from a non-human mammal that can be used as a female for egg collection in transfection into a fertilized egg as mentioned below in the same manner; for example, in the case of a mouse, to make it possible to determine the percent contribution of ES cells to the formation of a chimeric mouse by coat color, it is preferable that the host embryo be collected from a mouse of a strain showing a coat color different from that of the strain from which the ES cell is derived. For example, in the case of an ES cell derived from a 129 mouse strain (coat color: agouti), a C57BL/6 mouse (coat color: black) or an ICR mouse (coat color: albino) is used as the female for egg collection; in the case of an ES cell derived from a C57BL/6 or $DBF_1$ mouse (coat color: black) or from a TT2 cell (derived from $F_1$ (coat color: agouti) of C57BL/6 and CBA), an ICR mouse or a BALE/c mouse (coat color: albino) can be used as the female for egg collection.

Because the germline chimera formation capacity depends largely on the combination of an ES cell and a host embryo, it is more preferable that a combination showing a high germline chimera formation capacity be chosen. For example, in the case of a mouse, it is preferable to use a host embryo derived from the C57BL/6 strain and the like for ES cells derived from the 129 strain, and to use a host embryo derived from the BALE/c strain and the like for ES cells derived from the C57BL/6 strain.

It is preferable that the female mouse for egg collection be about 4 to about 6 week-old, and that the male mouse for mating be of the same strain at about 2 to about 8 month-old. Although the mating may be by natural mating, it is preferably performed after administering gonadotropic hormones (follicle-stimulating hormone, then luteinizing hormone) to induce overovulation.

In the case of the blastocyst injection method, a blastocystic embryo (e.g., in the case of a mouse, at about 3.5 days after mating) is collected from the uterus of a female for egg collection (or an early embryo in the morula stage or before, after being collected from the oviduct, may be cultured in a medium (below-mentioned) for embryo culture until the blastocyst stage), and ES cells (about 10 to about 15 cells) having a targeting vector introduced thereinto are injected into a blastocoel cavity of the blastocyst using a micromanipulator, after which the embryos are transplanted into the uterus of a pseudopregnant embryo recipient female non-human mammal. As the embryo recipient female non-human mammal, a non-human mammal that can be used as an embryo recipient female in transfection into a fertilized egg can be used in the same manner.

In the case of the co-culture method, 8-cell stage embryos and morulas (e.g., in the case of a mouse, about 2.5 days after mating) are collected from the oviduct and uterus of a female for egg collection (or an early embryo in the 8-cell stage or before, after being collected from the oviduct, may be cultured in a medium (below-mentioned) for embryo culture until the 8-cell stage or morula stage), and the zona pellucida is lysed in acidic Tyrode's solution, after which an ES cell mass incorporating a targeting vector (number of cells: about 10 to about 15 cells) is placed in a microdrop of a medium for embryo culture overlaid with mineral oil, the above-described 8-cell stage embryo or morula (preferably 2 embryos) is further placed, and they are co-cultured overnight. The morula or blastocyst obtained is transplanted to the uterus of an embryo recipient female non-human mammal as described above.

If the transplanted embryo implants successfully and the embryo recipient female becomes pregnant, chimeric non-human mammal will be obtained by natural delivery or caesarean section. Embryo recipient females that have delivered spontaneously are allowed to continue suckling; if the pups are delivered by caesarean section, the pups can be suckled by a separately provided female for suckling (a female non-human mammal with usual mating and delivery).

For the selection of a germline chimera, if the sex of the ES cell has already been determined, a chimeric mouse of the same sex as the ES cell first is selected (usually, a male chimeric mouse is chosen since a male ES cell is used), and then a chimeric mouse showing a high ES cell contribution rate (e.g., 50% or more) is selected on the basis of phenotypes such as coat color. For example, in the case of a chimeric mouse obtained from a chimeric embryo between a D3 cell, which is a male ES cell derived from a 129 mouse strain, and a host embryo derived from a C57BL/6 mouse, it is preferable that a male mouse showing a high percentage of the agouti coat color be selected. Whether or not the selected chimeric non-human mammal is a germline chimera can be determined on the basis of the phenotypes of the $F_1$ animal obtained by crossing with an appropriate strain of the same animal species. For example, in the case of the above-described chimeric mouse, agouti is dominant over black; therefore, when the male mouse is crossed with a female C57BL/6 mouse, the coat color of the $F_1$ obtained is agouti if the selected male mouse is a germline chimera.

The thus-obtained germline chimeric non-human mammal incorporating a targeting vector (founder) is usually obtained as a heterozygote having the AIM only knocked out in either one of the homologous chromosomes. To obtain a homozygote having the AIM knocked out in both homologous chromosomes, of the $F_1$ animals obtained as described above, siblings of heterozygotes may be crossed. Selection of heterozygotes can be determined by, for example, screening chromosomal DNAs separated and extracted from the tail of an $F_1$ animal by Southern hybridization or PCR. ¼ of the $F_2$ animals obtained will be homozygotes.

In another preferred embodiment with the use of a virus as the targeting vector, a method comprising infecting an ES cell of a non-human mammal with a virus comprising a DNA comprising a marker gene for positive selection inserted between the 5' and 3' arms, and a marker gene for negative selection outside the arms, can be mentioned (see, for example, Proceedings of the National Academy of Sciences, USA (Proc. Natl. Acad. Sci. USA), vol. 99, No. 4, pp. 2140-2145, 2002). For example, when retrovirus or lentivirus is used, cells are sown to an appropriate culture vessel such as a culture dish, a virus vector is added to the culture broth (if desired, polybrene may be co-present), the cells are cultured for 1 to 2 days, after which, cultivation is continued with the addition of a selection drug as described above, and cells having the vector integrated therein are selected.

Regarding specific means for knocking down the AIM, a method comprising introducing a DNA that encodes an antisense RNA or siRNA (including shRNA) of AIM using techniques of preparation of transgenic animals known per se, and allowing it to be expressed in the subject non-human mammal cell and the like can be mentioned.

A DNA comprising a base sequence complementary to the target region of a desired polynucleotide, i.e., a DNA hybridizable with a desired polynucleotide, can be said to be "antisense" against the desired polynucleotide.

The antisense DNA having a base sequence complementary or substantially complementary to the base sequence of a polynucleotide that encodes AIM or a portion thereof may be any antisense DNA, as long as it comprises a base sequence complementary or substantially complementary to the base sequence of the polynucleotide that encodes AIM or a portion thereof, and having an action to suppress the expression of the polynucleotide.

The base sequence substantially complementary to a polynucleotide that encodes AIM is, for example, a base sequence having a homology of about 70% or more, preferably about 80% or more, more preferably about 90% or more, most preferably about 95% or more, to the base sequence of the complementary strand of the polynucleotide for the overlapping region. Base sequence homology herein can, for example, be calculated using the homology calculation algorithm NCBI BLAST (National Center for Biotechnology Information Basic Local Alignment Search Tool) under the following conditions (expect=10; gap allowed; filtering=ON; match score=1; mismatch score=−3).

Particularly, of the full base sequence of the complementary strand of the polynucleotide that encodes AIM, (a) in the case of an antisense DNA intended to inhibit the translation, an antisense DNA having a homology of about 70% or more, preferably about 80% or more, more preferably about 90% or more, most preferably about 95% or more, to the complementary strand of the base sequence of the portion that encodes the N-terminus part of AIM (e.g., a base sequence in the vicinity of the initiation codon and the like) is suitable, and (b) in the case of an antisense DNA intended to degrade RNA with RNaseH, an antisense DNA having a homology of about 70% or more, preferably about 80% or more, more preferably about 90% or more, most preferably about 95% or more, to the complementary strand of the full base sequence of the polynucleotide that encodes AIM including the intron, is suitable.

Specifically, when the subject non-human mammal is a mouse, an antisense DNA comprising a base sequence complementary or substantially complementary to the base sequence registered under GenBank accession No. AF011428 or a portion thereof, preferably, an antisense DNA comprising a base sequence complementary to the base sequence or a portion thereof, and the like can be mentioned.

An antisense DNA having a base sequence complementary or substantially complementary to the base sequence of a polynucleotide that encodes AIM or a portion thereof (hereinafter, also referred to as "the antisense DNA of the present invention") can be designed and synthesized on the basis of base sequence information on a DNA that encodes cloned or determined AIM. Such antisense DNA is capable of inhibiting the replication or expression of the AIM. Specifically, the antisense DNA of the present invention is capable of hybridizing with an RNA transcribed from the AIM (mRNA or initial transcription product), and capable of inhibiting the synthesis (processing) or function (translation into protein) of mRNA.

The target region of the antisense DNA of the present invention is not particularly limited with respect to the length thereof, as long as the translation into AIM is inhibited as a result of hybridization of the antisense DNA; the target region may be the entire sequence or a partial sequence of the mRNA that encodes the protein, and the length is about 10 bases for the shortest, and the entire sequence of the mRNA or initial transcription product for the longest. Specifically, the 5' end hairpin loop, 5' end 6-base-pair repeats, 5' end untranslated region, translation initiation codon, protein coding region, ORF translation stop codon, 3' end untranslated region, 3' end palindrome region, or 3' end hairpin loop of the AIM and the like may be chosen as a preferable target region of the antisense DNA, but any other region in the AIM gene may also be chosen as the target. For example, the intron portion of the gene may also be the target region.

Furthermore, the antisense DNA of the present invention may be one that not only hybridizes with the mRNA or initial transcription product of AIM to inhibit the translation into protein, but also is capable of binding to the AIM being a double-stranded DNA to form a triple strand (triplex) and hence to inhibit the transcription to RNA. Alternatively, the antisense DNA of the present invention may be one that forms a DNA:RNA hybrid to induce the degradation by RNaseH.

A DNA that encodes a ribozyme capable of specifically cleaving the mRNA or the initial transcription product that encodes AIM within the coding region (including the intron portion in the case of the initial transcription product) can also be encompassed in the antisense DNA of the present invention. One of the most versatile ribozymes is a self-splicing RNA found in infectious RNAs such as viroid and virusoid, and the hammerhead type, the hairpin type and the like are known. The hammerhead type exhibits enzyme activity with about 40 bases in length, and it is possible to specifically cleave the target mRNA by making several bases at both ends flanking to the hammerhead structure portion (about 10 bases in total) a sequence complementary to the desired cleavage site of the mRNA. Because this type of ribozyme has only RNA as the substrate, it offers an additional advantage of non-attack of genomic DNA. Provided that the AIM mRNA assumes a double-stranded structure per se, the target sequence can be made to be single-stranded by using a hybrid ribozyme prepared by joining an RNA motif derived from a viral nucleic acid that can bind specifically to RNA helicase [Proc. Natl. Acad. Sci. USA, 98(10): 5572-5577 (2001)]. Furthermore, the ribozyme may be a hybrid ribozyme prepared by further joining a sequence modified from the tRNA to promote the translocation of the transcription product to cytoplasm [Nucleic Acids Res., 29(13): 2780-2788 (2001)].

Herein, a double-stranded RNA consisting of an oligo-RNA homologous to a partial sequence (including the intron portion in the case of the initial transcription product) in the coding region of the mRNA or initial transcription product of AIM and a strand complementary thereto, what is called a single-chain interfering RNA (siRNA), can also be used to prepare the KD animal of the present invention. It had been known that so-called RNA interference (RNAi), which is a phenomenon that when siRNA is introduced into cells, an mRNA homologous to the RNA is degraded, occurs in nematodes, insects, plants and the like; since this phenomenon was also confirmed to widely occur in animal cells [Nature, 411(6836): 494-498 (2001)], siRNA has been utilized as an alternative technique to ribozymes. siRNA can be designed as appropriate on the basis of base sequence information of the mRNA being the target using commercially available software (e.g., RNAi Designer; Invitrogen).

The antisense oligo-DNA and ribozyme of the present invention can be prepared by determining the target sequence for the mRNA or initial transcription product on the basis of a cDNA sequence or genomic DNA sequence of AIM, and synthesizing a sequence complementary thereto using a commercially available DNA/RNA synthesizer (Applied Biosystems, Beckman, and the like). By inserting the synthesized antisense oligo-DNA or ribozyme downstream of the promoter in the expression vector, via an appropriate linker (adapter) sequence used as required, a DNA expression vector that encodes the antisense oligo-RNA or ribozyme can be prepared. Examples of expression vectors that can be used preferably here include plasmids from *Escherichia coli, Bacillus subtilis*, or yeast, bacteriophages such as λ phage, retroviruses such as Moloney leukemia virus, animal or insect viruses such as lentivirus, adeno-associated virus, vaccinia virus and baculovirus, and the like. In particular, plasmids (preferably plasmids from *Escherichia coli, Bacillus subtilis*, or yeast, particularly plasmids from *Escherichia coli*) and animal viruses (preferably retrovirus, lentivirus) are preferable. Examples of promoters include virus promoter such as the SV40 early promoter, cytomegalovirus (CMV) long terminus repeat (LTR), Rous sarcoma virus (RSV) LTR, mouse leukemia virus (MoMuLV) LTR, and adenovirus (AdV) derived early promoter, and promoters for mammalian constitutive protein genes such as the β-actin gene promoter, PGK gene promoter, and transferrin gene promoter and the like.

A DNA expression vector that encodes a longer antisense RNA (e.g., full-length complementary strand of AIM mRNA and the like) can be prepared by inserting an AIM cDNA, cloned by a conventional method, in the reverse direction, via an appropriate linker (adapter) sequence used as required, downstream of the promoter in the expression vector.

Meanwhile, a DNA that encodes siRNA can be prepared by separately synthesizing a DNA that encodes a sense strand and a DNA that encodes an antisense strand, and inserting them into an appropriate expression vector. As the siRNA expression vector, one having a Poi III system promoter such as U6 or H1 can be used. In this case, in the animal cell incorporating the vector, the sense strand and the antisense strand are transcribed and annealed to form siRNA. shRNA can be prepared by inserting a unit comprising a sense strand and an antisense strand separated by a length of bases allowing the formation of an appropriate loop structure (e.g., about 15 to 25 bases) into an appropriate expression vector. As the shRNA expression vector, one having a Pol III system promoter such as U6 or H1 can be used. In this case, the shRNA transcribed in the animal cell incorporating the expression vector forms a loop by itself, and is then processed by an endogenous enzyme dicer and the like to form mature siRNA. Alternatively, it is also possible to achieve knockdown by RNAi by expressing a microRNA (miRNA) comprising the siRNA sequence being the target using a Pol II promoter. In this case, by a promoter showing tissue-specific expression, tissue-specific knockdown is also possible.

For introducing an expression vector comprising a DNA that encodes an antisense RNA, siRNA, shRNA, or miRNA of AIM into a cell, a method known per se is used as appropriate according to the target cell. For example, for introduction into an early embryo such as a fertilized egg, the microinjection method is used. For introduction into an ES cell, the calcium phosphate co-precipitation method, electroporation method, lipofection method, retrovirus infection method, aggregation method, microinjection method, particle gun method, DEAE-dextran method and the like can be used. Alternatively, when retrovirus, lentivirus and the like are used as the vector, it is sometimes possible to achieve transfection conveniently by adding the virus to an early embryo or an ES cell, and culturing the embryo or cell for 1 to 2 days to infect the cells with the virus. Regeneration of individuals from an ES cell (establishment of founder), passage (preparation of homozygotes) and the like can be performed as described above with respect to the KO animal of the present invention.

In a preferred embodiment, the expression vector comprising a DNA that encodes an antisense RNA, siRNA, shRNA, or miRNA of AIM is introduced into an early embryo (fertilized egg) of a non-human mammal being the subject by microinjection.

DNA microinjection into the fertilized egg can be performed by a conventional method using a commonly known device such as a micromanipulator. Briefly, the fertilized egg placed in a microdrop of a medium for embryo culture is aspirated and immobilized using a holding pipette, and a DNA solution is injected directly into the male or female pronucleus, preferably into the male pronucleus, using an injection pipette. The DNA for introduction is used preferably after being highly purified using CsCl density gradient ultracentrifugation or an anion exchange resin column and the like. It is also preferable that the DNA for introduction be linearized in advance by cutting the vector portion using a restriction enzyme.

After introducing the DNA, the fertilized egg is cultured in a medium for embryo culture in 5% gaseous carbon dioxide/95% atmosphere by the microdrop culture method and the like until the 1-cell stage to blastocyst stage, after which it is transplanted to the oviduct or uterus of a female non-human mammal for embryo reception rendered to be pseudopregnant. The female non-human mammal for embryo reception may be any one of the same species as the animal from which the early embryo to be transplanted is derived; for example, when a mouse early embryo is transplanted, a female ICR mouse (preferably about 8 to about 10 weeks of age) and the like are preferably used. A known method of rendering a female non-human mammal for embryo reception pseudopregnant is, for example, a method comprising mating the female with a vasectomized (vasoligated) male non-human mammal of the same species (e.g., in the case of a mouse, with a male ICR mouse (preferably about 2 months or more of age)), and selecting a female confirmed to have a vaginal plug.

The female for embryo reception used may be one that has ovulated spontaneously, or one receiving luteinizing hormone releasing hormone (generally abbreviated as LHRH) or an analogue thereof administered prior to mating with a vasectomized (vasoligated) male, to induce fertility. Examples of the LHRH analogue include [3,5-DiI-Tyr$^5$]-LH-RH, [Gln$^8$]-LH-RH, [D-Ala$^6$]-LH-RH, [des-Gly$^{10}$]-LH-RH, [D-His(Bzl)$^6$]-LH-RH and Ethylamides thereof and the like. The amount of LHRH or an analogue thereof administered, and the time of mating with a male non-human mammal after the administration vary depending on the species of the non-human mammal. For example, when the non-human mammal is a mouse (preferably an ICR mouse and the like), it is usually preferable that the female mouse be mated with a male mouse about 4 days after administration of LHRH or an analogue thereof; the amount of LHRH or an analogue thereof administered is usually about 10 to 60 µg/individual, preferably about 40 µg/individual.

Usually, if the early embryo to be transplanted is in the morula stage or after, the embryo is transplanted to the uterus of a female for embryo reception; if the early embryo is in a stage before the morula stage (e.g., 1-cell stage to 8-cell stage embryo), the embryo is transplanted to the oviduct. The female for embryo reception is used as appropriate after elapse of a given number of days after becoming pseudopregnant depending on the developmental stage of the embryo to be transplanted. For example, in the case of a mouse, a female mouse at about 0.5 days after becoming pseudopregnant is preferable for the transplantation of a 2-cell stage embryo, and a female mouse at about 2.5 days after becoming pseudopregnant is preferable for the transplantation of a blastocystic embryo. After the female for embryo reception is anesthetized (preferably, Avertin, Nembutal and the like are used), an incision is made, the ovary is pulled out, and early embryos (about 5 to about 10 embryos) in suspension in a medium for embryo culture are injected into the vicinity of the abdominal osteum of the uterine tube or the uterine tube junction of the uterine horn using a pipette for embryo transplantation.

When the transplanted embryo implants successfully and the embryo recipient female becomes pregnant, non-human mammal pups will be obtained by spontaneous delivery or caesarian section. Embryo recipient females that have delivered spontaneously are allowed to continue suckling; when the pups are delivered by caesarian section, the pups can be suckled by a separately provided female for suckling (e.g., in the case of the mouse, a female mouse with usual mating and delivery (preferably a female ICR mouse and the like)).

Transfer of the DNA that encodes an antisense RNA, siRNA, shRNA, or miRNA of AIM in the fertilized egg cell stage is secured so that the introduced DNA will be present in all of the germline cells and somatic cells of the subject non-human mammal. Whether or not the introduced DNA is integrated in chromosomal DNA can be determined by, for example, screening chromosomal DNAs separated and extracted from the tail of the pup, by Southern hybridization or PCR. The presence of the expression vector in the germline cells of the offspring non-human mammal ($F_0$) obtained as described above means that the expression vector is present in all of the germline cells and somatic cells of all animals in the subsequent generation ($F_1$).

Usually, $F_0$ animals are obtained as heterozygotes having the introduced DNA in either of the homologous chromosomes. Different $F_0$ individuals have the introduced DNA inserted randomly on different chromosomes unless the insertion is by homologous recombination. To obtain a homozygote having the expression vector in both of the homologous chromosomes, an $F_0$ animal and a non-transgenic animal are crossed to prepare an $F_1$ animal, and heterozygous siblings thereof having the introduced DNA in either of the homologous chromosomes may be crossed. If the introduced DNA is integrated only at one gene locus, ¼ of the $F_2$ animals obtained will be homozygotes.

In another preferred embodiment with the use of a virus as the vector, as with the above-described case of KO animals, a method comprising infecting an early embryo or ES cell of a non-human mammal with a virus comprising a DNA that encodes an antisense RNA, siRNA, shRNA, or miRNA of AIM can be mentioned. When a fertilized egg is used as the cell, it is preferable that the zone pallucida be removed prior to infection. After cultivation for 1 to 2 days following infection with the virus vector, the fertilized egg is transplanted to the oviduct or uterus of a female non-human mammal for embryo reception rendered to be pseudopregnant as described above in the case of an early embryo, or the fertilized egg is continued to be cultured with the addition of a selection drug as described above in the case of an ES cell, and a cell incorporating the vector is selected.

Furthermore, as described in the Proceedings of the National Academy of Sciences, USA (Proc. Natl. Acad. Sci. USA), vol. 98, pp. 13090-13095, 2001, a spermatogonium collected from a male non-human mammal is infected with a virus vector during co-cultivation with STO feeder cells, after which the spermatogonium is injected into the seminiferous tube of a male infertile non-human mammal, and the male infertile non-human mammal is mated with a female non-human mammal, whereby pups that are hetero-Tg (+/−) for a DNA that encodes an antisense RNA, siRNA, shRNA, or miRNA of AIM can be obtained efficiently.

The non-human mammal deficient in the expression of the AIM gene of the present invention, which is described in Miyazaki T. et al. (J. Exp. Med., 189, 413-422, 1999 or WO 2013/162021), or obtained by the above-mentioned method, has the following characteristics under conditions performing unilateral ureteral obstruction, transient kidney ischemia/reperfusion after uninephrectomy or bilateral transient kidney ischemia/reperfusion:
(1) necrotic renal tubule cells are accumulated, and kidney parenchyma becomes fibrosis as compared to control kidney in kidney that underwent ureter obstruction or transient kidney ischemia/reperfusion,
(2) glomerular structure is disintegrated and glomerulus becomes fibrosis as compared to control kidney in kidney that underwent ureter obstruction or transient kidney ischemia/reperfusion,
(3) expression of inflammatory cytokine is promoted as compared tocontrol kidney in kidney that underwent ureter obstruction or transient kidney ischemia/reperfusion,
(4) infiltration of macrophage is promoted as compared to control kidney in kidney that underwent ureter obstruction or transient kidney ischemia/reperfusion,
(5) blood BUN value of non-human mammal deficient in AIM expression is high as compared to control non-human mammal,
(6) the survival rate of non-human mammal deficient in AIM expression is low as compared to control non-human mammal,
(7) the aforementioned (1)-(6) are improved by AIM administration. These phenotypes have not been reported at least in conventionally publicly known AIM KO mice. Particularly, they are similar to the pathologies of chronic renopathy associated with acute renopathy (acute renal failure) triggered by ureter compression•obstruction due to uretercalculus, ascending urinary tract infection, tumor or the like, and chronic renopathy associated with ischemic renopathy caused by tumor mass, thrombus, or kidney angiostenosis or obstruction due to diabetes, hypertension and the like, which is a new finding.

(1) That necrotic renal tubule cells are accumulated, and kidney parenchyma becomes fibrosis in kidney that underwent ureter obstruction or transient kidney ischemia/reperfusion as compared to control kidney (normal kidney, or kidney free of ureter obstruction or transient kidney ischemia/reperfusion, hereinafter the same) means that accumulation of necrotic renal tubule cells, and wide fibrosis of kidney parenchyma are observed in kidney that underwent ureter obstruction or transient kidney ischemia/reperfusion as compared to control kidney, by subjecting the non-human mammal deficient in AIM expression in the present invention to unilateral ureteral obstruction, transient kidney ischemia/reperfusion after uninephrectomy or bilateral transient kidney ischemia/reperfusion. Accumulation of necrotic renal tubule cells can be confirmed by, for example, hematoxylin-eosin staining of kidney tissue sections, and renal parenchymal fibrosis can be confirmed by simultaneous staining by Azan staining and hematoxylin staining. In the below-mentioned Examples, a significant difference was observed in AIM knockout mouse, as compared to control kidney, from day 14 after ureter obstruction. In addition, a significant difference was observed in AIM knockout mouse as compared to control kidney, from day 7 after transient kidney ischemia/reperfusion.

(2) That glomerular structure is disintegrated and glomerulus becomes fibrosis, as compared to control kidney, in kidney that underwent ureter obstruction or transient kidney ischemia/reperfusion means that disintegration of glomerular structure and fibrosis of glomerulus are observed in kidney that underwent ureter obstruction or transient kidney ischemia/reperfusion, as compared to control kidney, by subjecting the non-human mammal deficient in AIM expression in the present invention to unilateral ureteral obstruction, transient kidney ischemia/reperfusion after uninephrectomy or bilateral transient kidney ischemia/reperfusion. Disintegration of glomerular structure can be confirmed by, for example, hematoxylin-eosin staining of kidney tissue sections, and fibrosis of glomerulus can be confirmed by simultaneous staining by Azan staining and hematoxylin staining. In the below-mentioned Examples, a significant difference was observed in AIM knockout mouse as compared to normal kidney, from day 14 after ureter obstruction. In addition, a significant difference was observed in AIM knockout mouse as compared to normal kidney, from day 7 after transient kidney ischemia/reperfusion.

(3) That expression of inflammatory cytokine is promoted as compared to control kidney, in kidney that underwent ureter obstruction or transient kidney ischemia/reperfusion means that expression of MCP-1, IL-1β and IL-6 is promoted in kidney that underwent ureter obstruction or transient kidney ischemia/reperfusion as compared to control kidney, by subjecting the non-human mammal deficient in AIM expression in the present invention to unilateral ureteral obstruction, transient kidney ischemia/reperfusion after uninephrectomy or bilateral transient kidney ischemia/reperfusion. Promotion of expression can be confirmed by, for example, quantitative RT-PCR, Northern blot method and the like. In the below-mentioned Examples, a significant difference in MCP-1 and IL-6 was observed in AIM knockout mouse as compared to normal kidney and a tendency of high expression of IL-1β was also observed.

(4) That infiltration of macrophage is promoted as compared to control kidney, in kidney that underwent ureter obstruction or transient kidney ischemia/reperfusion means that the number of macrophage (Mac-1 positive cell) is high in kidney that underwent ureter obstruction or transient kidney ischemia/reperfusion as compared to control kidney, by subjecting the non-human mammal deficient in AIM expression in the present invention to unilateral ureteral obstruction, transient kidney ischemia/reperfusion after uninephrectomy or bilateral transient kidney ischemia/reperfusion. The count of cell number can be confirmed by, for example, identifying Mac-1 positive cells by flow cytometer and the like. In the below-mentioned Examples, it was confirmed that the ratio of macrophage is high in AIM knockout mouse as compared to normal kidney.

(5) That blood BUN value of non-human mammal deficient in AIM expression is high as compared to control non-human mammal means that the blood BUN value of non-human mammal deficient in AIM expression is high as compared to control non-human mammal by subjecting the non-human mammal deficient in AIM expression in the present invention to unilateral ureteral obstruction, transient kidney ischemia/reperfusion after uninephrectomy or bilateral transient kidney ischemia/reperfusion.

(6) That the survival rate of non-human mammal deficient in AIM expression is low as compared to control non-human mammal means that the survival rate is low as compared to control non-human mammal by subjecting the non-human mammal deficient in AIM expression in the present invention to unilateral ureteral obstruction, transient kidney ischemia/reperfusion after uninephrectomy or bilateral transient kidney ischemia/reperfusion.

(7) That the aforementioned (1)-(6) are improved by AIM administration means that significant decrease in BUN value is observed in that accumulation of necrotic renal tubule cells and disintegration of glomerular structure, and fibrosis of kidney parenchyma and glomerulus associated therewith are obviously improved, that expression of inflammatory cytokine is decreased, that the survival rate is improved, and that infiltration of macrophage is suppressed, by subjecting the non-human mammal deficient in AIM expression of the present invention to unilateral ureteral obstruction, transient kidney ischemia/reperfusion after uninephrectomy or bilateral transient kidney ischemia/reperfusion, followed by AIM administration.

These findings indicate that a non-human mammal deficient in AIM expression which is subjected to unilateral ureteral obstruction, transient kidney ischemia/reperfusion after uninephrectomy or bilateral transient kidney ischemia/reperfusion is useful as an animal model of kidney diseases, and can be further used for screening for a prophylactic or therapeutic drug for kidney diseases. Specifically, the screening method of the present invention comprises the following steps:

(1) a step of administering, under conditions performing unilateral ureteral obstruction, transient kidney ischemia/reperfusion after uninephrectomy or bilateral transient kidney ischemia/reperfusion, a test substance to a non-human mammal deficient in AIM expression, (2) a step of observing any one or more items of the following properties of the non-human mammal deficient in AIM expression, which is administered with the test substance:
(i) accumulation of necrotic renal tubule cells and renal parenchymal fibrosis,
(ii) disintegration and fibrosis of glomerular structure,
(iii) expression level of inflammatory cytokine in the kidney,
(iv) ratio of macrophage in the kidney,
(v) BUN value,
(vi) survival rate, (3) a step of selecting a test substance that improves any one or more items of the aforementioned properties by comparison to those in the case of non-administration of the test substance.

In the screening method of the present invention, unilateral ureteral obstruction means obstruction of ureter of one kidney. Ureter obstruction enables induction of necrosis of renal tubule and glomerulus in the kidney parenchyma of the kidney subjected to obstruction, and subsequent inflammation and fibrosis, and finally, functional disorder of the kidney. In addition, transient kidney ischemia/reperfusion after uninephrectomy refers to isolation of one of the kidneys in advance, obstruction of the renal artery in the remaining kidney 2 weeks later to induce ischemia, and release of obstruction 30 min later to allow for reperfusion of the blood flow. This transient ischemia causes progression of necrosis of renal tubule along with mild fibrosis for about 3 days, due to which kidney function is degraded. Bilateral transient kidney ischemia/reperfusion refers to obstruction of the renal artery of both kidneys to induce ischemia without isolation of one of the kidneys, and release of obstruction 30 min later to allow for reperfusion of the blood flow.

As a test substance to be administered to a non-human mammal deficient in AIM expression, proteins, peptides, antibodies, non-peptide compounds, synthetic compounds, fermentation products, cell extracts, plant extracts, animal tissue extracts, plasma and the like can be used. The timing of administration of the test substance may be before or simultaneously with unilateral ureteral obstruction, transient kidney ischemia/reperfusion after uninephrectomy or bilateral transient kidney ischemia/reperfusion, or after observation of the aforementioned property following unilateral ureteral obstruction, transient kidney ischemia/reperfusion after uninephrectomy or bilateral transient kidney ischemia/reperfusion of a non-human mammal deficient in AIM expression. The administration method may be oral or parenteral. For oral administration, it can be administered by mixing with a feed or drinking water. As parenteral administration, intraperitoneal administration, intravenous injection, subcutaneous injection, intradermal injection, muscular injection, administration by drip injection and the like, rectal administration of suppository and the like can be mentioned. The administration may include a single administration or multiple administrations.

The property of a non-human mammal deficient in AIM expression, which is administered with a test substance is observed after administration of the test substance, generally 3 or 4 days or later, preferably 7 days or later, more preferably 14 days or later. Accumulation of necrotic renal tubule cells and renal parenchymal fibrosis associated therewith can be observed by staining a kidney tissue section of the kidney isolated from the aforementioned mammal with hematoxylin-eosin or Azan and hematoxylin, and converting the staining level thereof into numerical values. Disintegration of glomerular structure and the level of glomerular fibrosis can be observed, similar to the above, by staining a kidney tissue section of the aforementioned isolated kidney with hematoxylin-eosin or Azan and hematoxylin, and converting the staining level thereof into numerical values. The expression level of inflammatory cytokine in the kidney can be measured by quantitative RT-PCR and the like. Examples of the inflammatory cytokine to be measured here include MCP-1, IL-1β and IL-6. The ratio of macrophage in the kidney can be confirmed by identifying Mac-1 positive cells by flow cytometer and the like. BUN value can be observed by measuring the blood urea nitrogen concentration.

The observation results of the aforementioned property obtained as mentioned above are compared with those in the case of non-administration of the test substance. Alternatively, a correlational figure of the presence or absence of a kidney disease and the aforementioned properties is drawn in advance and the obtained observation results of the aforementioned properties may be compared with the correlational figure. Comparison is preferably performed based on the presence or absence of a significant difference.

When the obtained observation results of the aforementioned properties are improved than those in the case of non-administration of the test substance, the test substance can be selected as a prophylactic or therapeutic agent for kidney diseases. Here, being improved means that (i) the level of accumulation of necrotic renal tubule cells (level of hematoxylin-eosin staining, or Azan staining and hematoxylin staining) is significantly lower than that in the case of non-administration of the test substance, (ii) the level of disintegration of glomerular structure (level of hematoxylin-eosin staining, or Azan staining and hematoxylin staining) is significantly lower than that in the case of non-administration of the test substance, (iii) expression level of inflammatory cytokine in the kidney is significantly lower than that in the case of non-administration of the test substance, (iv) ratio of macrophage in the kidney is significantly lower than that in the case of non-administration of the test substance, (v) BUN value is significantly lower than that in the case of non-administration of the test substance, and (vi) survival rate is significantly higher than that in the case of non-administration of the test substance.

When the test substance selected in the above is used as a prophylactic or therapeutic agent for kidney diseases, it can be formulated in the same manner as in the AIMs of the present invention, and administered by a similar administration route and at a similar dose. The kidney diseases to be the target of the prophylactic or therapeutic agent may be similar to those mentioned above.

In addition, since a non-human mammal deficient in AIM expression is useful as an animal model of kidney diseases under conditions performing unilateral ureteral obstruction, transient kidney ischemia/reperfusion after uninephrectomy or bilateral transient kidney ischemia/reperfusion, the mammal can be used for the evaluation method of a prophylactic or therapeutic drug for kidney diseases. Therefore, the present invention also provides a method of evaluating a prophylactic or therapeutic effect of a prophylactic or therapeutic agent for a kidney disease, comprising using an animal obtained by subjecting a non-human mammal deficient in AIM expression to unilateral ureteral obstruction, transient kidney ischemia/reperfusion after uninephrectomy or bilateral transient kidney ischemia/reperfusion. Specifically, the evaluation method of the present invention comprises the following steps:

(1) a step of administering, under conditions performing unilateral ureteral obstruction, transient kidney ischemia/reperfusion after uninephrectomy or bilateral transient kidney ischemia/reperfusion, a prophylactic or therapeutic agent for kidney diseases to a non-human mammal deficient in AIM expression, (2) a step of observing any one or more items of the following properties of the non-human mammal deficient in AIM expression, which is administered with the prophylactic or therapeutic agent for a kidney disease:

(i) accumulation of necrotic renal tubule cells and renal parenchymal fibrosis,
(ii) disintegration and fibrosis of glomerular structure,
(iii) expression level of inflammatory cytokine in the kidney,
(iv) ratio of macrophage in the kidney,
(v) BUN value,
(vi) survival rate, (3) a step of evaluating an effect of a prophylactic or therapeutic agent for kidney diseases by comparison of any one ore more items of the aforementioned properties with those in the case of non-administration of the prophylactic or therapeutic agent for kidney diseases.

The prophylactic or therapeutic agent for a kidney disease to be administered to a non-human mammal deficient in AIM expression in the evaluation method of the present invention may be a known prophylactic or therapeutic agent for a kidney disease. Examples thereof include, but are not limited to, depressor (e.g., angiotensin-converting enzyme-inhibitor, angiotensin II receptor antagonist, calcium antagonist, rennin inhibitor, α blocker, β blocker etc.); diuretic (e.g., carbonic acid dehydrogenase inhibitor, loop diuretic, thiazide diuretic, antialdosterone drug, Potassium-sparing diuretic etc.); active type vitamin D3 preparation (e.g., calcitriol, alfacacildol, maxacalcitol, falecalcitriol etc.); oral adsorption carbon preparation (e.g., activated carbon etc.); potassium-correcting drug (e.g., sodium polystyrene sulfonate etc.); phosphorus adsorbent (e.g., calcium carbonate, calcium acetate, Sevelamer hydrochloride, lanthanum carbonate etc.), red blood cell hematopoiesis stimulation factor preparation (erythropoiesis stimulating agent, ESA) (e.g., erythropoietin preparation), amino acid infusion preparation and the like. The administration period, administration method, administration frequency and the like of a prophylactic or therapeutic agent for a kidney disease may be the same as those in the aforementioned screening method.

An observation method of the property to be observed by the evaluation method of the present invention may be performed according to the aforementioned description of the screening method. When the observation results of the aforementioned properties obtained by the evaluation method are improved by a larger degree than those by non-administration of a prophylactic or therapeutic agent for a kidney disease, the test substance can be evaluated as having a higher prophylactic or therapeutic effect as a prophylactic or therapeutic agent for kidney diseases. As used herein, being improved means the same as above.

In the below-mentioned Examples of the present invention, it was confirmed that the blood AIM concentration of a patient with chronic kidney disease is correlated with the kidney function (eGFR: glomerular filtration rate). Particularly, it was confirmed that the kidney function of a patient with a chronic kidney disease having a blood AIM concentration lower than a given level is degraded 2-3 years later. From the above, it is suggested that the prognosis of a patient with a chronic kidney disease can be predicted by measuring the blood AIM concentration of the test subject. Therefore, the present invention provides a method of predicting the prognosis of a patient with a kidney disease, comprising measuring a concentration of AIM in a sample of a subject.

While the test subject to whom the prediction method of the present invention is applicable is not particularly limited, for example, a test subject having a risk of developing acute renal failure or chronic kidney disease or suspected to have developed same can be mentioned. While the chronic kidney disease is not limited, it includes, for example, chronic nephritis, chronic renal failure, nephrotic syndrome, diabetic nephropathy, nephrosclerosis, IgA nephropathy, hypertensive nephropathy, nephropathy associated with a collagen disease or IgM nephropathy and the like.

A sample to be used for the prediction method of the present invention is not particularly limited as long as it is collected from the above-mentioned test subject, and comprises an AIM gene product (e.g., RNA, protein, cleavage product thereof and the like) to be the measurement target. Examples thereof include body fluids such as blood, plasma, serum, lymph fluid, urine, sweat, saliva, synovial fluid and the like or a fraction thereof, and cells contained therein, particularly macrophage and the like, preferably, blood, plasma, serum can be mentioned.

The AIM concentration of a sample collected from a test subject can be measured by preparing an RNA (e.g., total RNA, mRNA) fraction from the aforementioned sample, and measuring a transcription product of AIM gene contained in the fraction. While an RNA fraction can be prepared by using a known method such as guanidine-CsCl ultracentrifugation method, AGPC method and the like, highly pure total RNA can be prepared rapidly and conveniently from a trace amount of macrophage by using a commercially available RNA extraction kit (e.g., RNeasy Mini Kit; manufactured by QIAGEN etc.). Examples of the method for detecting a transcription product of AIM gene in an RNA fraction include a method using hybridization (Northern blot, dot blot, DNA chip analysis etc.), a method using PCR (RT-PCR, competitive PCR, real-time PCR etc.) and the like. Quantitative PCR methods such as competitive PCR, real-time PCR and the like are preferable since variation in the expression of AIM gene can be detected rapidly, conveniently and highly quantitatively from a trace amount of macrophage.

When Northern blot or dot blot hybridization is employed, a transcription product of AIM gene can be measured by using a nucleic acid (probe) capable of hybridization with a transcription product of the gene. Examples of such nucleic acid include a nucleic acid capable of hybridization with a nucleic acid comprising a base sequence shown by a transcription product of AIM gene (e.g., base sequence shown in SEQ ID NO: 1) under highly stringent conditions. The highly stringent conditions are the aforementioned conditions and the like. More preferably, a nucleic acid comprising a base sequence complementary to a base sequence shown by a transcription product of AIM gene (e.g., base sequence shown in SEQ ID NO: 1) can be mentioned.

The nucleic acid to be used as a probe may be double-stranded or single-stranded. In the case of a double-stranded nucleic acid, it may be a double-stranded DNA, a double-stranded RNA, or a DNA:RNA hybrid. In the case of a single strand, an antisense strand can be used. While the length of the nucleic acid is not particularly limited as long as it can specifically hybridize with a target nucleic acid, for example, it is not less than about 15 bases, preferably not less than about 30 bases. The nucleic acid is preferably labeled with a labeling agent to enable detection and quantification of the target nucleic acid. As the labeling agent, for example, radioisotopes, enzymes, fluorescent substances, luminescent substances and the like are used. As the radio-isotope, for example, [$^{32}$P], [$^{31}$H], [$^{14}$C] and the like are used. As the enzymes described above, stable enzymes with a high specific activity are preferred; for example, beta-galactosidase, beta-glucosidase, alkaline phosphatase, peroxidase, malate dehydrogenase and the like are used. As the fluorescent substance, for example, fluorescamine, fluorescein isothiocyanate and the like are used. As the luminescent substances, for example, luminol, luminol derivatives, luciferin, lucigenin and the like are used. Furthermore, biotin-(strept)avidin can also be used for binding a probe and a label.

When Northern hybridization is employed, an RNA fraction prepared as mentioned above is separated by gel electrophoresis, transferred onto a membrane of nitrocellulose, nylon, polyvinylidenedifluoride and the like, allowed to hybridize under the above-mentioned highly stringent conditions in a hybridization buffer comprising a labeling probe prepared as mentioned above, and the amount of the label bound to the membrane is measured for each band by a suitable method, whereby the expression level of AIM gene can be measured. Also, in the case of dot blot, the expression level of AIM gene can be measured by subjecting a membrane spotted with RNA fractions to a hybridization reaction in the same manner and measuring the amount of the label of the spot.

In another preferable embodiment, a quantitative PCR method is used as a method for measuring AIM concentration. Examples of the quantitative PCR include competitive PCR, real-time PCR and the like.

A set of oligonucleotides used as primers in PCR is not particularly limited as long as they can each specifically hybridize with a sense strand (coding strand) and an antisense strand (noncoding strand) of a transcription product of the AIM gene, and can amplify the DNA fragment sandwiched by them. For example, a set of oligoDNAs each having a length of about 15-about 100 bases, preferably about 15-about 50 bases, and designed to amplify about 100 bp-1 kbp DNA fragments can be mentioned. More specifically, as a set of oligonucleotides used as primers, a nucleic acid capable of hybridizing with a nucleic acid (antisense strand) comprising the base sequence complementary to the aforementioned base sequence under highly stringent conditions can be mentioned. As used herein, the highly stringent conditions are as defined above. More preferably, a nucleic acid comprising a base sequence complementary to a base sequence shown in SEQ ID NO: 1, and a nucleic acid comprising a base sequence complementary to a base sequence of the nucleic acid can be mentioned.

In competitive RT-PCR, the amount of desired DNA is determined by allowing a known amount of another template nucleic acid that can be amplified by a set of primers capable of amplifying the desired DNA, as the competitor, to coexist in the reaction liquid to cause a competitive amplification reaction, and comparing the amounts of the amplification products. Therefore, when competitive RT-PCR is used, in addition to the above-mentioned primer set, a known amount of a competitor nucleic acid that can be amplified with the primer set, and can be distinguished from an amplification product of the target nucleic acid (i.e., transcription product of AIM gene) after the amplification (e.g., different amplification size, different migration pattern of restriction enzyme treated fragment and the like) is used. Since amplification occurs competitively as the target nucleic acid and the competitor nucleic acid struggle for the primers, the quantitative ratio of the amplification product reflects the quantitative ratio of the original template. The competitor nucleic acid may be DNA or RNA. In the case of DNA, a cDNA is synthesized from an RNA fraction prepared as mentioned above by a reverse transcription reaction, and PCR may be performed in the co-presence of the above-mentioned primer set and competitor. In the case of RNA, competitor is added to an RNA fraction and a reverse transcription reaction is performed, and the above-mentioned primer set is added and PCR is performed. In the latter case, the absolute amount of the original mRNA can be estimated because the reverse transcription reaction efficiency is also taken into consideration.

In real-time PCR, on the other hand, the amplification amount is monitored in real-time using a fluorescent reagent, and an apparatus integrally comprising a thermal cycler and a spectrofluoro-photometer is necessary. Such apparatus is commercially available. There are several methods depending on the fluorescent reagent to be used and, for example, intercalator method, TaqMan™ probe method, Molecular Beacon method and the like can be mentioned. In any case, cDNA is synthesized by reverse transcription reaction from an RNA fraction prepared as mentioned above, and the above-mentioned primer set and a fluorescence reagent (probe), reagents (intercalator) emitting fluorescence by binding to double stranded DNA such as SYBR Green I, ethidium bromide and the like, nucleic acids usable as the above-mentioned probes (the nucleic acid hybridizes to the target nucleic acid within amplification region), wherein the both ends are respectively modified with a fluorescent substance (e.g., FAM, HEX, TET, FITC etc.) and a quenching substance (e.g., TAMRA, DABCYL etc.) (TaqMan™ probe or Molecular Beacon probe) and the like, are each added to PCR reaction system. Since intercalator binds to a synthesized double stranded DNA and emits fluorescence upon irradiation of excitation light, the amount of an amplification product can be monitored by measuring the intensity of fluorescence, based on which the amount of original template cDNA can be assumed. The TaqMan™ probe is an oligonucleotide capable of hybridizing to an amplification region of the target nucleic acid, which has both ends modified by a fluorescent substance and a quenching substance, respectively. It hybridizes to a target nucleic acid during annealing but is prohibited from emitting fluorescence by the presence of the quenching substance, and emits fluorescence when decomposed by the exonuclease activity of DNA polymerase during elongation, which releases the fluorescent substance. Therefore, by measuring fluorescence intensity, the amount of the amplification product can be monitored, based on which the amount of original template cDNA can be assumed. The Molecular Beacon probe is an oligonucleotide capable of hybridizing to an amplification region of a target nucleic acid and having a hairpin type secondary structure, which has both ends modified by a fluorescent substance and a quenching substance, respectively. When it has a hairpin structure, it does not emit fluorescence due to the presence of a quenching substance, and emits fluorescence when the distance between the fluorescent substance and the quenching substance grows upon hybridization to the target nucleic acid during annealing. Therefore, the amount of the amplification product can be monitored by measuring the fluorescence intensity, based on which the amount of original template cDNA can be assumed. Since real-time RT-PCR permits real-time monitoring of the amplification amount of PCR, it does not require electrophoresis and can analyze the expression of AIM gene more rapidly.

In another embodiment, the AIM concentration of a sample collected from a test subject can be measured by preparing protein fractions from the sample and detecting AIM contained in the fraction. Detection of AIM can be performed by an immunological measurement method (e.g., ELISA, FIA, RIA, Western blot etc.) using an antibody to AIM. Alternatively, detection of AIM can also be performed by a mass spectrometry method such as MALDI-TOFMS and the like.

An antibody to AIM can be obtained according to a generally-used technique for producing a polyclonal antibody or monoclonal antibody, and using a protein comprising an amino acid sequence that is the same or substantially the same as the amino acid sequence shown in SEQ ID NO: 2 or SEQ ID NO: 4, or a partial amino acid sequence thereof as an immunization antigen.

In applying these individual immunological measurement methods to the diagnosis method of the present invention, it is unnecessary to set special conditions, procedures and the like. Making ordinary technical considerations for those skilled in the art to the ordinary conditions and procedures in each method, a measurement system for AIM can be constructed. For details of these general technical means, compendia, books and the like can be referred to. For example, Hiroshi Irie, ed., "Radioimmunoassay" (Kodansha Ltd., published in 1974), Hiroshi Irie, ed., "Sequel to the Radioimmunoassay" (Kodansha Ltd., published in 1979), Eiji Ishikawa et al., ed., "Enzyme Immunoassay" (Igakushoin, published in 1978), Eiji Ishikawa et al., ed., "Enzyme Immunoassay" (2nd ed.) (Igakushoin, published in 1982), Eiji Ishikawa et al., ed., "Enzyme Immunoassay" (3rd ed.) (Igakushoin, published in 1987), Methods in ENZYMOLOGY, Vol. 70 (Immunochemical Techniques (Part A)), ibidem, Vol. 73 (Immunochemical Techniques (Part B)), ibid., Vol. 74 (Immunochemical Techniques (Part C)), ibid., Vol. 84 (Immunochemical Techniques (Part D: Selected Immunoassays)), ibidem, Vol. 92 (Immunochemical Techniques (Part E: Monoclonal Antibodies and General Immunoassay Methods)), ibidem, Vol. 121 (Immunochemical Techniques (Part I: Hybridoma Technology and Monoclonal Antibodies)) (all published by Academic Press Publishing) and the like.

The prediction method of the present invention may be specifically a method including the following steps.
(1) a step of measuring AIM concentration of samples of healthy human and test subject,
(2) a step of comparing AIM concentration measured in healthy human and AIM concentration measured in test subject.

As mentioned above, in patients with a chronic kidney disease, the kidney function of a patient having a chronic kidney disease and showing an lower blood concentration of AIM in the present invention than a given level is degraded 2-3 years later. Therefore, as mentioned above, when the AIM concentration measured is lower than that of healthy human or a given level, the chronic kidney disease of the test subject can be judged to be highly possibly degraded in the future. Alternatively, a correlation figure of degradation of chronic kidney diseases and AIM concentration is drawn in advance and the obtained observation results may be compared with the correlational figure. Comparison is preferably performed based on the presence or absence of a significant difference.

The prediction method of the present invention may include, in addition to the above-mentioned steps (1) and (2), (3) a step of judging that the chronic kidney disease of the test subject is highly possibly degraded in the future when the AIM concentration of the test subject is significantly higher than that of healthy human.

Furthermore, in the below-mentioned Examples of the present invention, a significantly high concentration of AIM was found, as compared to healthy individual, in the urine of patients with acute renal failure and mouse subjected to bilateral transient kidney ischemia/reperfusion. From the above, it is suggested that acute renal failure can be examined by measuring the AIM concentration of urine of the test subject. Therefore, the present invention provides a test method of acute renal failure, comprising measuring a concentration of AIM in a sample of a subject.

While the test subject to whom the test method of the present invention is applicable is not particularly limited, for example, a test subject having a risk of developing acute renal failure or suspected to have developed same can be mentioned. The sample usable for the test method of the present invention is as described for the method of predicting prognosis of a patient with a kidney disease of the present invention, and preferably, urine can be mentioned. In addition, the measurement of the AIM concentration of a sample collected from a test subject is as described for the method of predicting prognosis of a patient with a kidney disease of the present invention.

The test method of the present invention may be specifically a method including the following steps.
(1) a step of measuring AIM concentration of samples of healthy human and test subject,
(2) a step of comparing AIM concentration measured in healthy human and AIM concentration measured in test subject.

As mentioned above, the urine concentration of AIM of the present invention is significantly high in patients with acute renal failure than in healthy human. Therefore, when AIM concentration is measured as mentioned above and the results show a significantly high concentration as compared to healthy human, the test subject can be judged to have developed acute renal failure. Alternatively, a correlational figure of the presence or absence of acute renal failure and AIM concentration is drawn in advance and the obtained observation results may be compared with the correlational figure. Comparison is preferably performed based on the presence or absence of a significant difference.

The test method of the present invention may include, in addition to the above-mentioned steps (1) and (2), (3) a step of judging that the test subject is affected with acute renal failure when the AIM concentration of the test subject is significantly higher than that of healthy human.

Furthermore, the present invention also covers a kit for the diagnosis or prognosis prediction of kidney diseases. The kit is not particularly limited as long as it is a kit for conveniently carrying out the aforementioned test method or prediction method of the present invention. The kit contains
(a) a nucleic acid probe or nucleic acid primer hybridizable with a transcription product of AIM gene, and/or
(b) antibody to AIM.

When the kit contains two or more of the above-mentioned nucleic acids and/or antibodies, each nucleic acid or antibody can specifically recognize mutually different regions on the base sequence of AIM gene, or can specifically recognize different epitopes of a translational product of the AIM gene.

When the kit of the present invention contains a reagent containing the nucleic acid of the aforementioned (a) in the constitution, the nucleic acid for probe or oligonucleotide for primer mentioned above for the test method or prediction method of the present invention can be mentioned as the nucleic acid.

The nucleic acid capable of detecting the expression of AIM gene can be provided as a solid in a dry state or alcohol precipitate, or in a dissolution state in water or suitable buffer (e.g.: TE buffer etc.). When it is used as a labeling probe, the nucleic acid can be provided in the state of being labeled with any of the above-mentioned labeling substances in advance, or can also be provided independently from the labeling substance and labeled when in use.

Alternatively, the nucleic acid can also be provided in the state of being immobilized on a suitable solid phase. Examples of the solid phase include, but are not limited to, glass, silicon, plastic, nitrocellulose, nylon, polyvinylidenedifluoride and the like. Examples of the immobilization means include, but are not limited to, methods including previously introducing a functional group such as amino group, aldehyde group, SH group, biotin and the like into a nucleic acid, introducing a functional group capable of reacting with the nucleic acid (e.g.: aldehyde group, amino group, SH group, streptavidin and the like) also on the solid phase, and crosslinking the solid phase and the nucleic acid by a covalent bond between the both functional groups, or polycation coating solid phase relative to polyanionic nucleic acid, and immobilizing the nucleic acid via electrostatic binding and the like.

The nucleic acid contained in the kit is particularly preferably constructed to be able to detect expression of AIM gene by the same method (e.g.: Northern blot, dot blot, DNA array technique, quantification RT-PCR etc.).

When the kit of the present invention contains a reagent containing the antibody of the aforementioned (b) in the constitution, the antibody mentioned above for the test method or prediction method of the present invention can be mentioned as the antibody.

The reagent constituting the kit of the present invention can further contain, in addition to nucleic acid and antibody capable of detecting the expression of AIM gene, other substance necessary for the reaction for detecting the expression of the gene, which does not adversely influence the reaction when preserved in co-existence. Alternatively, the reagent may also be provided with a separate reagent containing other substance necessary for the reaction for detecting the expression of the AIM gene. For example, when the reaction for detecting the expression of the AIM gene is PCR, examples of such other substance include reaction buffer, dNTPs, heat-resistant DNA polymerase and the like. When competitive PCR and real-time PCR are used, competitor nucleic acid, fluorescence reagent (the above-mentioned intercalator, fluorescence probe etc.) and the like can be further contained. When the reaction for detecting the expression of the AIM gene is an antigen antibody reaction, examples of such other substance include reaction buffer, competitor antibody, labeled secondary antibody (e.g., when primary antibody is rabbit anti-human AIM antibody, mouse anti-rabbit IgG labeled with peroxidase, alkaliphosphatase etc. and the like), blocking solution and the like.

The sequence identification numbers in the sequence listing herein show the following sequences.
[SEQ ID NO: 1]
Shows the base sequence of human AIM.
[SEQ ID NO: 2]
Shows the amino acid sequence of human AIM.
[SEQ ID NO: 3]
Shows the base sequence of cat AIM.
[SEQ ID NO: 4]
Shows the amino acid sequence of cat AIM.

[SEQ ID NO: 5]
Shows the complementary sequence of transcription product of cat AIM.
[SEQ ID NO: 6]
Shows the amino acid sequence of mouse AIM.

EXAMPLES

The present invention is hereinafter described more specifically by means of the following Examples and Reference Examples, to which the invention is not limited.

Example 1: Suppression of Progression of Chronic Renal Failure or Renal Fibrosis by AIM One of the frequently-used kidney diseases models using animal is a unilateral ureteral obstruction (DUO) model. In this case, unilateral ureter obstruction induces gradual necrosis of renal tubule and glomerulus in the kidney parenchyma subjected to obstruction, and subsequent inflammation and fibrosis, and finally, functional disorder of the kidney. AIM knockout mouse (AIM-KO) and wild-type mouse (WT) were each subjected to UUO and progress was observed (n=6 for each) (FIG. 1A). The structure of normal kidney was not different at all between WT and AIM-KO. However, when UUO kidney on day 14 was subjected to simultaneous fiber staining by Azan staining and hematoxylin staining, WT showed spreading fibrosis, but a considerable number of glomeruluses and renal tubules still maintained a normal structure, and many renal tubules were non-necrotic. In contrast, AIM-KO showed accumulation of necrotic renal tubule cells over a wide range, destroyed glomerular structure, and already disintegrated kidney parenchymal structure. Similar results were obtained in all mice observed.

Similarly, AIM-KO and WT mouse were each subjected to UUO, and the kidney was observed by HE, PAS, Azan staining on day 14 (n=6 for each) (FIG. 1B). WT showed spreading fibrosis, but a considerable number of glomeruluses and renal tubules still maintained a normal structure (HE, Azan staining). On the other hand, AIM-KO showed progress of fibrosis, destroyed glomerular structure, and already disintegrated kidney parenchymal structure. PAS staining revealed necrotic cell masses (PAS positive) accumulated over a wide range inside and outside renal tubule in AIM-KO mouse. Similar results were obtained in all mice observed.

Example 2: Suppression of Progression of Acute Renal Failure (Up to Day 7) to Chronic Renopathy (Becoming Chronic Renal Failure) (Day 14) by AIM Another kidney disease model is a transient kidney ischemia/reperfusion (IR) model. Transient kidney ischemia/reperfusion involves isolation of one of the kidneys in advance, obstruction of the renal artery in the remaining kidney to induce ischemia, and release of obstruction 30 min later to allow for reperfusion of the blood flow. This transient ischemia causes progression of necrosis of renal tubule along with mild fibrosis for about 3 days, due to which kidney function is degraded. AIM knockout mouse (AIM-KO) and wild-type mouse (WT) were each subjected to IR and progress was observed (FIG. 2). In WT, after degradation of kidney function, necrotic cells were removed, non-necrotic renal tubules rapidly divided, and almost normal renal tubular structure was recovered 14 days later. Along therewith, the kidney function became normal. In AIM-KO, while initial damage level of renal tubule was not different from WT, removal of necrotic cells did not proceed, and necrotic cells were accumulated. Since removal of necrotic cells did not proceed, division of new renal tubule cells was suppressed, and secondary inflammation and fibrosis progressed. The experiment was performed with N=6, and similar results were obtained in all mice. That is, from the results of Example 1 and Example 2, it was clarified that absence of AIM leads to the accumulation of necrotic renal tubule cells, and markedly impaired repair of the structure and function of the kidney.

Example 3: Suppression of Prolonged Inflammation (Renopathy Becoming Chronic) after Acute Renal Failure by AIM The transient kidney ischemia/reperfusion (IR) performed in Example 2 was applied to wild-type mouse (WT) and AIM knockout mouse (AIM-KO), and postoperative infiltration of inflammatory macrophage was observed by immunostaining of macrophage marker F4/80 (FIG. 3A). On day 3 postoperation, AIM KO mouse showed clearly-promoted F4/80 positive macrophage infiltration as compared to WT. On day 14 postoperation, WT showed reduced macrophage infiltration, but AIM KO mouse showed further aggravation. It was clarified by quantitative RT-PCR experiment that, along with the progress of macrophage infiltration, expression of MCP-1, one of inflammatory cytokines, similarly increased significantly in the kidney of AIM KO mouse (FIG. 3B). The experiment was performed with N=6, and similar results were obtained in all mice.

Example 4: Recovery of Acute Renal Failure by AIM

IR performed in Example 2 was applied to AIM-KO mouse, recombinant AIM (rAIM) or PBS was intraperitoneally administered each by 100 μg (n=6 for each) on day 3, day 4 and day 7 when the kidney function is transiently most degraded, and the progress was observed (FIG. 4). In PBS administration group, similar results as in Example 2 were obtained and accumulation of necrotic cells, destruction of glomerulus and the like proceeded thereafter, and the kidney function (BUN value) was improved somewhat from day 3 but was not recovered to the normal value, and gradually degraded later. However, in the rAIM administration group, after rAIM administration on day 3, the BUN value was significantly improved and already returned to the normal range on day 7, followed by further decrease. Histologically, necrotic renal tubule cells were removed by day 7, and the structure of kidney parenchyma also became normal. That is, it was clarified that AIM administration can promote removal of necrotic cells, accelerate regeneration of renal tubule, and recover kidney function.

Figure 5:
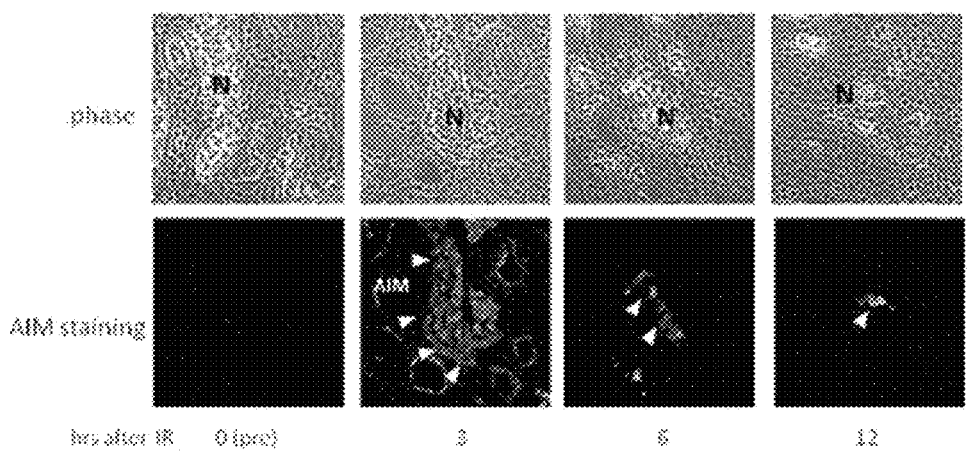
FIG. 5 shows phase-contrast image and immunostaining images of AIM of kidney tissue sections of AIM KO mouse that underwent transient kidney ischemia/reperfusion after uninephrectomy and administration of rAIM. N: necrotic focus. arrow: AIM.

Example 5: Attachment of AIM to Necrotic Renal Tubular Epithelial Cell Mass Due to Acute Renal Failure and Removal of Necrotic Focus AIM-KO mouse was applied to IR performed in Example 2, rAIM (100 μg) was intravenously administered postoperationally, and kidney sections were stained with an anti-AIM antibody 3, 6, 12 hr later. At 3 hr after AIM administration, strong attachment of AIM to necrotic renal tubule was confirmed (FIG. 5, upper panel: in phase-contrast micrograph, necrotic focus is indicated with N. FIG. 5, lower panel: AIM signal (arrow head) is observed overlapping necrotic focus). With the progress of time, necrotic focus region reduced, and almost only a trace could be confirmed 12 hr later. That is, in the recovery of kidney function by AIM after IR (Example 4), it is considered that attachment of AIM to necrotic focus accelerated removal thereof, along with which inflammation was suppressed and tissue regeneration was progressed.

Example 6: Emergence of Urine AIM after Acute Renal Failure

Figure 6:
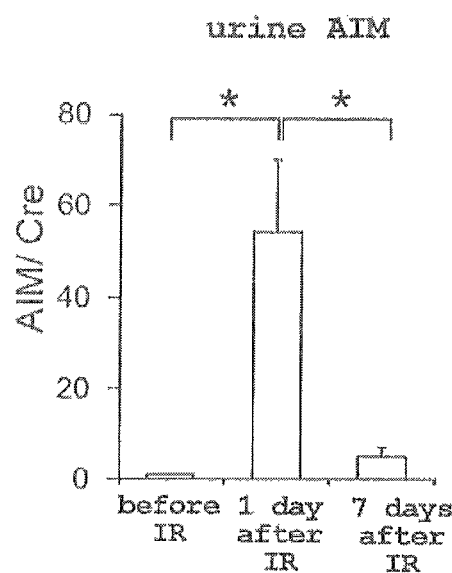
FIG. 6 is a graph showing urine AIM level of WT mouse that underwent bilateral transient kidney ischemia/reperfusion. *: p<0.05

On the urine of wild-type mouse (WT) applied to bilateral transient kidney ischemia/reperfusion (IR), wherein the renal artery of both kidneys is obstructed to induce ischemia without isolation of one of the kidneys, detection was performed on day 1 and day 7 after IR by ELISA method (FIG. 6). AIM was scarcely detected (before IR) in the mouse urine in normal state, but a large amount of AIM was detected in the urine on day 1 after IR when renopathy is most drastic. Along with the recovery of renopathy, urine AIM decreased (on day 7 after IR). Since urine discharged during renopathy due to IR becomes diluted urine, urine AIM value was normalized with urine creatinine value.

Example 7: Aggravation of Acute Renal Failure Due to Lack of AIM (Survival Rate)

Figure 7:
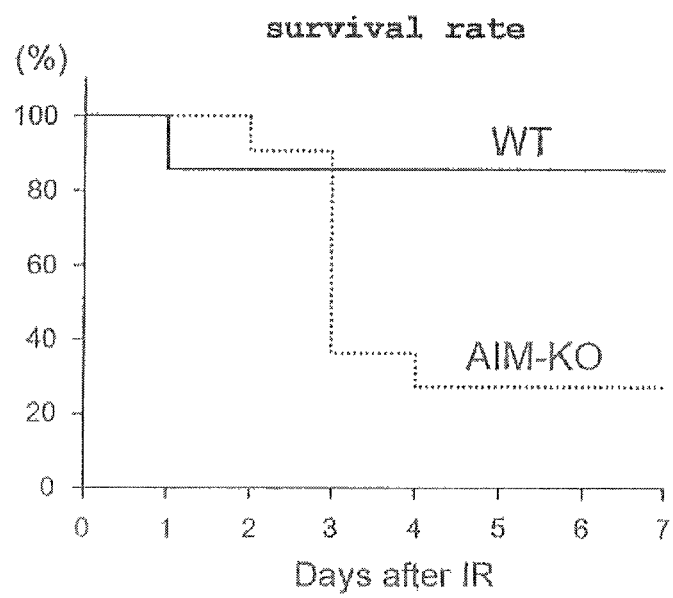
FIG. 7 is a graph showing the survival rate of AIM KO mouse and WT mouse that underwent bilateral transient kidney ischemia/reperfusion.

WT and AIM-KO mice were subjected to bilateral IR and the survival rate was examined (n=8 each) (FIG. 7). On day 7 after IR, under the condition that not less than 80% of WT survived, the survival rate of AIM-KO was 30% or below, and most of the dead mice died by day 3 after IR.

Example 8: Clinical Score

Figure 8:
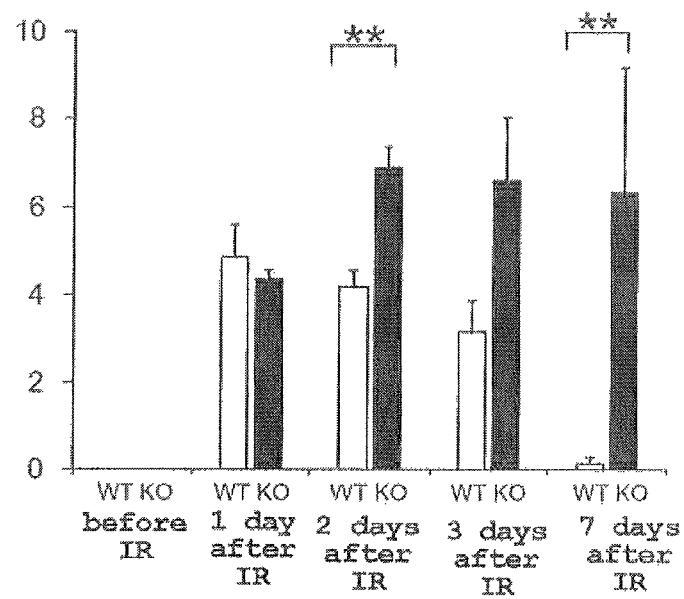
FIG. 8 is a graph showing clinical scores of AIM KO mouse and WT mouse that underwent bilateral transient kidney ischemia/reperfusion. **: p<0.01

WT and AIM-KO mice were subjected to bilateral IR, and the clinical score was analyzed over time (FIG. 8). The clinical score was taken by adding (0: no abnormality, 1: mild symptom, 2: moderate symptom, 3: severe symptom) for the lack of prompt movement, eye opacity, decrease in reactivity to pain stimulation on the tail, poor coat of fur, and the total thereof was graphically shown. In WT, the score reached the maximum value on day 1 after IR and gradually alleviated; however, in AIM-KO, the score remained high.

Example 9: Kidney Dysfunction Associated with Acute Renal Failure (BUN Value)

Figure 9:
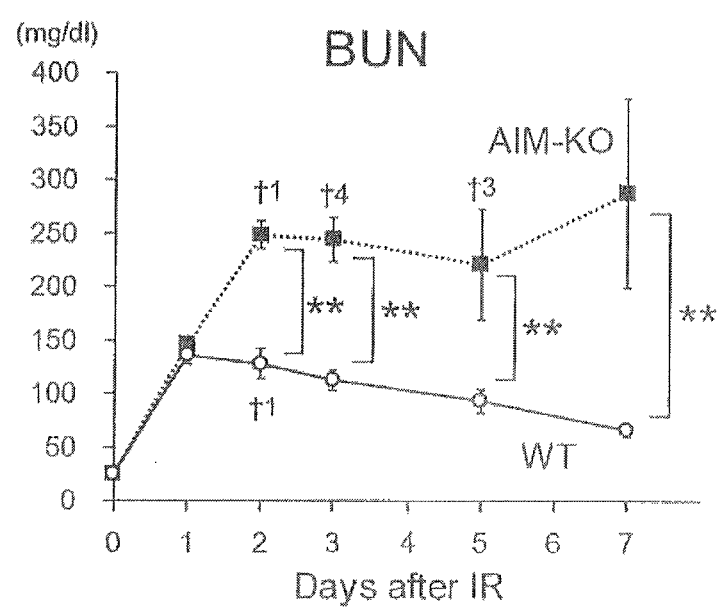
FIG. 9 is a graph showing the BUN value of AIM KO mouse and WT mouse that underwent bilateral transient kidney ischemia/reperfusion. The number of mice that died each day is indicated with +. *: P<0.05, **: P<0.01

WT and AIM-KO mice were subjected to bilateral IR, and BUN which is a marker of kidney function was measured over time (n=8) (FIG. 9). Similar to the clinical scores in Example 8, BUN reached the peak on day 1 in WT and decreased thereafter; however, in AIM-KO, it increased up to day 2 and a marked decrease was not observed thereafter.

Example 10: Kidney Dysfunction Associated with Acute Renal Failure (Kidney Tissue: PAS Staining)

Figure 10:
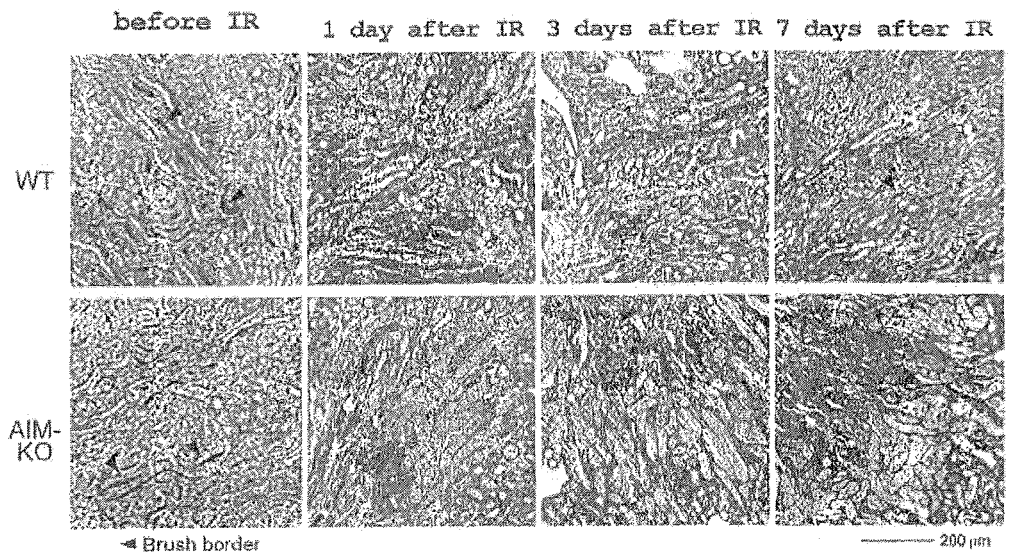
FIG. 10 shows PAS staining images of kidney tissue sections of AIM KO mouse and WT mouse that underwent bilateral transient kidney ischemia/reperfusion.

WT and AIM-KO mice were subjected to bilateral IR, and the kidney tissue was analyzed by PAS staining over time (FIG. 10). Similar to the clinical scores in Example 8 and BUN value in Example 9, kidney dysfunction reached the peak on day 1 in WT and recovered thereafter, and proximal renal tubule epithelium having a normal renal tubular structure and brush border (brush border; arrowhead) was regenerated on day 7. In AIM-KO, however, the disorder was continued, and PAS-positive dead cell mass was accumulated in the proximal renal tubule and was not removed even on day 7.

Figure 11:
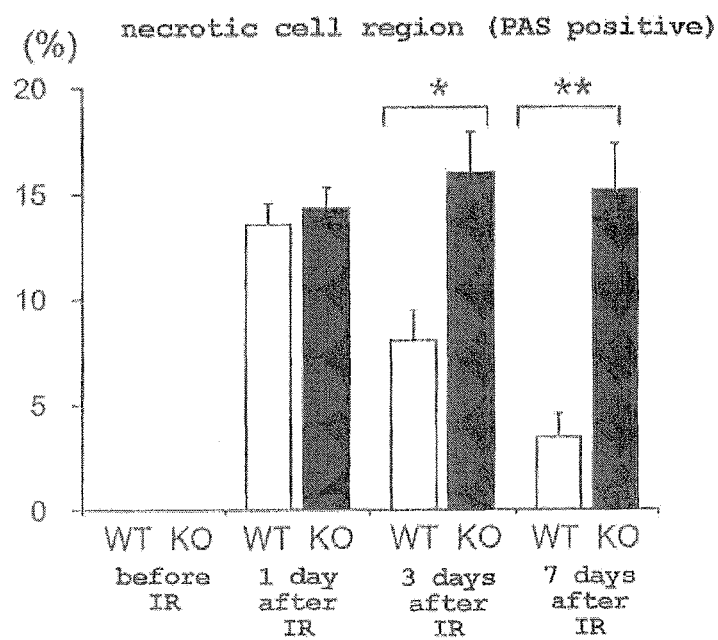
FIG. 11 is a graph showing the ratio of the area of dead cell mass in proximal renal tubule in kidney tissue sections of AIM KO mouse and WT mouse that underwent bilateral transient kidney ischemia/reperfusion, relative to the total area per one section. *: p<0.05, **: p<0.01

Example 11: Quantification of Renal Tubular Epithelial Cell Mass that Became Necrotic Due to Acute Renal Failure The area of dead cell mass of epithelial cells in the proximal renal tubule observed in FIG. 10 was quantified by calculating as a ratio relative to the total area of one section (n=3-5) (FIG. 11). A profile similar to the finding obtained in Examples 8-10 was shown, and accumulation and remaining of dead cell mass was clear in AIM-KO.

Example 12: Prolonged Inflammation of Acute Renal Failure by AIM (Inflammatory Cytokine)

Figure 12:
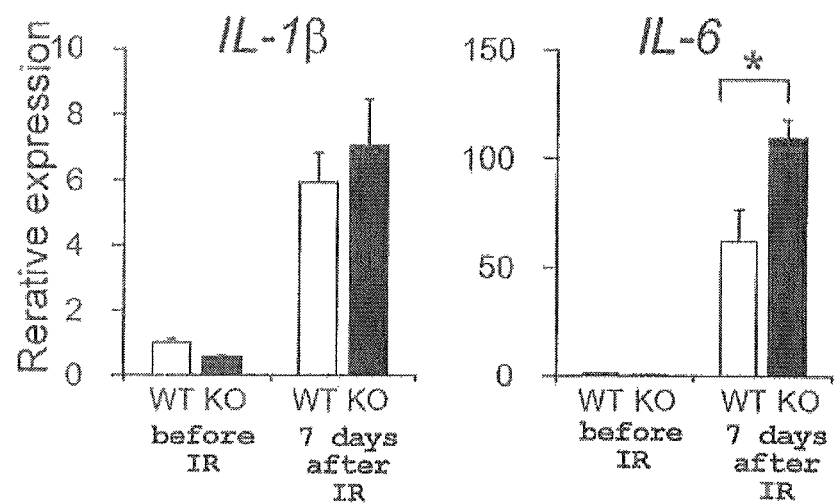
FIG. 12 is a graph showing the mRNA expression ratio of IL-1b and IL-6 in AIM KO mouse and WT mouse that underwent bilateral transient kidney ischemia/reperfusion by quantitative RT-PCR. *: p<0.05

WT and AIM-KO mice were subjected to bilateral IR, RNA was extracted from the kidney before IR and on day 7 after IR, and inflammatory cytokines IL-1β and IL-6 were analyzed by quantitative RT-PCR (n=3 each) (FIG. 12). The both markers showed high values in AIM-KO as compared to WT, and prolonged inflammation associated with kidney tissue destruction by IR was suggested.

Example 13: Prolonged Inflammation of Acute Renal Failure by AIM (Infiltrating Macrophage)

Figure 13:
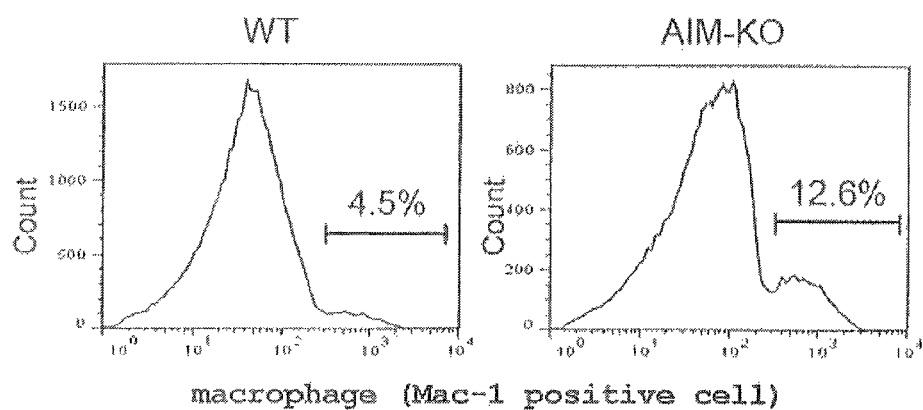
FIG. 13 shows flow cytometer analysis results of the cells derived from kidney of AIM KO mouse and WT mouse that underwent bilateral transient kidney ischemia/reperfusion on day 7 after IR.

WT and AIM-KO mice were subjected to bilateral IR, the kidney on day 7 after IR was subjected to a collagenase treatment and analyzed by flow cytometer to examine the ratio of macrophage (Mac-1 positive cells) (FIG. 13). Similar to the results of Example 12, the ratio of macrophage in the kidney was high in AIM-KO as compared to WT. Each 3 mice were analyzed, and similar results were obtained. FIG. 13 shows representative results.

Figure 14:
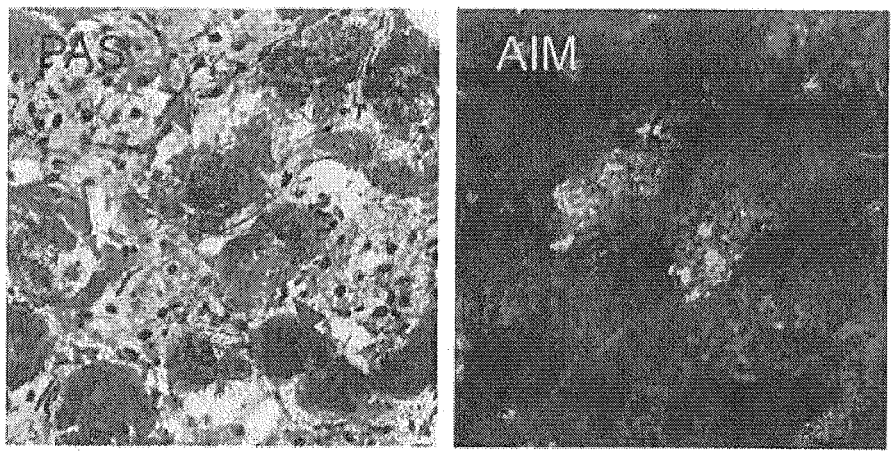
FIG. 14 shows PAS staining images and immunostaining images with an anti-AIM antibody of kidney tissue sections of WT mouse that underwent bilateral transient kidney ischemia/reperfusion.

Example 14: Accumulation of AIM in Epithelial Cell Mass in Mouse Renal Tubule that Became Necrotic Due to Acute Renal Failure Serial kidney sections of WT mouse that underwent bilateral IR were subjected to PAS staining (left) and immunostaining with an anti-AIM antibody (right) (FIG. 14). Accumulation of AIM on many dead cell mass (white) was observed.

Figure 15:
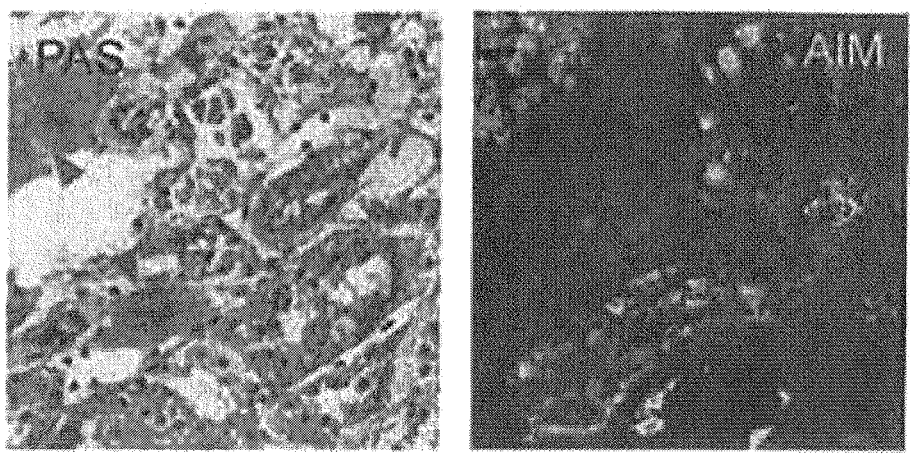
FIG. 15 shows PAS staining image and immunostaining images by an anti-AIM antibody of kidney tissue sections of a human who died of acute renal failure due to kidney infarction.

Example 15: Accumulation of AIM in Necrotic Epithelial Cell Mass in Mouse Renal Tubule of Patients with Acute Renal Failure Serial kidney sections of human patients who died of acute renal failure due to kidney infarction were subjected to PAS staining (left) and immunostaining with an anti-AIM antibody (right) (FIG. 15). Similar to IR mouse in Example 14, accumulation of AIM on many dead cell mass (white) was observed.

Figure 16:
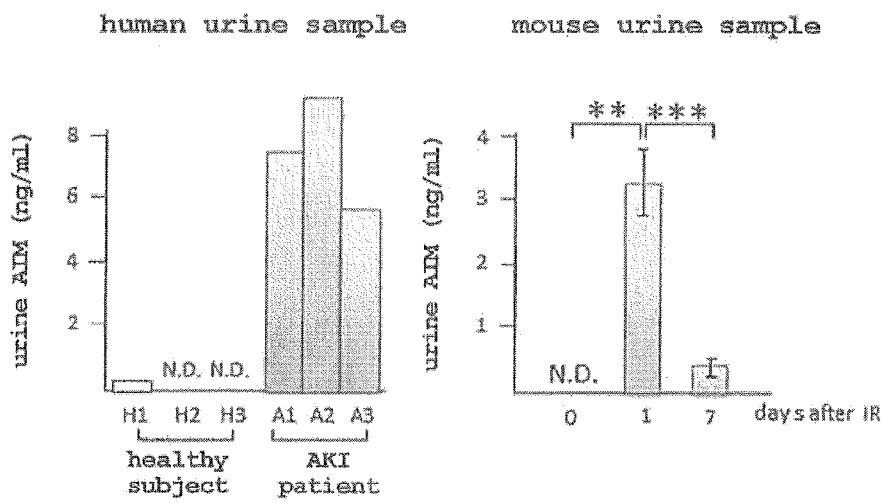
FIG. 16 is a graph showing AIM concentration of urine before IR, one day after IR, and 7 days later as measured by ELISA of 3 patients transported to hospital due to human acute renal failure (AKI), 3 healthy individuals, and 5 WT mice subjected to bilateral IR. N.D.: not detected

Example 16: Detection of Urine AIM in Patients with Acute Renal Failure and Mouse with Acute Renal Failure AIM concentration of urine before IR, one day after IR, and 7 days later of 3 patients transported to hospital due to human acute renal failure (AKI), 3 healthy individuals, and 5 WT mice subjected to bilateral IR was analyzed by ELISA (FIG. 16). AIM was scarcely observed in the urine of healthy individual but observed in the urine of AKI patients. Also in mouse, it was not observed before IR, but a significant amount of AIM was observed in urine one day after IR when renopathy was remarkable, and the AIM amount decreased on day 7 when renopathy was improved.

Figure 17:
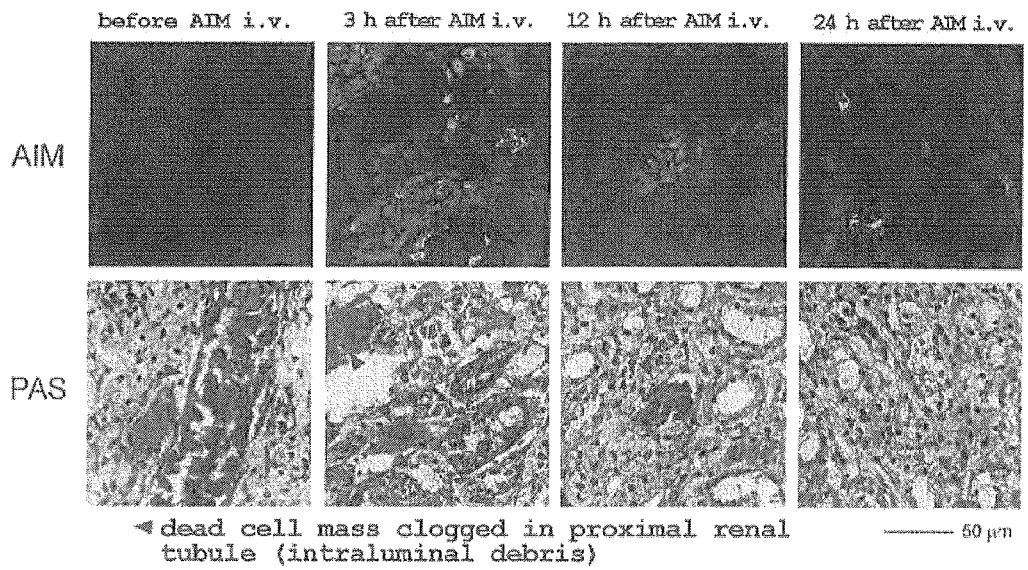
FIG. 17 shows over-time PAS staining images and immunostaining images by an anti-AIM antibody of kidney tissue sections of AIM KO mouse that underwent bilateral transient kidney ischemia/reperfusion.

Example 17: Shrinkage of Epithelial Cell Mass in Renal Tubule by AIM Accumulation AIM-KO mouse was subjected to bilateral IR, 200 μg of rAIM was administered on day 3 after IR, kidney sections obtained over time were subjected to PAS staining and immunostaining with an anti-AIM antibody (FIG. 17). Dead cell mass accumulated with AIM shrank rapidly.

Example 18: In Vitro Phagocytosis Assay (Experiment Using Kidney-Derived Macrophage)

Figure 18:
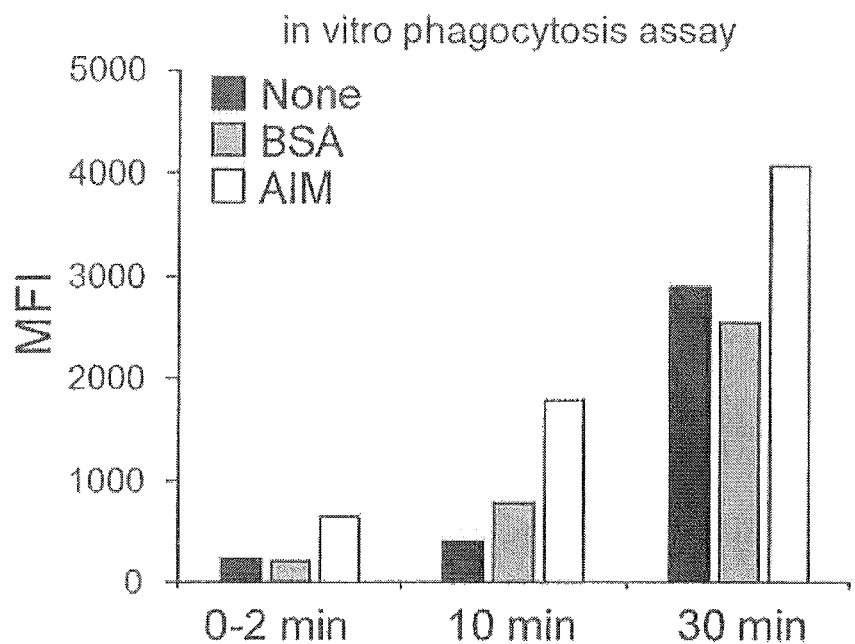
FIG. 18 is a graph showing phagocytic activity of F4/80 positive macrophage isolated by FACS sorter from the kidney treated with collagenase on day 3 after bilateral IR of AIM-KO mouse.

AIM-KO mouse was subjected to bilateral IR, the kidney on day 3 after IR was subjected to a collagenase treatment, F4/80 positive macrophage was isolated using FACS sorter, and the phagocytic activity thereof was analyzed (FIG. 18). As a target of phagocytosis, human renal tubule cell line HK2 cell was heat treated to undergo necrosis, labeled with FITC, coated with recombinant AIM (rAIM) or bovine serum albumin (BSA) and the obtained dead HK2 cells were used. As None, dead HK2 cells not coated with rAIM or BSA were used. Macrophage and the above-mentioned 3 kinds of dead HK2 cells were incubated, FITC positive dead HK2 cells uptaken by macrophage were analyzed by flow cytometer (FACS) over time. It was shown that dead HK2 cells coated with rAIM are phagocytosed by macrophage more highly efficiently than dead HK2 cells coated with BSA, or dead HK2 cells not coated therewith.

Example 19: In Vitro Phagocytosis Assay (Experiment Using Macrophage Derived from Bone Marrow)

Figure 19:
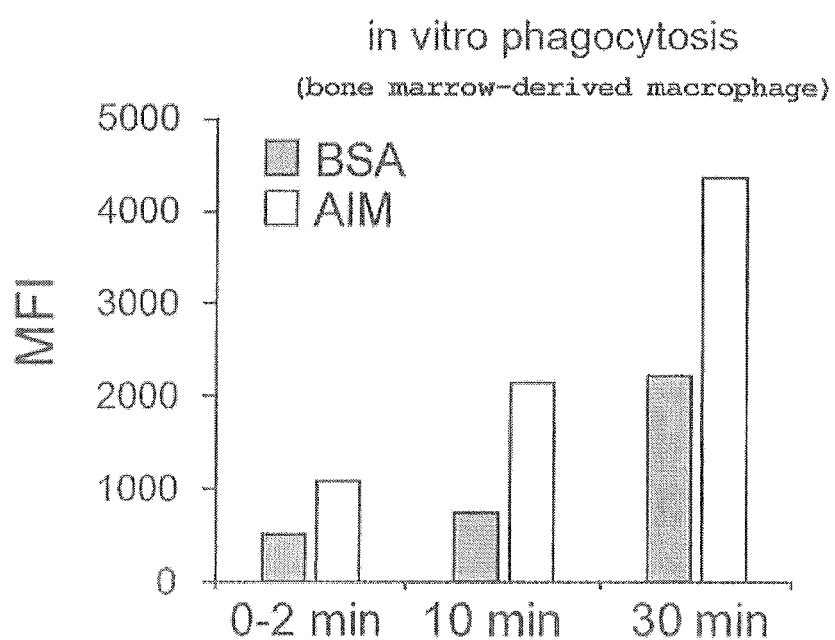
FIG. 19 is a graph showing phagocytic activity of macrophage obtained by differentiating AIM-KO-derived bone marrow cell with M-CSF and isolating by FACS sorter.

Experiment similar to Example 18 was performed using, as phagocyte, macrophage obtained by differentiating AIM-KO-derived bone marrow cells with M-CSF (FIG. 19). Since dead HK2 cells coated with BSA and dead HK2 cells not coated therewith showed no difference in the manner of phagocytosis in Example 18, non-coated dead HK2 cells were not used in this Example. Similar to the results of Example 18, phagocytosis of dead HK2 cells coated with rAIM increased.

Figure 20:
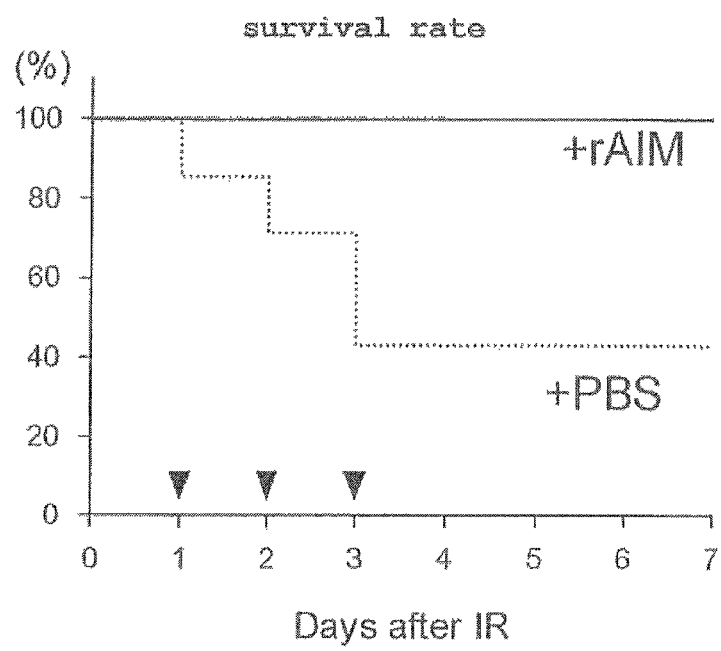
FIG. 20 is a graph showing the survival rate of AIM KO mouse subjected to bilateral transient kidney ischemia/reperfusion and administered with rAIM or PBS from day 1 to day 3.

Example 20: Treatment of Acute Renal Failure of AIM-KO Mouse by AIM Administration AIM-KO mouse was subjected to bilateral IR and rAIM (200 μg/mouse) or an equal amount of PBS was intravenously injected from day 1 to day 3 (n=5-6). The survival rate of mouse injected with PBS was not more than 40% on day 7, but recovered to 100% in mouse administered with rAIM (FIG. 20).

Example 21: Recovery of Clinical Score by AIM Administration

Figure 21:
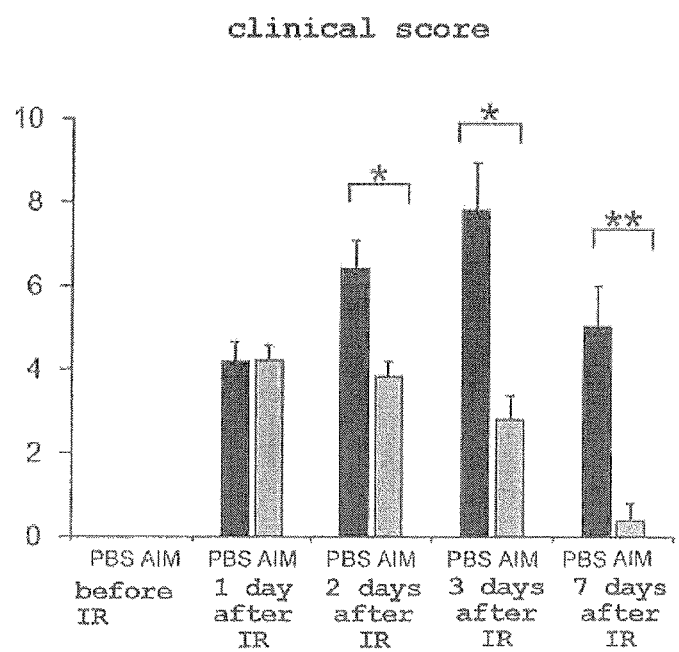
FIG. 21 is a graph showing the clinical score of AIM KO mouse subjected to bilateral transient kidney ischemia/reperfusion and administered with rAIM or PBS from day 1 to day 3. *: P<0.05, **: P<0.01

The clinical score of the mouse of Example 20 was similarly studied as in Example 8 (FIG. 21). A remarkable recovery of clinical score was observed after rAIM administration.

Example 22: Recovery of Kidney Function by AIM Administration

Figure 22:
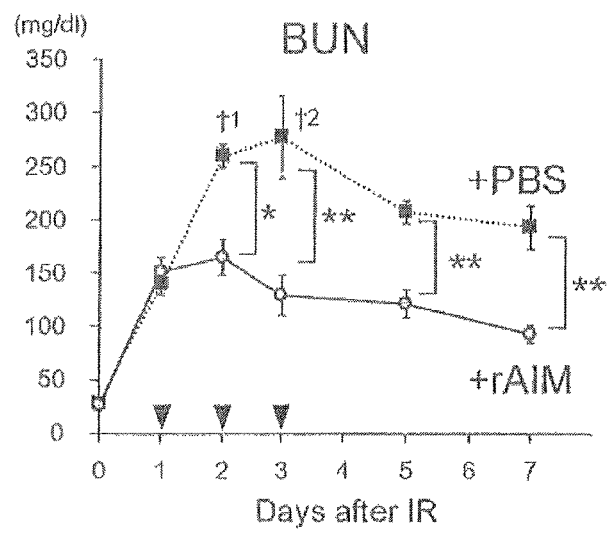
FIG. 22 is a graph showing the BUN value of AIM KO mouse subjected to bilateral transient kidney ischemia/reperfusion and administered with rAIM or PBS from day 1 to day 3. The number of mice that died each day is indicated with +. *: P<0.05, **: P<0.01

BUN of the mouse of Example 20 was similarly measured over time as in Example 9 (FIG. 22). A significant decrease in the BUN value was observed by rAIM administration.

Figure 23:
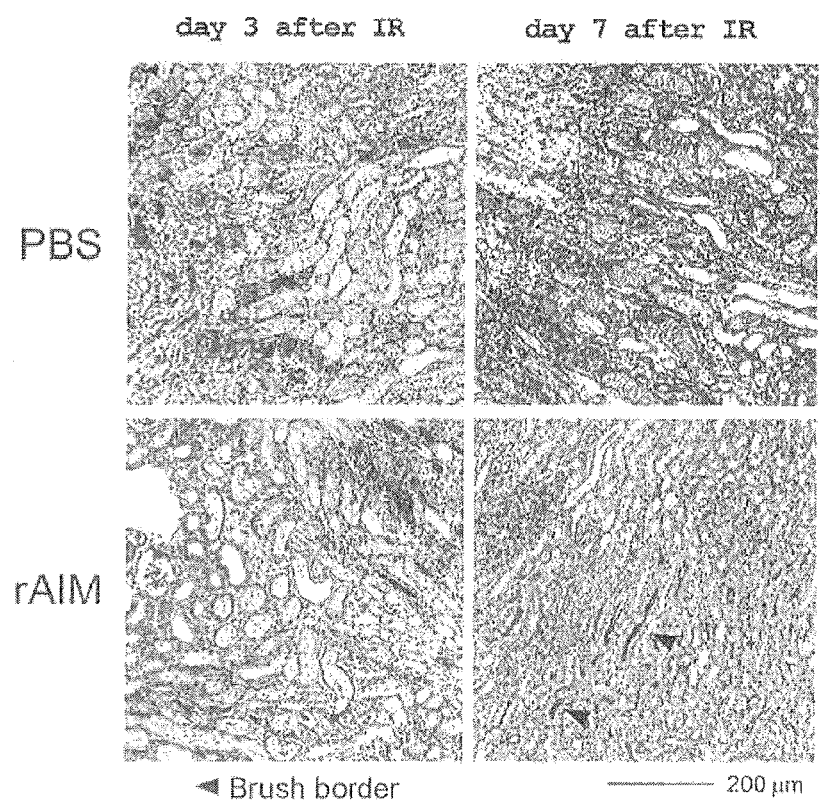
FIG. 23 shows PAS staining images of kidney tissue sections of AIM KO mouse subjected to bilateral transient kidney ischemia/reperfusion and administered with rAIM or PBS from day 1 to day 3.

Example 23: Removal of Necrotic Epithelial Cell Mass in Renal Tubule by AIM Administration AIM-KO mouse was subjected to bilateral IR, and rAIM (200 μg/mouse) or an equal amount of PBS was intravenously injected from day 1 to day 3, and the state of the kidney was analyzed by PAS staining on day 3 and on day 7 (FIG. 23). In PBS administration, dead cells in proximal renal tubule were accumulated, remarkable removal was observed in the mouse administered with rAIM, and renal tubule cells having a brush border were recovered on day 7.

Figure 24:
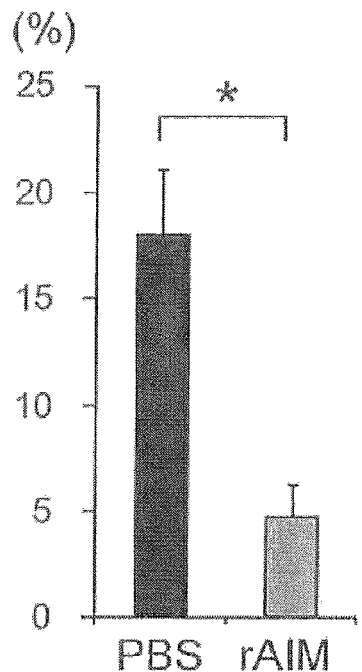
FIG. 24 is a graph showing the ratio of the area of dead cell mass in proximal renal tubule in kidney (on day 7 after IR) tissue sections of AIM KO mouse subjected to bilateral transient kidney ischemia/reperfusion and administered with rAIM or PBS from day 1 to day 3, relative to the total area per one section. *: p<0.05

Example 24: Quantification of Necrotic Epithelial Cell Mass in Renal Tubule after AIM Administration In the kidney on day 7 after IR, The area of dead cell mass in the proximal renal tubule observed in FIG. 23 was quantified by calculating as a ratio relative to the total area of one section (n=3 each) (FIG. 24). A remarkable decrease in the dead cell mass was observed in the rAIM administration group.

Example 25: Decrease of Inflammation Reaction by AIM Administration (Inflammatory Cytokine)

Figure 25:
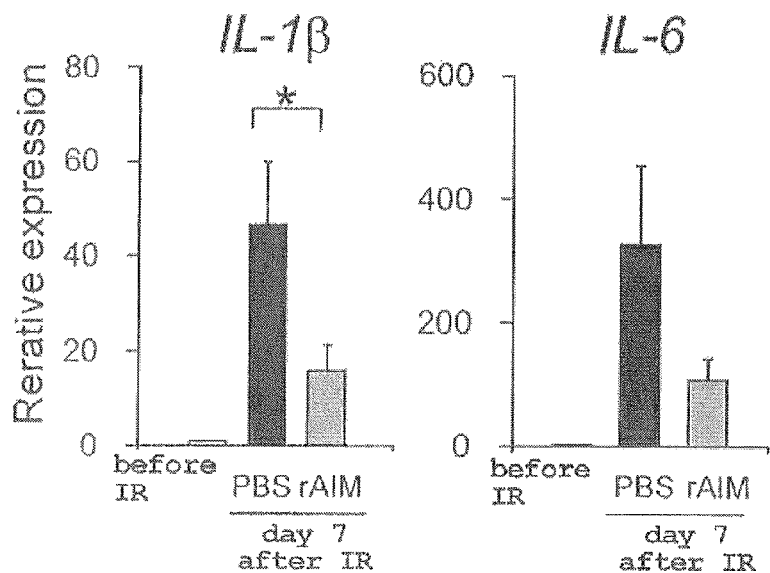
FIG. 25 is a graph showing the mRNA expression ratio of IL-1b and IL-6 in AIM KO mouse subjected to bilateral transient kidney ischemia/reperfusion and administered with rAIM or PBS from day 1 to day 3, by quantitative RT-PCR. *: p<0.05

In the mouse of Example 20, RNA was extracted from the kidney on day 7 after IR, and inflammatory cytokines IL-1β and IL-6 were analyzed by quantitative RT-PCR (FIG. 25). In the rAIM administration group, both IL-1β and IL-6 decreased as compared to the PBS administration group, and inflammation reaction associated with acute renal failure was also suggested to have been suppressed by rAIM administration.

Example 26: Effect of AIM on Acute Renal Failure by Nonfatal (Mild) IR

Figure 26:
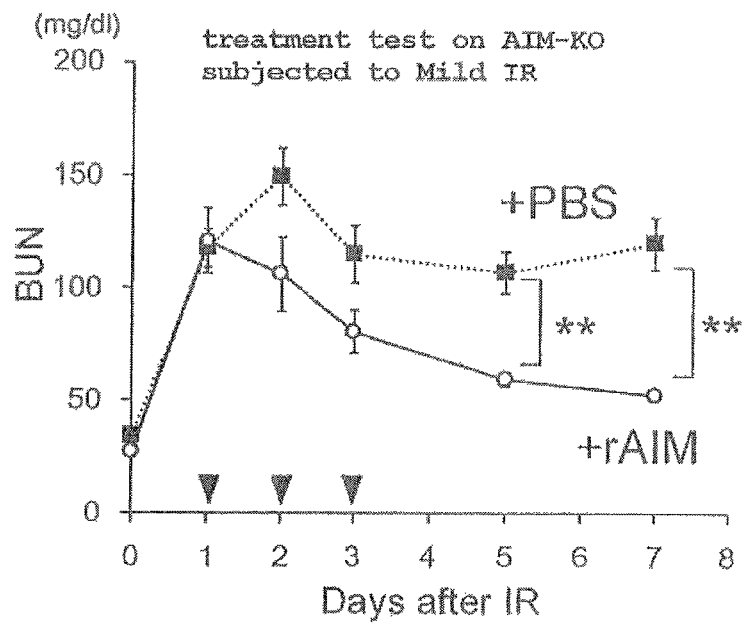
FIG. 26 is a graph showing the BUN value of AIM KO mouse subjected to nonfatal bilateral transient kidney ischemia/reperfusion and administered with rAIM or PBS from day 1 to day 3. *: p<0.05

In bilateral IR carried out in Examples 6-25, ischemia was performed for 30 min, and acute renal failure with high fatality was induced in AIM-KO. In this Example, the time of ischemia was shortened (30 min→25 min), renal failure of the level showing 100% survival rate on day 7 even in AIM-KO was induced in AIM-KO mouse, and rAIM or PBS was administered by injection into the cervical vein from day 1 to day 3 similar to that in Example 20. Even in IR under such mild conditions, improvement of BUN could be accelerated more by rAIM administration (n=5 each) (FIG. 26).

Example 27: Treatment Effect of AIM on WT Mouse

Figure 27:
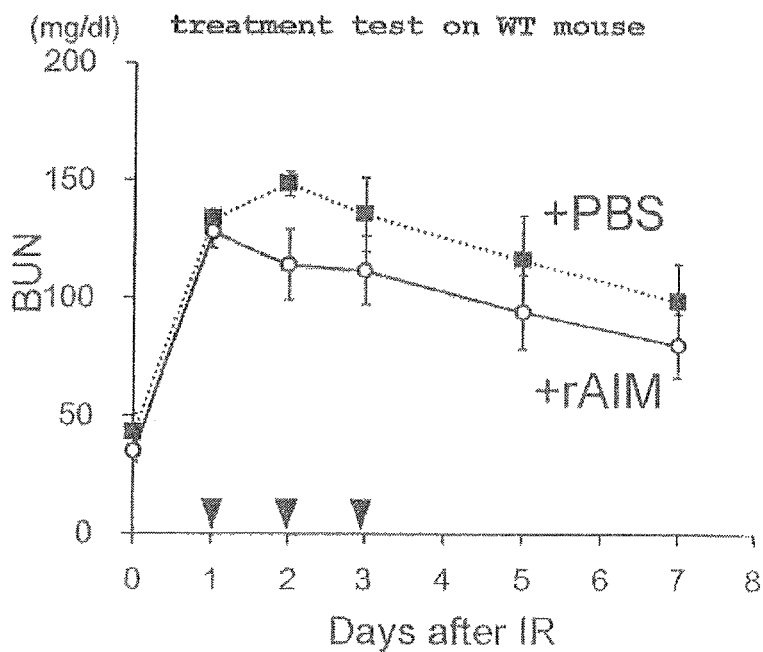
FIG. 27 is a graph showing the BUN value of WT mouse subjected to bilateral transient kidney ischemia/reperfusion and administered with rAIM or PBS from day 1 to day 3.

WT mouse originally having endogenous AIM was subjected to bilateral IR (ischemia 30 min), and rAIM or PBS was administered (n=5-6) similar to that in Example 20. In WT, renopathy is recovered by the original endogenous AIM, and rAIM could further accelerate the improvement thereof (FIG. 27). It was found that BUN value that increased up to day 2 by rAIM administration already decreased.

Example 28: Renal Failure that Became Chronic by Lack of AIM

Figure 28:
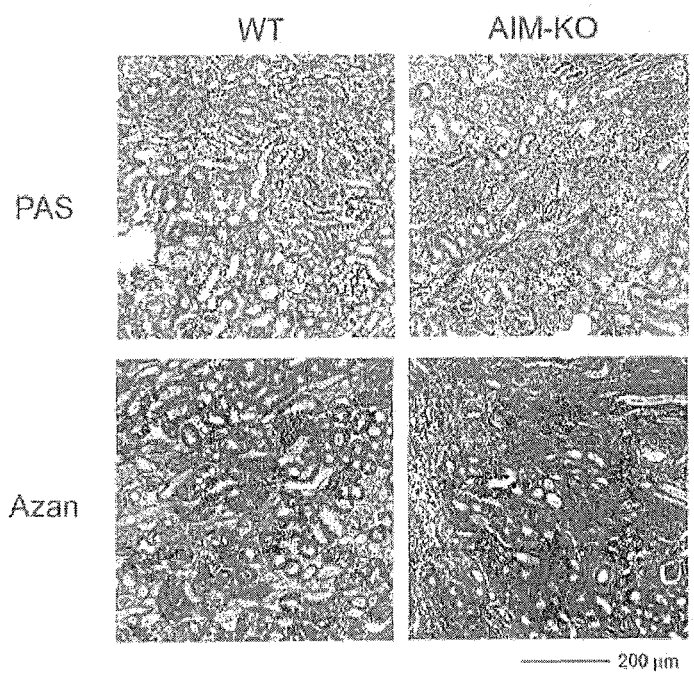
FIG. 28 shows PAS staining images and Azan staining images of kidney tissue sections of AIM KO mouse and WT mouse that underwent nonfatal bilateral transient kidney ischemia/reperfusion.

WT and AIM-KO mice were subjected to mild IR similar to that in Example 26, and the state of the kidney on day 28 after IR was analyzed by PAS staining (to observe dead cell mass) and Azan staining (to observe fibrosis) (FIG. 28). Even on day 28, PAS positive dead cell mass remained somewhat in AIM-KO as compared to WT. In AIM-KO, marked fibrosis (Azan positive) was observed, and the structure of renal tubule was deformed as compared to WT.

Example 29: Promotion of Renal Fibrosis by Lack of AIM

Figure 29:
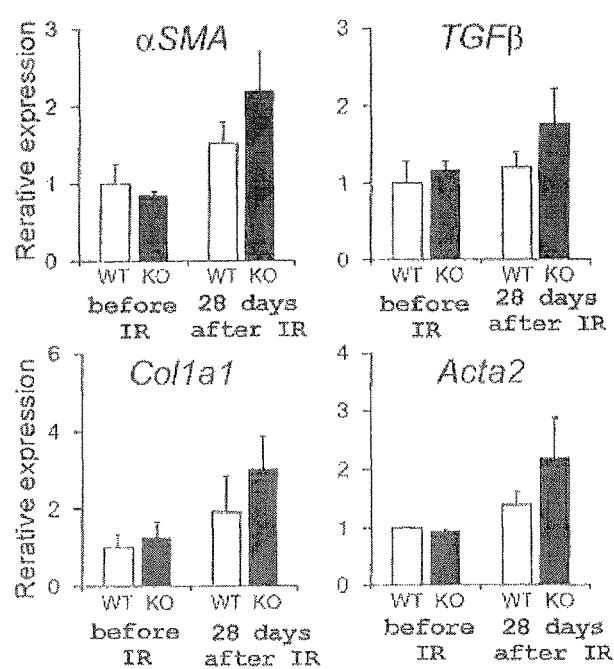
FIG. 29 is a graph showing the mRNA expression ratio of 4 kinds of fibrosis markers in AIM KO mouse and WT mouse that underwent nonfatal bilateral transient kidney ischemia/reperfusion, by quantitative RT-PCR.

RNA was extracted from the kidney of the mouse of Example 28 on day 28 after IR, and 4 kinds of fibrosis markers were analyzed by quantitative RT-PCR (n=4 each) (FIG. 29). In AIM-KO, all fibrosis markers increased as compared to WT.

Figure 30:
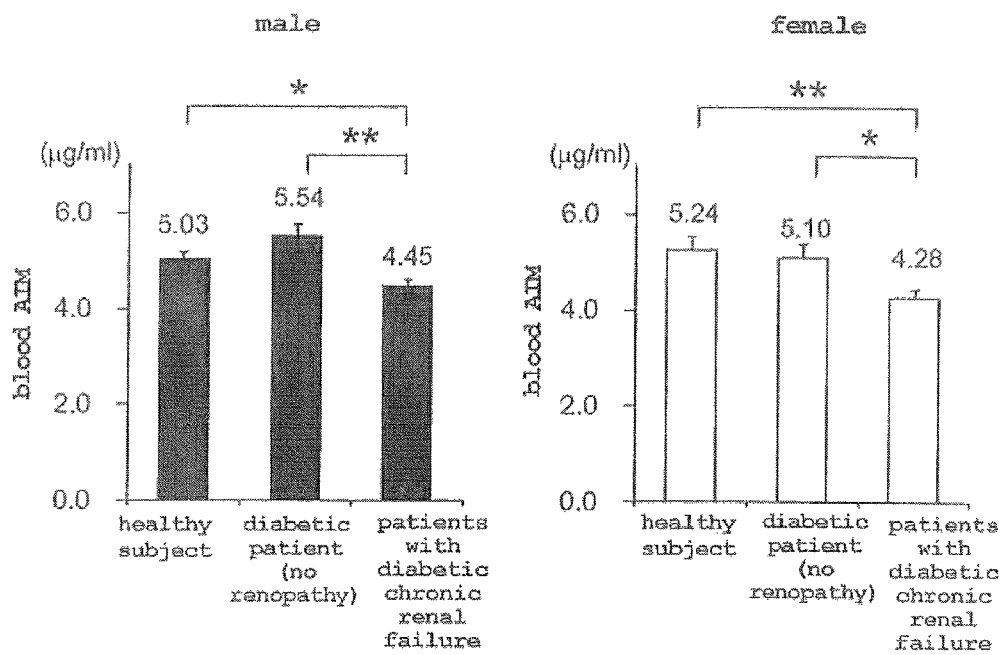
FIG. 30 is a graph showing the gender-segregated blood AIM concentration of healthy human, diabetes patients without renopathy, and patients with diabetic chronic renal failure. *: p<0.05, **: p<0.01

Example 30: Blood AIM Value in Human Patients with Diabetic Chronic Renal Failure Gender-segregated blood AIM concentration was measured in (1) healthy humans (male: 142, female: 54), (2) diabetes patients without renopathy (Cre<1.0 mg/dl) (male: 70, female: 57), and (3) patients with diabetic chronic renal failure (male: 146, female: 54), who were at almost the same age (FIG. 30). Both male and female showed no significant difference in the AIM value in (1) and (2), but the value was significantly low in (3).

Figure 31:
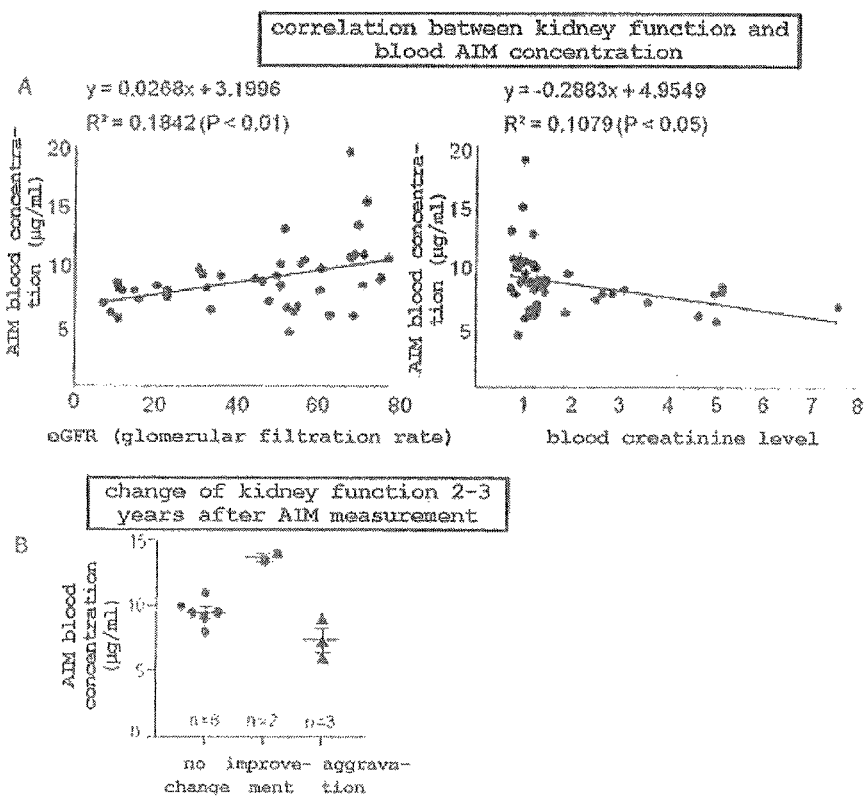
FIG. 31 shows A: a graph showing the correlation between eGFR (glomerular filtration rate; ml/min/1.73 m$^2$) or blood creatinine level (mg/dl), and blood AIM concentration in chronic renal failure patients (n=55), B: a graph showing the correlation between blood AIM concentration and changes in the kidney function at 2-3 years from the measurement of concentration thereof in the chronic renal failure patients.
Figure 36:
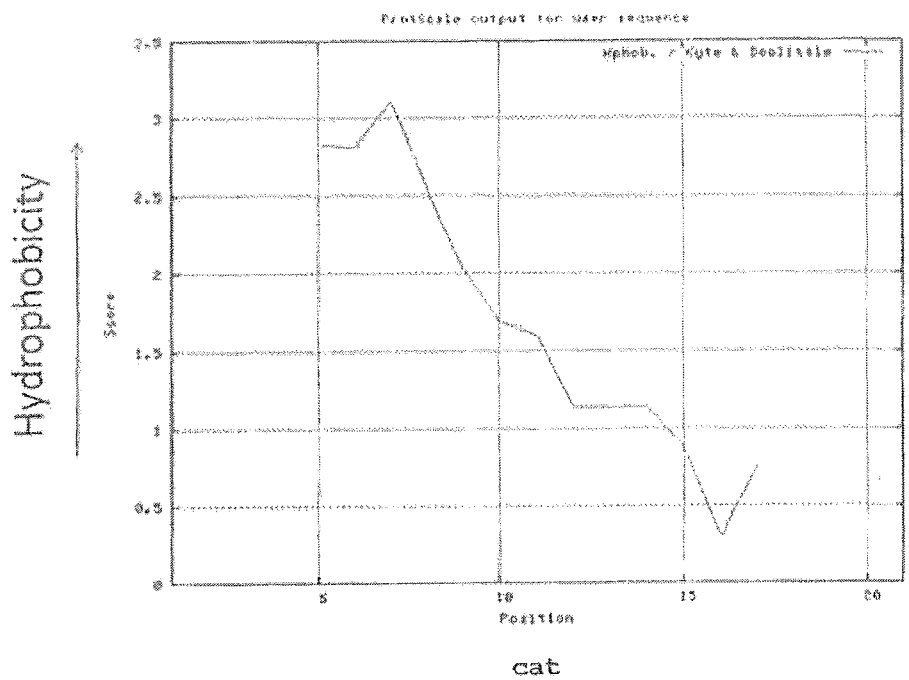
FIG. 36 shows hydrophobicity of leader peptide sequence of a cat AIM protein.
Figure 37:
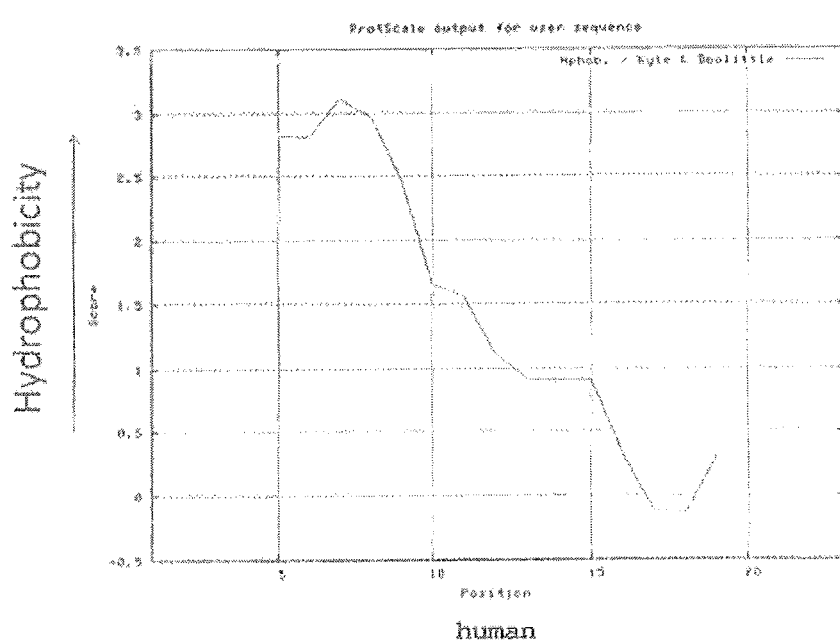
FIG. 37 shows hydrophobicity of leader peptide sequence of a human AIM protein.
Figure 38:
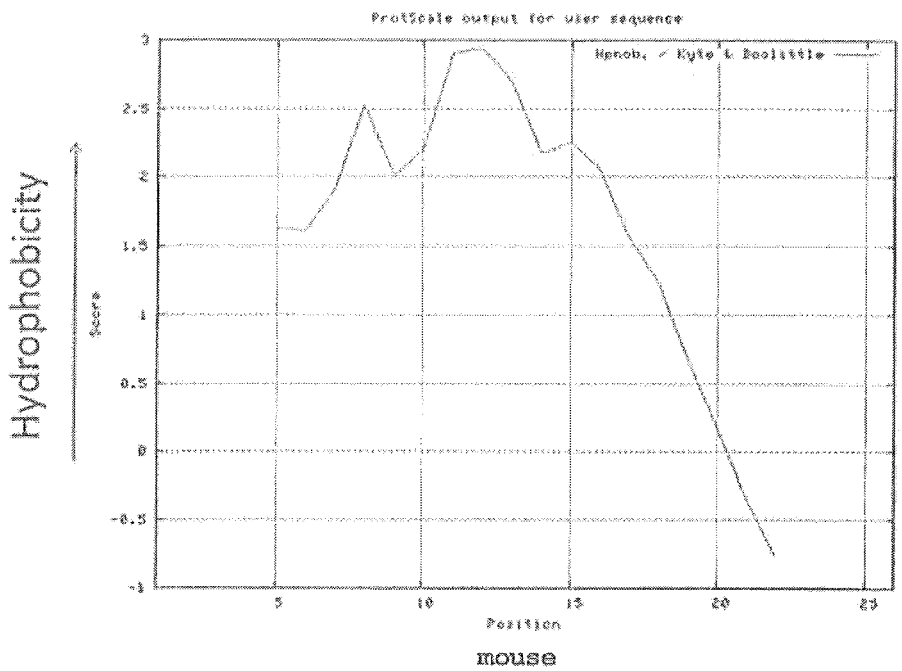
FIG. 38 shows hydrophobicity of leader peptide sequence of a mouse AIM protein.
Figure 39:
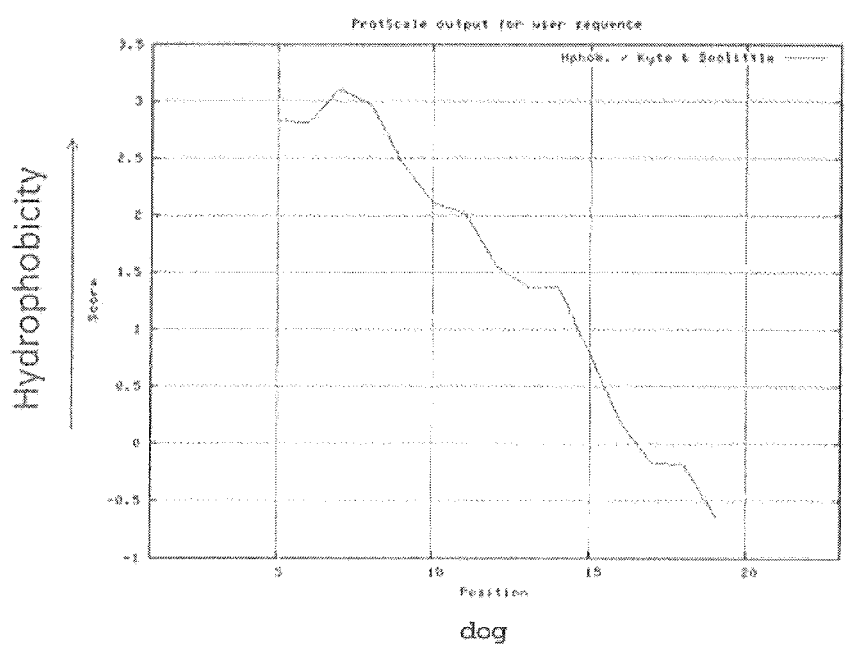
FIG. 39 shows hydrophobicity of leader peptide sequence of a dog AIM protein.

Example 31: Correlation Between Kidney Function and Blood AIM Human in Patients with Chronic Kidney The blood AIM value of patients with chronic kidney disease (CKD) was analyzed, and the correlation between individual kidney function marker eGFR (glomerular filtration rate) and blood creatinine value was examined (n=55). As the causative disease of CKD, diabetic nephropathy, glomerulonephritis, hypertensive nephropathy, IgA nephropathy and the like can be mentioned. The age of patients (male and female) was not more than 60. As shown in FIG. 31A, a significant correlation was found between blood AIM value and kidney function. Furthermore, patients with comparatively high AIM value at the time point of this analysis showed improved kidney function by a trace research 2-3 years later, and patients with low AIM value conversely showed degraded kidney function (FIG. 31B). That is, AIM can be a useful marker for predicting not only the kidney function at present but also prognosis in CKD patients.

Example 32: Lack (or Remarkable Decrease) of Blood AIM in Cat

Each serum from dogs (3), cats (3) and mouse was subjected to immunoblot under reduction conditions by using an anti-AIM antibody (Rab2: polyclonal antibody produced by immunizing rabbit with mouser AIM, which has been clarified to detect mouse and human AIMs) (FIG. 32A). As a result, while a signal could be confirmed in dog serum, a signal could hardly be detected in 3 cats. This is not the problem of antibody, and cat rAIM protein obtained by cloning cat AIM cDNA (see Example 36), incorporating same with HA tag attached to the C-terminal into a pCAGGS expression vector, expressing same in HEK293T cells and purifying same from the culture supernatant by using an anti-HA antibody column could be detected at the same level as mouse rAIM, by immunoblot under reduction conditions using this antibody (FIG. 32B). From these results, it was found that the cats studied in this Example expressed functional AIM mRNA, but scarcely contained AIM protein in blood.

Example 33: Bindability of Cat AIM and IgM in Cat Blood

A plasmid wherein the cat AIM cDNA shown in FIG. 35 is inserted into an expression vector was transfected to HEK293T cells, recombinant cat AIM (1 mg) purified from the culture supernatant thereof was intravenously injected to a cat (hybrid, male 2 years 3 months old), a blood sample was collected 1 hr later and serum was separated. The serum was applied to size fractionation using gel, and each fraction was analyzed for AIM and IgM by the Westernblot method. As shown in FIG. 33A, the fraction containing AIM and the fraction containing IgM are clearly different. The results are different from the results of similar fractionation analysis of the serum obtained by intravenously injecting mouse AIM to AIM KO mouse (FIG. 33B, Comparative Example) (IgM and AIM fractions completely match). That is, AIM originally binds to IgM in blood and maintains the stability thereof (prior art reference: Arai et al., Cell Reports 3: 1187-1198, 2013), as a result of which the blood concentration of AIM is maintained. In cat, however, since AIM cannot bind to IgM, stability of AIM in blood cannot be maintained and, as a result, blood concentration of AIM cannot be maintained.

Example 34: Bindability of Mouse AIM and IgM in Cat Blood

Using mouse AIM, a test similar to Example 33 was carried out. Recombinant mouse AIM (1 mg) was intravenously injected to a cat (hybrid, male 2 years 3 months old), a blood sample was collected 1 hr later, and the serum was separated. The serum was applied to size fractionation using gel, and each fraction was analyzed for AIM and IgM by the Westernblot method. As shown in FIG. 34A, the fraction containing mouse AIM completely matched with the fraction containing cat IgM. Therefore, different from cat AIM, mouse AIM is considered to bind to IgM and be stabilized in blood.

Example 35: Binding Site of Mouse AIM to IgM

A plurality of C-terminal deficient recombinant modified mouse AIMs were produced. The binding of the modified mouse AIM and IgM was confirmed in vitro. As a result, modified mouse AIM having a partly deficient SRCR3 domain showed a markedly decreased binding with IgM. Therefore, it was found that the SRCR3 domain of mouse AIM is important for binding with IgM.

Example 36: Cat AIM cDNA Sequence

A plurality of primers were designed from a predicted sequence (GenBank Accession No.:XM_003999688.1) of cat CD5L (=AIM) disclosed in NCBI Resources, and full-length cat AIM cDNA (SEQ ID NO: 5) was isolated from cDNA pool of cat spleen (FIG. 35). In the sequence, particularly a sequence encoding a leader peptide was vastly different from the disclosed sequence.

Example 37: Hydrophobicity of Leader Peptide

The hydrophobicity of the leader peptide sequence of AIM protein of each of cat, human, mouse, dog is shown (FIGS. 36-39). All showed sufficient hydrophobicity and satisfied the prerequisite for a secreted protein. The leader peptide of cat was analyzed from the cDNA isolated by us, and dog AIM was analyzed from the predicted sequence disclosed in NCBI Resources (GenBank Accession No.: XM_846487.2).

Example 38: Comparison of AIM Amino Acid Sequences of Human, Cat, Mouse

Amino acid sequences were compared among the three as to the leader peptide (LS), each SRCR, and hinge region (FIG. 40). In the Figure, the amino acid common to the three is shown with "*", one common to human and cat alone is shown with ".", and one common to human and mouse alone is shown with ":".

Example 39: Analysis of Blood AIM in Cat

In Example 32, anti-mouse AIM antibody was used to detect cat AIM. In this Example, a DNA wherein HA tag is linked to cDNA of cat AIM was incorporated into an expression vector, and transfected to HEK293T cells, whereby recombinant cat AIM protein wherein C-terminal is loaded with HA peptide (rcAIM-HA) was produced, which was used to immunize mouse to establish an anti-cat AIM monoclonal antibody. Using the antibody, the blood AIM concentration of cats (48 individuals) of various strains was analyzed by the reduced Western blotting method (FIG. 41). As a control concentration, rcAIM-HA was used. As a result, irrespective of the strain, individuals with detected AIM and individuals with undetected AIM were found. Of the individuals with detected AIM, mean blood AIM concentration of 4 representative individuals was 16.8 µg/ml, which was markedly higher than about 5 µg/ml of mouse and human.

Example 40: Establishment of IR Method for Cat

Figure 42:
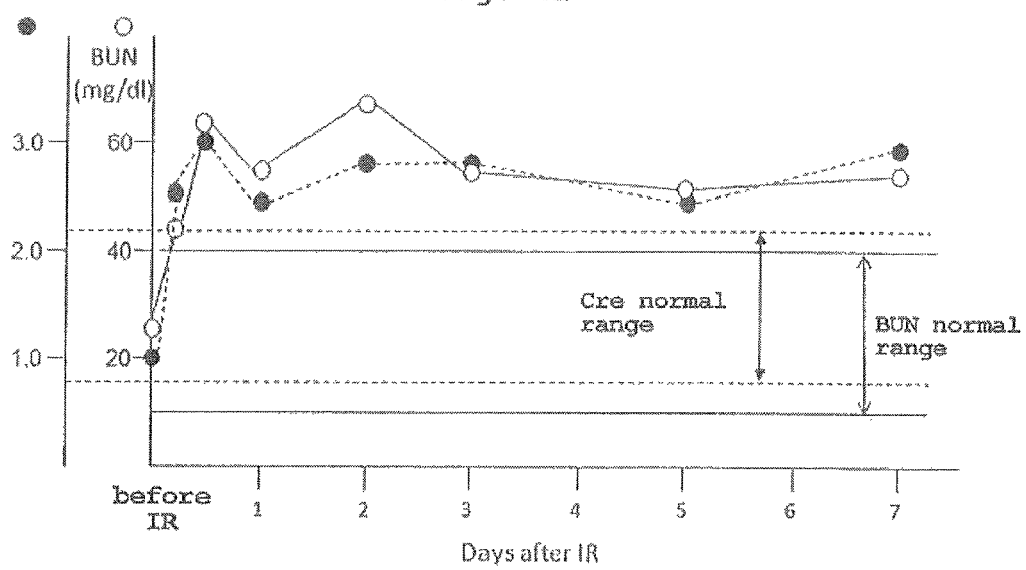
FIG. 42 is a graph showing BUN value and Cre value of a cat that underwent bilateral transient kidney ischemia/reperfusion. ●: Cre, ○: BUN

An acute renal failure induction method by IR was established in cat with high blood AIM concentration. Under systemic anesthesia, bilateral renal artery was obstructed with a clamp for 1 hr under a laparoscope and then released. Thereafter, blood and urine were collected over time, and the kidney function was studied. FIG. 42 shows the profile of blood BUN value and Cre value. In 12 hr after IR, both the BUN value and Cre value reached a peak, and was not improved until day 7. Like AIM-KO mouse, recovery from acute renal failure was suggested to be highly possibly disordered.

Example 41: Analysis of Blood and Urine AIMs of Cat after IR

Figure 43:
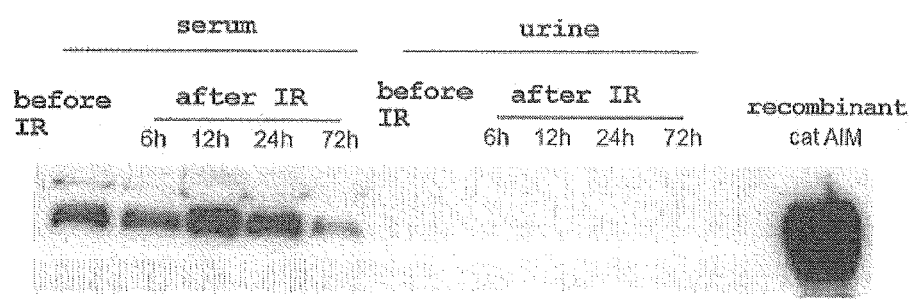
FIG. 43 shows reduced Western blotting images of serum or urine AIM of cat before and after IR, by using an anti-cat AIM monoclonal antibody.

In mouse, AIM was detected in urine after IR, and is considered to accumulate on the dead cell mass clogged in renal tubule. The serum and urine of cat after IR were analyzed by the reduced Western blotting method using an anti-cat AIM antibody, and AIM was not detected in urine of cat after IR (FIG. 43). The amount of AIM in blood did not show a clear change.

Figure 44:
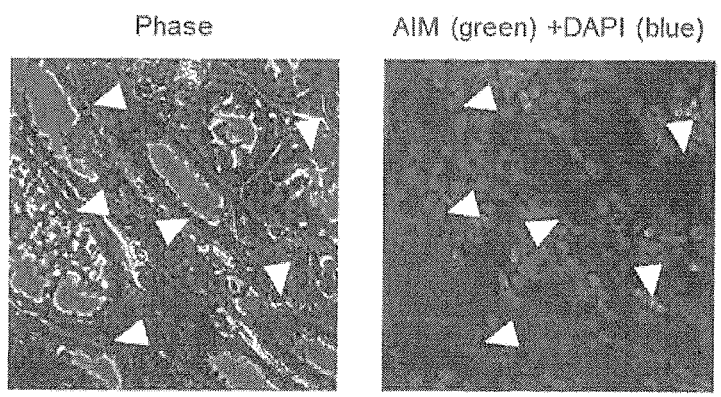
FIG. 44 shows immunostaining images of kidney tissue section of cat that underwent bilateral transient kidney ischemia/reperfusion, by using an anti-AIM antibody.

Example 42: Presence or Absence of AIM Accumulation in Dead Cell Mass in Proximal Renal Tubule of Cat Induced with Acute Renal Failure Cat was subjected to bilateral IR and whether AIM is accumulated on necrotic cell mass in renal tubule in the kidney on day 3 was analyzed by immunostaining (FIG. 44). Necrotic cell mass was detected in the proximal renal tubule (white arrow part); however, accumulation of AIM was not observed in the same part. In Example 41, AIM was not detected in the urine after IR and, as a result, it was suggested that AIM did not reach the dead cell mass in the renal tubule.

Figure 45:
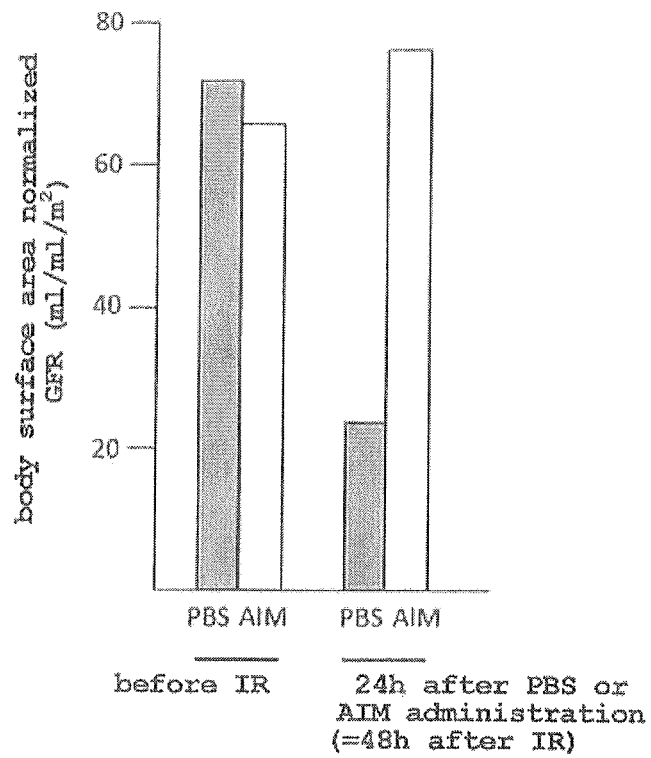
FIG. 45 is a graph showing eGFR (glomerular filtration rate; ml/min/m$^2$) of cat that underwent bilateral transient kidney ischemia/reperfusion and administered with rAIM or PBS. n=1 each

Example 43: Effect of AIM Administration on Cat Induced with Acute Renal Failure Similar to the method described in Example 40, cat (female 5 years old) was subjected to bilateral IR, an artery catheter was inserted from the inguinal region artery after 24 hr under anesthesia, the catheter tip was advanced to the renal artery, and a solution of rAIM (50 mg) dissolved in PBS (50 ml) was injected into the unilateral renal arteries by 25 ml (rAIM: 25 mg) each. Another cat (also female 5 years old) was similarly subjected to IR and catheter insertion, and PBS alone was injected into the unilateral renal arteries by 25 ml each. GFR (Glomerular Filtration Rate) normalized with the body surface area before IR and 24 hr after rAIM or PBS injection (48 hr after IR) is shown (FIG. 45). In the cat injected with PBS alone, GFR decreased and the kidney function decreased; however, the cat injected with rAIM did not show a decrease in GFR and the kidney function did not decrease.

Figure 46:
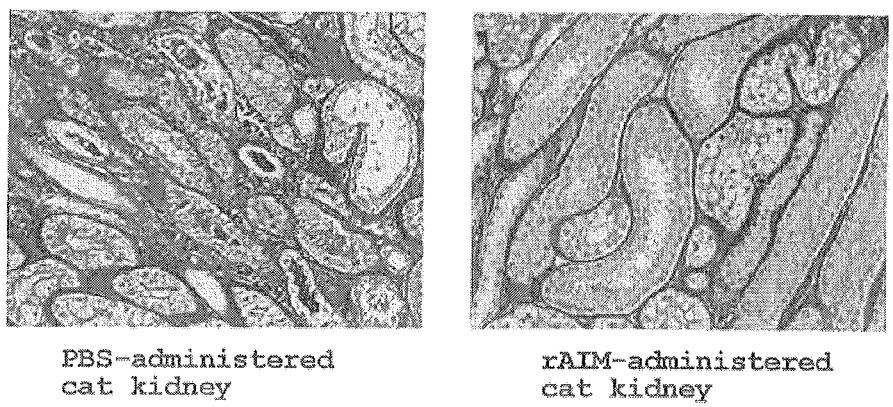
FIG. 46 shows PAS staining images of kidney tissue sections of cat that underwent bilateral transient kidney ischemia/reperfusion and administered with rAIM or PBS.

Example 44: Effect of AIM Administration on Cat Induced with Acute Renal Failure Similar to the method described in Example 43, cat was subjected to bilateral IR, and kidney tissue was analyzed by PAS staining 24 hr after rAIM or PBS injection (48 hr after IR) (FIG. 46). In the cat injected with PBS, necrosis and fall off of renal tubular epithelial cells, destruction of renal tubular structure and growth of stroma were observed. In the cat injected with rAIM, renal tubular epithelial cells were already recovered, brush border was also recovered, and the structure was also restored. In addition, the stroma was thinner than in the cat injected with PBS, and the growth was not observed. Histologically, cure of renal failure by rAIM was clear.

Example 45: Effect of AIM Administration on Cat

AIM or vehicle is consecutively administered every day to 6- to 8-year old cat. Kidney function (BUN value) is measured 2-4 weeks after administration. In the AIM administration group, degradation of kidney function observed in the vehicle administration group is suppressed. Therefore, it is clear that AIM is useful for the degradation of kidney function and the prophylaxis of renal failure in cat. Similar results are obtained by using a drug capable of agonistically controlling the function of AIM (containing partial peptide of AIM having AIM activity) or a drug that induces expression of AIM instead of AIM.

Example 46: Effect of Administration of Modified AIM on Cat

SRCR3 domain of cat AIM is altered to the SRCR3 domain of mouse AIM to produce modified cat AIM that binds to IgM. Modified AIM or vehicle is consecutively administered every day to 6- to 8-year old cat. Kidney function (BUN value) is measured 2-4 weeks after administration. In the modified AIM administration group, degradation of kidney function observed in the vehicle administration group is suppressed. Therefore, it is clear that AIM is useful for the degradation of kidney function and the prophylaxis of renal failure in cat. In addition, since modified cat AIM binds to IgM in blood, and is stabilized, effectiveness is obtained by the administration of a low dose of modified cat AIM than the administration of cat AIM. Modified cat AIM only needs to be bound to cat IgM and is not limited.

INDUSTRIAL APPLICABILITY

The present invention can provide a prophylactic or therapeutic agent for a kidney disease, comprising AIM as an active ingredient. In addition, the kidney disease model mouse of the present invention contributes to the elucidation of the onset mechanism of kidney diseases and, according to the screening method using the kidney disease model mouse, a substance effective to the prophylaxis or treatment for kidney diseases can be searched. In addition, using the kidney disease model mouse of the present invention, effects of a known prophylactic or therapeutic agent for a kidney disease can be evaluated. Furthermore, the present invention can provide a method for diagnosis of a kidney disease.

This application is based on patent application No. 2014-022041 filed in Japan (filing date: Feb. 7, 2014), the contents of which are incorporated in full herein.

The invention claimed is:

1. A method for the treatment of a kidney disease, comprising administering an effective amount of Apoptosis Inhibitor of Macrophage (AIM) polypeptide consisting of the amino acid sequence represented by SEQ ID NO: 2, to a subject suffering from a kidney disease, wherein the kidney disease is acute renal failure.

2. The method according to claim 1, wherein the subject of treatment is a human.

3. The method according to claim 1, wherein the subject of treatment is a cat.

4. The method according to claim 3, wherein the AIM binds to cat IgM.

5. A method for the treatment of a kidney disease, comprising administering an effective amount of Apoptosis Inhibitor of Macrophage (AIM) polypeptide consisting of the amino acid sequence represented by SEQ ID NO: 4, to a subject suffering from a kidney disease, wherein the kidney disease is acute renal failure.

6. The method according to claim 5, wherein the subject of treatment is a human.

7. The method according to claim 5, wherein the subject of treatment is a cat.

8. The method according to claim 7, wherein the AIM binds to cat IgM.

* * * * *

SEQUENCE LISTING

```
<160> NUMBER OF SEQ ID NOS: 6

<210> SEQ ID NO 1
<211> LENGTH: 1044
<212> TYPE: DNA
<213> ORGANISM: Homo sapiens

<400> SEQUENCE: 1
atggctctgc tattctcctt gatccttgcc atttgcacca gacctggatt cctagcgtct      60
ccatctggag tgcggctggt gggggcctc caccgctgtg aagggcgggt ggaggtggaa      120
cagaaaggcc agtggggcac cgtgtgtgat gacggctggg acattaagga cgtggctgtg      180
ttgtgccggg agctgggctg tggagctgcc agcggaaccc ctagtggtat tttgtatgag      240
ccaccagcag aaaaagagca aaaggtcctc atccaatcag tcagttgcac aggaacagaa      300
gatacattgg ctcagtgtga gcaagaagaa gtttatgatt gttcacatga tgaagatgct      360
ggggcatcgt gtgagaaccc agagagctct ttctccccag tcccagaggg tgtcaggctg      420
gctgacggcc ctgggcattg caagggacgc gtggaagtga agcaccagaa ccagtggtat      480
accgtgtgcc agacaggctg gagcctccgg gccgcaaagg tggtgtgccg gcagctggga      540
tgtgggaggg ctgtactgac tcaaaaacgc tgcaacaagc atgcctatgg ccgaaaaccc      600
atctggctga gccagatgtc atgctcagga cgagaagcaa cccttcagga ttgcccttct      660
gggccttggg ggaagaacac ctgcaaccat gatgaagaca cgtgggtcga atgtgaagat      720
ccctttgact tgagactagt aggaggagac aacctctgct ctgggcgact ggaggtgctg      780
cacaagggcg tatgggctc tgtctgtgat gacaactggg gagaaaagga ggaccaggtg      840
gtatgcaagc aactgggctg tgggaagtcc ctctctccct ccttcagaga ccggaaatgc      900
tatggccctg gggttggccg catctggctg gataatgttc gttgctcagg ggaggagcag      960
tccctggagc agtgccagca cagattttgg gggtttcacg actgcaccca ccaggaagat     1020
gtggctgtca tctgctcagg atag                                              1044

<210> SEQ ID NO 2
<211> LENGTH: 347
<212> TYPE: PRT
<213> ORGANISM: Homo sapiens

<400> SEQUENCE: 2
```

Met Ala Leu Leu Phe Ser Leu Ile Leu Ala Ile Cys Thr Arg Pro Gly
1               5                   10                  15

Phe Leu Ala Ser Pro Ser Gly Val Arg Leu Val Gly Gly Leu His Arg
            20                  25                  30

Cys Glu Gly Arg Val Glu Val Glu Gln Lys Gly Gln Trp Gly Thr Val
        35                  40                  45

Cys Asp Asp Gly Trp Asp Ile Lys Asp Val Ala Val Leu Cys Arg Glu
    50                  55                  60

Leu Gly Cys Gly Ala Ala Ser Gly Thr Pro Ser Gly Ile Leu Tyr Glu
65              70                  75                  80

Pro Pro Ala Glu Lys Glu Gln Lys Val Leu Ile Gln Ser Val Ser Cys
                85                  90                  95

Thr Gly Thr Glu Asp Thr Leu Ala Gln Cys Glu Gln Glu Val Tyr
            100                 105                 110

Asp Cys Ser His Asp Glu Asp Ala Gly Ala Ser Cys Glu Asn Pro Glu
            115                 120                 125

Ser Ser Phe Ser Pro Val Pro Glu Gly Val Arg Leu Ala Asp Gly Pro
    130                 135                 140

Gly His Cys Lys Gly Arg Val Glu Val Lys His Gln Asn Gln Trp Tyr
145                 150                 155                 160

Thr Val Cys Gln Thr Gly Trp Ser Leu Arg Ala Ala Lys Val Val Cys
            165                 170                 175

Arg Gln Leu Gly Cys Gly Arg Ala Val Leu Thr Gln Lys Arg Cys Asn
            180                 185                 190

Lys His Ala Tyr Gly Arg Lys Pro Ile Trp Leu Ser Gln Met Ser Cys
            195                 200                 205

Ser Gly Arg Glu Ala Thr Leu Gln Asp Cys Pro Ser Gly Pro Trp Gly
    210                 215                 220

Lys Asn Thr Cys Asn His Asp Glu Asp Thr Trp Val Glu Cys Glu Asp
225                 230                 235                 240

Pro Phe Asp Leu Arg Leu Val Gly Gly Asp Asn Leu Cys Ser Gly Arg
            245                 250                 255

Leu Glu Val Leu His Lys Gly Val Trp Gly Ser Val Cys Asp Asp Asn
            260                 265                 270

Trp Gly Glu Lys Glu Asp Gln Val Val Cys Lys Gln Leu Gly Cys Gly
            275                 280                 285

Lys Ser Leu Ser Pro Ser Phe Arg Asp Arg Lys Cys Tyr Gly Pro Gly
    290                 295                 300

Val Gly Arg Ile Trp Leu Asp Asn Val Arg Cys Ser Gly Glu Glu Gln
305                 310                 315                 320

Ser Leu Glu Gln Cys Gln His Arg Phe Trp Gly Phe His Asp Cys Thr
            325                 330                 335

His Gln Glu Asp Val Ala Val Ile Cys Ser Gly
            340                 345

<210> SEQ ID NO 3
<211> LENGTH: 1068
<212> TYPE: DNA
<213> ORGANISM: Felis catus

<400> SEQUENCE: 3
atggcgctac tcttctccct aatcctcgcc atttacactg gacctggcat tttagggtct     60
ttttccagag tgcggctagt gggaggcgac caccgctgtg aaggtcgtgt ggagttgcag    120

```
caggatgacg agtgggtcac cgtgtgtgat gactactgga acatggactc tgtggccgtg    180
ctgtgccggg agctgggctg tggggcggcc aggaagacca tgagtggcac cgtgtatgga    240
ccagtgacac caaaggacca aaaagtcttc atccacctgt tcagatgcaa tgggatcgaa    300
gaaagcctgt ctcagtgcga gagggaagat gcaatcggat gctcccatgt tgaggatgcg    360
ggagccgtgt gcgagcccat ttacactgga cctggcattt tagggccgga gagtgtgagg    420
ctggccgatg gccccggggcg ctgccagggc cgagtggagg tgaagttccg aggggagtgg    480
agctctgtgt gccaagcagg ctggagcttt gcagccgcca aggtggtgtg ccggcagctg    540
gggtgtggac gggccaccct gacccggaga ggctgcaaca agcgaccca gggccaaggg    600 gccatctggc agagaaaggc gtcatgctca ggacaagaag tgagccttca agattgcctt    660
tctgaagttt gggaacacaa ctgtacccac aatgaggacg tgtgggtcga atgtgaagat    720 cccttttgcct tgaagctggt aggaggacgc agccactgtg aggggaggct ggaggtgctg    780
cacaagggcg agtggggctc tgtctgcgac gacggctggg acaagacgc agaccgggtg    840 gtgtgcaggc agctgggctg cgggcagccc ctgtctccgc ctgtcaaagt ccggagaagg    900
ttcggccccg gggtcggccg catctggctg gacgacgtca agtgctcggg aaggagccg    960 tccctggagc agtgcctgca caggtcctgg ggctaccaca actgtaacca cagagaggat   1020
gtggctgtgg tctgtgaaga acagcagtct ggcctacctg atgcttga                1068

<210> SEQ ID NO 4
<211> LENGTH: 355
<212> TYPE: PRT
<213> ORGANISM: Felis catus

<400> SEQUENCE: 4

Met Ala Leu Leu Phe Ser Leu Ile Leu Ala Ile Tyr Thr Gly Pro Gly
1               5                   10                  15

Ile Leu Gly Ser Phe Ser Arg Val Arg Leu Val Gly Gly Asp His Arg
            20                  25                  30

Cys Glu Gly Arg Val Glu Leu Gln Gln Asp Asp Glu Trp Val Thr Val
        35                  40                  45

Cys Asp Asp Tyr Trp Asn Met Asp Ser Val Ala Val Leu Cys Arg Glu
    50                  55                  60

Leu Gly Cys Gly Ala Ala Arg Lys Thr Met Ser Gly Thr Val Tyr Gly
65                  70                  75                  80

Pro Val Thr Pro Lys Asp Gln Lys Val Phe Ile His Leu Phe Arg Cys
                85                  90                  95

Asn Gly Ile Glu Glu Ser Leu Ser Gln Cys Glu Arg Glu Asp Ala Ile
            100                 105                 110

Gly Cys Ser His Val Glu Asp Ala Gly Ala Val Cys Glu Pro Ile Tyr
        115                 120                 125

Thr Gly Pro Gly Ile Leu Gly Pro Glu Ser Val Arg Leu Ala Asp Gly
    130                 135                 140

Pro Gly Arg Cys Gln Gly Arg Val Glu Val Lys Phe Arg Gly Glu Trp
145                 150                 155                 160

Ser Ser Val Cys Gln Ala Gly Trp Ser Phe Ala Ala Ala Lys Val Val
                165                 170                 175

Cys Arg Gln Leu Gly Cys Gly Arg Ala Thr Leu Thr Arg Arg Gly Cys
            180                 185                 190

Asn Lys Ala Thr Gln Gly Gln Gly Ala Ile Trp Gln Arg Lys Ala Ser
        195                 200                 205
```

```
Cys Ser Gly Gln Glu Val Ser Leu Gln Asp Cys Leu Ser Glu Val Trp
    210                 215                 220
Glu His Asn Cys Thr His Asn Glu Asp Val Trp Val Glu Cys Glu Asp
225                 230                 235                 240
Pro Phe Ala Leu Lys Leu Val Gly Gly Arg Ser His Cys Glu Gly Arg
                245                 250                 255
Leu Glu Val Leu His Lys Gly Glu Trp Gly Ser Val Cys Asp Asp Gly
            260                 265                 270
Trp Gly Gln Asp Ala Asp Arg Val Cys Arg Gln Leu Gly Cys Gly
                275                 280                 285
Gln Pro Leu Ser Pro Pro Val Lys Val Arg Arg Phe Gly Pro Gly
    290                 295                 300
Val Gly Arg Ile Trp Leu Asp Asp Val Lys Cys Ser Gly Lys Glu Pro
305                 310                 315                 320
Ser Leu Glu Gln Cys Leu His Arg Ser Trp Gly Tyr His Asn Cys Asn
                325                 330                 335
His Arg Glu Asp Val Ala Val Val Cys Glu Glu Gln Ser Gly Leu
                340                 345                 350
Pro Asp Ala
        355

<210> SEQ ID NO 5
<211> LENGTH: 1196
<212> TYPE: DNA
<213> ORGANISM: Felis catus

<400> SEQUENCE: 5
agaactctcc gttgctgccc tggggcctcc tcgcggcctc ggattccagc tcagcctctc      60
ccgtcgcctg gctcatggcg ctactcttct ccctaatcct cgccatttac actggacctg     120
gcatttttagg gtctttttcc agagtgcggc tagtgggagg cgaccaccgc tgtgaaggtc    180
gtgtggagtt gcagcaggat gacgagtggg tcaccgtgtg tgatgactac tggaacatgg     240
actctgtggc cgtgctgtgc cgggagctgg gctgtggggc ggccaggaag accatgagtg     300
gcaccgtgta tggaccagtg acaccaaagg accaaaaagt cttcatccac ctgttcagat     360
gcaatgggat cgaagaaagc ctgtctcagt gcgagaggga agatgcaatc ggatgctccc     420
atgttgagga tgcggagcc gtgtgcgagc ccatttacac tggacctggc attttagggc       480
cggagagtgt gaggctggcc gatggccccg gcgctgcca gggccgagtg gaggtgaagt      540
tccgagggga gtggagctct gtgtgccaag caggctggag cttgcagcc gccaaggtgg     600
tgtgccggca gctgggtgt ggacgggcca ccctgacccg gagaggctgc aacaaagcga     660
cccagggcca aggggccatc tggcagagaa aggcgtcatg ctcaggacaa gaagtgagcc     720
ttcaagattg cctttctgaa gtttgggaac acaactgtac ccacaatgag acgtgtggg       780
tcgaatgtga gatcccttt gccttgaagc tggtaggagg acgcagccac tgtgagggga     840
ggctggaggt gctgcacaag ggcgagtggg gctctgtctg cgacgacggc tgggacaag     900
acgcagaccg ggtggtgtgc aggcagctgg gctgcgggca gccctgtct ccgcctgtca      960
aagtccggag aaggttcggc cccggggtcg gccgcatctg gctggacgac gtcaagtgct    1020
cggggaagga gccgtccctg agcagtgcc tgcacaggtc ctggggctac acaactgta     1080
accacagaga ggatgtggct gtggtctgtg aagaacagca gtctggccta cctgatgctt     1140
gacccacagg ccccaagcgc tcttacttct cctgggccct gatcggcccg gcctga       1196
```

<210> SEQ ID NO 6
<211> LENGTH: 352
<212> TYPE: PRT
<213> ORGANISM: Mus musculus

<400> SEQUENCE: 6

Met Ala Pro Leu Phe Asn Leu Met Leu Ala Ile Leu Ser Ile Phe Val
1               5                   10                  15

Gly Ser Cys Phe Ser Glu Ser Pro Thr Lys Val Gln Leu Val Gly Gly
                20                  25                  30

Ala His Arg Cys Glu Gly Arg Val Glu Val Glu His Asn Gly Gln Trp
            35                  40                  45

Gly Thr Val Cys Asp Asp Gly Trp Asp Arg Arg Asp Val Ala Val Val
        50                  55                  60

Cys Arg Glu Leu Asn Cys Gly Ala Val Ile Gln Thr Pro Arg Gly Ala
65                  70                  75                  80

Ser Tyr Gln Pro Pro Ala Ser Glu Gln Arg Val Leu Ile Gln Gly Val
                85                  90                  95

Asp Cys Asn Gly Thr Glu Asp Thr Leu Ala Gln Cys Glu Leu Asn Tyr
            100                 105                 110

Tyr Val Phe Asp Cys Ser His Glu Glu Asp Ala Gly Ala Gln Cys Glu
        115                 120                 125

Asn Pro Asp Ser Asp Leu Leu Phe Ile Pro Glu Asp Val Arg Leu Val
130                 135                 140

Asp Gly Pro Gly His Cys Gln Gly Arg Val Glu Val Leu His Gln Ser
145                 150                 155                 160

Gln Trp Ser Thr Val Cys Lys Ala Gly Trp Asn Leu Val Ser Lys
                165                 170                 175

Val Val Cys Arg Gln Leu Gly Cys Gly Arg Ala Leu Leu Thr Tyr Gly
            180                 185                 190

Ser Cys Asn Lys Asn Thr Gln Gly Lys Gly Pro Ile Trp Met Gly Lys
        195                 200                 205

Met Ser Cys Ser Gly Gln Glu Ala Asn Leu Arg Ser Cys Leu Leu Ser
210                 215                 220

Arg Leu Glu Asn Asn Cys Thr His Gly Glu Asp Thr Trp Met Glu Cys
225                 230                 235                 240

Glu Asp Pro Phe Glu Leu Lys Leu Val Gly Gly Asp Thr Pro Cys Ser
                245                 250                 255

Gly Arg Leu Glu Val Leu His Lys Gly Ser Trp Gly Ser Val Cys Asp
            260                 265                 270

Asp Asn Trp Gly Glu Lys Glu Asp Gln Val Val Cys Lys Gln Leu Gly
        275                 280                 285

Cys Gly Lys Ser Leu His Pro Ser Pro Lys Thr Arg Lys Ile Tyr Gly
290                 295                 300

Pro Gly Ala Gly Arg Ile Trp Leu Asp Asp Val Asn Cys Ser Gly Lys
305                 310                 315                 320

Glu Gln Ser Leu Glu Phe Cys Arg His Arg Leu Trp Gly Tyr His Asp
                325                 330                 335

Cys Thr His Lys Glu Asp Val Glu Val Ile Cys Thr Asp Phe Asp Val
            340                 345                 350